(12) United States Patent
White et al.

(10) Patent No.: US 8,518,922 B2
(45) Date of Patent: Aug. 27, 2013

(54) PHARMACEUTICAL SOLID STATE FORMS

(75) Inventors: Steven White, San Diego, CA (US); Erin Olson, San Diego, CA (US); Keith Lorimer, West Lafayette, IN (US); Brenton Skylar Wolfe, West Lafayette, IN (US)

(73) Assignee: Harbor Therapeutics, Inc., San Diego, CA (US)

( * ) Notice: Subject to any disclaimer, the term of this patent is extended or adjusted under 35 U.S.C. 154(b) by 961 days.

(21) Appl. No.: 12/370,510

(22) Filed: Feb. 12, 2009

(65) Prior Publication Data

US 2009/0291932 A1    Nov. 26, 2009

Related U.S. Application Data

(63) Continuation of application No. PCT/US2009/033280, filed on Feb. 5, 2009.

(60) Provisional application No. 61/093,694, filed on Sep. 2, 2008, provisional application No. 61/026,472, filed on Feb. 5, 2008.

(51) Int. Cl.
*A61K 31/567* (2006.01)
*C07J 1/00* (2006.01)

(52) U.S. Cl.
USPC ............................................. 514/182; 552/641

(58) Field of Classification Search
CPC ................................. C07J 1/00; A61K 31/567
USPC ......................................... 552/641; 514/182
See application file for complete search history.

(56) References Cited

U.S. PATENT DOCUMENTS

| | | | |
|---|---|---|---|
| 2,267,257 A | 12/1941 | Ruzicka | |
| 5,567,830 A | 10/1996 | Upasani | |
| 6,143,910 A | 11/2000 | Bishop et al. | |
| 6,451,340 B1 | 9/2002 | Arimilli et al. | |
| 7,045,513 B1 | 5/2006 | Parasrampuria et al. | |
| 7,205,290 B2 | 4/2007 | Jaehne et al. | |
| 7,691,835 B2 | 4/2010 | Frincke | |
| 7,867,990 B2 | 1/2011 | Schultz et al. | |
| 7,906,497 B2 | 3/2011 | Frincke | |
| 7,964,604 B2 | 6/2011 | Eijgendaal et al. | |
| 8,003,636 B2 | 8/2011 | Wollmann et al. | |
| 2004/0224932 A1 | 11/2004 | Biggadike et al. | |
| 2007/0129548 A1 | 6/2007 | Tan et al. | |
| 2008/0021006 A1 | 1/2008 | Lardy et al. | |

FOREIGN PATENT DOCUMENTS

| | | |
|---|---|---|
| CA | 2386095 | 4/2001 |
| EP | 1832598 A2 | 12/2007 |
| EP | 1955700 A2 | 8/2008 |
| WO | WO 97/36893 | 10/1997 |
| WO | WO 01/23405 A1 | 4/2001 |
| WO | WO 02/66449 | 8/2002 |

OTHER PUBLICATIONS

WO 09/100258 international search report, Apr. 8 , 2009.
*ex parte Grawe*, Appeal No. 2009-14303, U.S. Appl. No. 10/296,463 (non-precedential), 2009.
*ex parte Bush*, Appeal No. 2009-010640 U.S. Appl. No. 10/520,360 (non-precedential), 2009.
*ex parte Zimmerman*, Appeal No. 2003-0919, U.S. Appl. No. 09/463,097, (non-precedential), 2003.
Starrett, J. et al. (1994) "Synthesis, Oral Bioavailability Determination, and in vitro Evaluation of Prodrugs of the Antiviral Agent 9-[2-(Phosphonomethoxy)ethyl]adenine (PMEA)" J. Med. Chem. 37: 1857-64.

*Primary Examiner* — Barbara P Badio
(74) *Attorney, Agent, or Firm* — Angelo Ostellino

(57) ABSTRACT

The invention provides and describes solid state 17α-ethynyl-5α-androstane-3α,17β-diol including amorphous and crystalline forms and specific polymorphic forms thereof. Anhydrates and solvates of 17α-ethynyl-5α-androstane-3α,17β-diol include Form III anhydrate and Form I solvate. The invention further relates to solid and suspension formulations containing 17α-ethynyl-5α-androstane-3α,17β-diol in a described solid state form and use of the formulations to treat cancers or precancers such as prostate cancer or breast cancer in subjects or human patients. The invention also relates to methods to make liquid formulations from solid state forms of 17α-ethynyl-5α-androstane-3α,17β-diol and uses of such formulations in treating the described conditions.

15 Claims, 18 Drawing Sheets

2.5x Magnification    10x Magnification 2.5x Magnification    10x Magnification

PHARMACEUTICAL SOLID STATE FORMS

CROSS REFERENCE TO RELATED APPLICATIONS

This nonprovisional U.S. patent application is a continuation of and claims priority under 35 USC 365(c) from PCT international patent application serial No. PCT/US09/33280 filed Feb. 5, 2009, which claims priority from U.S. provisional application Ser. No. 61/093,694 filed Sep. 2, 2008, now abandoned, and U.S. provisional application Ser. No. 61/026,472, now abandoned, filed Feb. 5, 2008, all of which are incorporated herein by reference in their entireties.

FIELD OF THE INVENTION

The invention relates to 17-ethynyl-10R,13S-dimethyl-2,3,4,5S,6,7,8R,9S,10,11,12,13,14S,15,16,17-hexadecahydro-1H-cyclopenta[a]-phenanthrene-3S,17S-diol and its solid state forms, including crystalline, polymorph, pseudopolymorph and amorphous forms and methods for their preparing the solid state forms. The invention further relates to solid formulations comprising the solid state forms and to methods for using the solid state forms, including the polymorph forms and pseudopolymorph forms, in preparing solid and liquid formulations and uses of these formulations for the treatment of cancer, including hormone sensitive or hormone associated cancers such as breast cancer, prostate cancer, and for the treatment of precancers and hyperplasias such as benign prostate hyperplasia. Unit dosage forms for the solid and liquid formulations are also included.

BACKGROUND OF THE INVENTION

The ability of a substance to exist in more than one crystalline form is generally referred to as polymorphism and these different crystalline forms are usually named "polymorphs" and may be referred to by certain analytical properties such their X-ray powder diffraction (XRPD) patterns. In general, polymorphism reflects the ability of a molecule to change its conformation or to form different intermolecular and intramolecular interactions. This can result in different atom arrangements that is reflected in the crystal lattices of different polymorphs. However, polymorphism is not a universal feature of solids, since some molecules can exist in one or more crystal forms while other molecules cannot. Therefore, the existence or extent of polymorphism for a given compound is unpredictable.

The different polymorphs of a substance posses different crystal lattice energies and thus each polymorph typically shows one or more different physical properties in the solid state, such as density, melting point, color, stability, dissolution rate, flowability, compatibility with milling, granulation and compacting and/or uniformity of distribution [See, e.g., P. DiMartino, et al., *J. Thermal Anal.* 48:447-458 (1997)]. The capacity of any given compound to occur in one or more crystalline forms (i.e. polymorphs) is unpredictable as are the physical properties of any single crystalline form. The physical properties of a polymorphic form may affect its suitability in pharmaceutical formulations. Those properties can affect the stability, dissolution and bioavailability of a solid-state formulation, which subsequently affects suitability or efficacy of such formulations in treating disease.

An individual polymorph having one or more desirable properties can be suitable for the development of a pharmaceutical formulation having desired property(ies). Existence of a compound with a polymorphic form(s) having undesirable properties can impede or prevent development of the polymorphic form as a pharmaceutical agent.

In the case of a chemical substance that exists in more than one polymorphic form, the less thermodynamically stable forms can occasionally convert to the more thermodynamically stable form at a given temperature after a sufficient period of time. When this transformation is not rapid, such a thermodynamically unstable form is referred to as a "metastable" form. In some instances, the stable form exhibits the highest melting point, the lowest solubility, and the maximum chemical stability. In other cases, the metastable form may exhibit sufficient chemical and physical stability under normal storage conditions to permit its use in a commercial form. In this case, the metastable form, although less thermodynamically stable, may exhibit properties desirable over those of the stable form, such as enhanced solubility or better oral bioavailability. Likewise, the amorphous form of an active pharmaceutical ingredient may have different solubility in comparison to a given crystalline material due reduction of crystal lattice forces in the amorphous material that must be overcome to effect dissolution in aqueous or non-aqueous liquids.

SUMMARY OF THE INVENTION

In a principal embodiment, the invention provides new solid state forms of 17-Ethynyl-10R,13S-dimethyl-2,3,4,5S,6,7,8R,9S,10,11,12,13,14S,15,16,17-hexadecahydro-1H-cyclopenta[a]phenanthrene-3S,17S-diol, which is represented by Formula I. This compound is suitable for treating a hyperproliferation condition such as cancer or precancer and in particular, a hormone sensitive or associated cancer, precancer or benign hyperplasia, such as prostate cancer, breast cancer, prostatic intraepithelial neoplasia or benign prostatic hypertrophy.

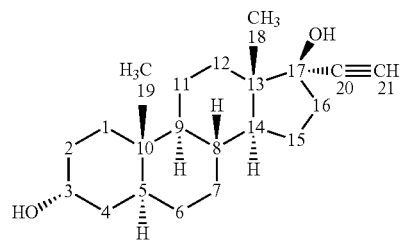

Formula 1

The compound of Formula I (hereafter also referred to as Compound 1 or 17α-ethynyl-5α-androstane-3α,17β-diol) has been prepared in amorphous and crystalline forms, and in particular, crystalline forms referred herein as Form I, Form III, Form IV, Form V, Form VI, Form VII and Form VIII.

One embodiment of the invention is directed to a particular crystalline form of Compound 1 (e.g., Form I, Form III, Form IV, Form V, Form VI, Form VII, Form VIII) substantially free or essentially free of other crystalline or amorphous forms of Compound 1.

In certain embodiments, the present invention is directed to a particular polymorph form (e.g., Form III) or pseudopolymorph form (e.g., Form I) of Compound 1 that is substantially free or essentially free of other polymorph or pseudopolymorph forms of Compound 1.

Another embodiment of the invention is directed to amorphous Compound 1, typically wherein the amorphous material is substantially free or essentially free of crystalline Compound 1.

In certain embodiments, the present invention provides methods of making, isolating and/or characterizing the solid state forms of the invention. Some of these embodiments are directed to methods to prepare Compound 1 in crystalline form. Other such embodiments are directed to methods to prepare Compound 1 in amorphous form.

In some embodiments a solid state form of Compound 1 is characterized or identified by methods comprising X-ray Powder Diffraction (XRPD) and one or more thermal methods including Differential Thermal Analysis (DTA), Differential Scanning Calorimetry (DSC), Thermogravimetric Analysis (TGA) and melting point measurements.

In some embodiments a solid state form of Compound 1 is characterized or identified by methods including XRPD and a vibrational spectroscopy method such as Raman spectroscopy.

In some embodiments a solid state form of Compound 1 is characterized or identified by methods including single crystal X-ray diffraction.

In some embodiments a solid state form of Compound 1 is characterized or identified by methods including $^1$H-NMR, elemental analysis, Karl-Fisher titration, thermogravimetric analysis or a combination thereof.

In some embodiments a crystalline form of Compound 1 is identified or characterized by a method comprising the steps of (1) obtaining unit cell parameters for a reference crystalline form; (2) obtaining one or more high resolution XRPD patterns for the crystalline form to be identified or characterized and indexing the high resolution XRPD pattern so obtained; (3) determining unit cell parameters for the crystalline form to be identified or characterized from the indexed high resolution XRPD pattern(s); and (4) comparing the unit cell parameters for the reference crystalline form and the crystalline form to be identified. In certain embodiments of this method, the unit cell parameters for the reference crystalline form is obtained from single crystal X-ray data. In other embodiments of this method the unit cell parameters for the reference crystalline form are obtained from indexed high resolution XRPD pattern(s). In still other embodiments of this method the crystalline form to be identified or characterized is a polymorph or pseudopolymorph and the reference is another polymorph or pseudopolymorph to be identified or characterized. In some of these methods the crystalline form to be identified is a pseudopolymorph and the reference is an anhydrate, preferably an isostructural anhydrate. In still other embodiments of these methods, the unit cell parameters that are compared are crystal volumes derived for an isostructural reference crystalline form and the crystalline form to be characterized.

Other embodiments of the invention are directed to solid formulations comprising a solid state form of Compound 1 and methods for preparation of the solid formulation.

In certain embodiments, the present invention encompasses the use of the solid state forms of the invention as a final drug product.

Other embodiments of the invention are directed to pharmaceutically acceptable formulations comprising a particular crystalline form (e.g. Form I, Form III, Form IV, Form V, Form VI, Form VII, Form VIII) of Compound 1 that is substantially free or essentially free of other solid state forms, such as amorphous or other crystalline forms of Compound 1, and methods for preparation of the formulations.

Still other embodiments of the invention are directed to liquid formulations prepared by contacting or admixing at least one solid state form of Compound 1 with a liquid excipient into which Compound 1 has sufficient solubility, optionally in the presence of another excipient, and methods for preparation of the liquid formulation.

Yet another embodiment of the invention is directed to methods for treating a cancer or hyperproliferation condition such as a hormone associated cancer or hormone sensitive cancer including ovarian cancer, endometrial cancer, prostate cancer or breast cancer in a subject with a solid formulation comprising a solid state form of Compound 1 such as amorphous or a crystalline form of Compound 1.

Yet another embodiment of the invention is directed to methods for treating a hormone associated cancer or hormone sensitive cancer such as ovarian cancer, endometrial cancer, prostate cancer or breast cancer in a subject with a solid formulation comprising a particular crystalline form (e.g. Form I, Form III, Form IV, Form V, Form VI, Form VII, Form VIII) of Compound 1 that is substantially free of other solid state forms, such as amorphous and other crystalline forms, of Compound 1

Another embodiment of the invention is directed to methods for treating endometriosis or benign prostate hyperplasia in a subject with a solid formulation comprising a solid state form of Compound 1 such as amorphous or a crystalline form of Compound 1.

Invention embodiments also include the use or Compound 1 in amorphous or crystalline form for the preparation of a medicament for the treatment or prophylaxis of a hormone associated or sensitive cancer, precancer or hyperplasia such as prostate cancer, breast cancer, prostatic intraepithelial neoplasia or benign prostatic hypertrophy.

Still other embodiments are directed to methods for preparing liquid formulations using a solid state form of Compound 1 and uses of such formulations for treating a hormone associated cancer or hormone sensitive cancer.

Other embodiments and advantages of the present invention are as described elsewhere in the specification including the numbered embodiments and the claims.

DETAILED DESCRIPTION

Definitions

Figure 1:
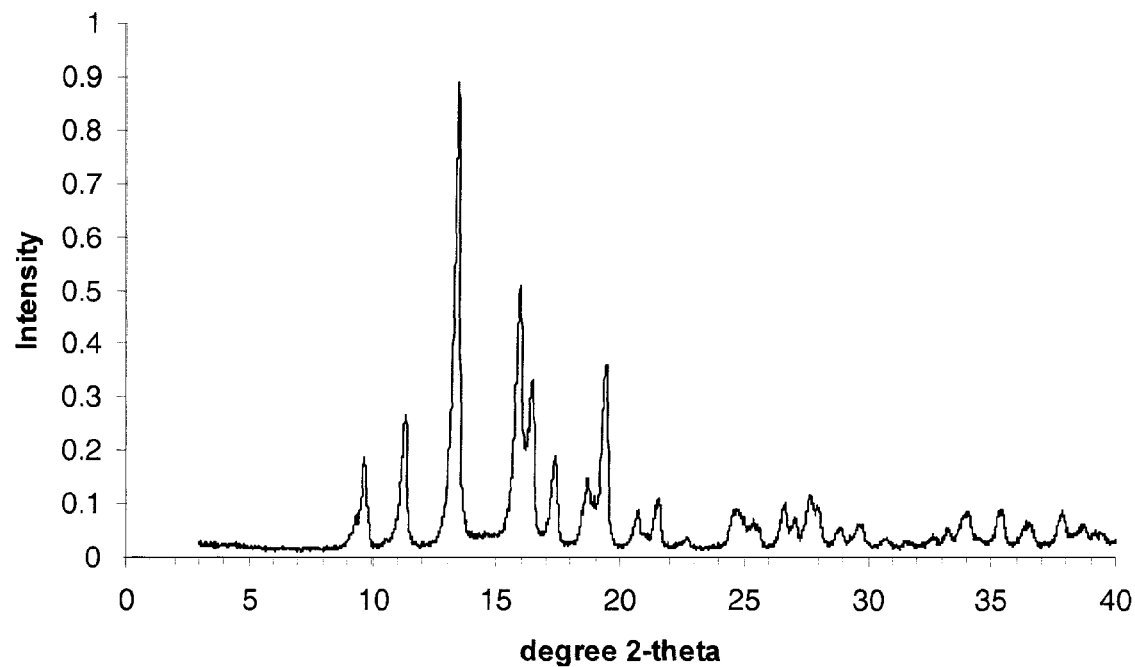
FIG. 1 provides a low resolution X-ray powder diffraction pattern of a synthesis product obtained in the preparation of bulk Compound 1.

As used herein or otherwise stated or implied by context, terms that are defined herein have the meanings that are specified. The descriptions of embodiments and examples that are described illustrate the invention and they are not intended to limit it in any way. Unless otherwise contraindicated or implied, e.g., by mutually elements or options, in the descriptions or throughout this specification, the terms "a" and "an" mean one or more and the term "or" means and/or.

Unless specified otherwise explicitly or by context, percentage amounts are expressed as % by weight (w/w). Thus, a solid-dosage formulation containing at least about 2% Compound 1 is a solid-dosage formulation or suspension containing at least about 2% w/w Compound 1. Solid Compound 1 containing 0.1% water means 0.1% w/w water is associated with the solid.

"About" and "approximately," when used in connection with a numeric value or range of values which is provided to describe a particular solid form, e.g., a specific temperature or temperature range, such as, for example, that describing a melting, dehydration, desolvation or glass transition; a mass change, such as, for example, a mass change as a function of temperature or humidity; a solvent or water content, in terms of, for example, mass or a percentage; or a peak position, such as, for example, in analysis by IR or Raman spectroscopy or XRPD; indicate that the value or range of values may deviate to an extent deemed reasonable to one of ordinary skill in the art while still describing the particular solid state form. Specifically, the terms "about" and "approximately," when used in this context, indicate that the numeric value or range of values may vary by 20%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1% or 0.01% of the recited value or range of values while still describing the particular composition or solid state form.

"Solid State" as used herein refers to a physical state of a compound or composition comprising the compound, such as 17α-ethynyl-5α-androstane-3α,17β-diol (i.e., Compound 1); wherein at least about 2-10% of the mass of the compound that is present exists as a solid. Typically, the majority of the mass of Compound 1 will be in solid state form. More typically, between at least about 80-90% of the mass of Compound 1 is in solid form. Solid state forms include crystalline, disordered crystalline, polycrystalline, microcrystalline, nanocrystalline, partially crystalline, amorphous and semi-solid forms or mixtures thereof, optionally with non-solid or non-crystalline Compound 1. Solid state forms of Compound 1 further include polymorphs, pseudopolymorphs, hydrates, solvates, dehydrated hydrates and desolvated solvates and mixtures thereof, optionally with non-solid or non-crystalline Compound 1. Thus, solid state forms of Compound 1 will include a single polymorph form of Compound 1, a single pseudo-polymorph form of Compound 1, a mixture of two or more, typically two or three, polymorph or pseudo-polymorph forms of Compound 1 or a combination of any one of these solid state forms, optionally with non-solid or non-crystalline Compound 1, provided that at least about 2-10% of the mass of Compound 1 is in solid form.

The term "crystalline" and related terms used herein, when used to describe a substance, component or product, means that the substance, component or product is crystalline as determined by a suitable method, typically X-ray diffraction [See, e.g., Remington's Pharmaceutical Sciences, 18$^{th}$ ed., Mack Publishing, Easton Pa., p 173 (1990); The United States Pharmacopeia, 23$^{rd}$ ed., pp. 1843-1844 (1995)].

The term "crystalline forms" and related terms herein refers to the various crystalline modifications of a given substance, including, but not limited to, polymorphs, solvates, hydrates, mixed solvates, co-crystals and other molecular complexes. A crystalline form may also be a mixture various crystalline modifications of a given substance such as a combination of pseudopolymorph or polymorph forms, a combination of one or more polymorph forms with one or more pseudopolymorph or a combination of such forms with amorphous or non-solid state forms of the substance. Typical combinations with be of two or more polymorph or pseudo polymorph forms, such a mixture of a polymorph form with a pseudopolymorph form or a mixture of a polymorph or pseudopolymorph form with amorphous material.

Crystalline forms of a substance can be obtained by a number of methods, as known in the art. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, grinding and solvent-drop grinding.

"Polymorph" as used herein refers to a defined crystalline form of a substance such as Compound 1. Polymorphs typically differ in their physical properties due to the order of the molecules in the lattice of the polymorph. In addition, the physical properties of a polymorph can differ, e.g., stability or flow characteristics, due to the presence of hydrates, solvates or other molecules incorporated into the lattice of the polymorph.

In terms of thermodynamics, there are two types of polymorphism. For example, when polymorphs have a monotropic relationship, a plot of the free energy of the various polymorphs in this relationship against temperature does not cross before all polymorphs melt, i.e., any transition from one polymorph to another will be irreversible. Polymorphs that have a monotropic relationship are sometimes referred to as monotropes. For polymorphs having enantiotropic relationship, a plot of the free energy of the various polymorphs in this relationship against temperature shows a crossing point before the various melting points, and thus it may be possible to convert reversibly between the two polymorphs on heating and cooling. Polymorphs that have an enantiotropic relationship are sometimes referred to as enantiotropes.

Polymorphs may exhibit one or more differences in physical or pharmaceutical properties including hygroscopicity, solubility, intrinsic dissolution rate, solid state reaction rates (i.e., chemical stability of a pharmaceutical ingredient as the drug substance or drug product), crystalline stability (i.e. tendency to transition to a more thermodynamically stable crystalline form), surface free energy, interfacial tension, mechanical strength (e.g., hardness, brittleness, plastic deformation, docility, malleability, etc.), tensile strength, compactability (i.e., tableting) and processability (e.g., handling, flow, blending, etc.). Differences in physical and mechanical properties of polymorphic forms of a drug substance may also affect scale-up and transfer from laboratory procedures though pilot plant and then to full production. Changes in equipment, variations in heating and cooling rates and variations in stirring procedures may also affect crystallization and thus influence the crystalline form that is obtained.

Polymorphs existing as hydrates, solvates or mixed solvates are generally referred to as pseudopolymorphs and represent different solid state forms in view of an isostructural polymorph form that is anhydrous or not a solvate. Pseudopolymorphs that differ in solvate identity or stoichiometry are also considered different solid state forms in view of each other. For example, Compound 1 existing as a monohydrate is a different solid state form in view of its isostructural dihydrate. Additionally, a methanol-water solvate (i.e., a mixed solvate) of Compound 1 is viewed as a different solid state form in view of its isostructural hydrate or anhydrate. Solvates and hydrates generally demonstrate different solubilities or different intrinsic dissolution rates compared to its isostructural anhydrate or desolvate. For example, a solvate may exhibit a lower intrinsic dissolution rate in the solvent that comprises the solvate as compared to its isostructural desolvate at a given temperature. Thus, a hydrate may sometimes exhibit a lower intrinsic dissolution rate in an aqueous solution as compared to its isostructural anhydrate. Furthermore, stability profiles of hydrates and solvates at various temperatures and/or at different vapor pressures of water (e.g., relative humidity) or organic solvents will sometimes differ from those of the isostructural anhydrate or desolvate. Such differences may influence formulation, processing or stability of an active pharmaceutical ingredient (e.g., Compound 1), either as the drug substance or drug product under various storage conditions.

Thus, different crystalline or polymorphic forms may have different physical properties such as, for example, melting temperatures, heats of fusion, solubilities, and/or vibrational spectra as a result of the arrangement or conformation of the molecules in the crystal lattice (see, e.g., Byrn, S. R., Pfeiffer, R. R., and Stowell, J. G. (1999) Solid-State Chemistry of Drugs, $2^{nd}$ ed., SSCI, Inc.: West Lafayette, Ind.). The differences in physical properties exhibited by polymorphs and pseudopolymorphs may affect pharmaceutical parameters such as storage stability, compressibility and density (important in formulation and product manufacturing), and intrinsic dissolution rate, which can be an important factor in bioavailability. Differences in stability may result from changes in chemical reactivity (e.g., differential oxidation, such that a dosage form discolors more rapidly when comprised of one polymorph or pseudopolymorph than when comprised of another polymorphic form) or mechanical changes (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing, for example, one polymorph might be more likely to form solvates or hydrates that may be difficult to filter and wash free of impurities (i.e., particle shape and size distribution might be different between polymorphs).

Typically, crystalline forms are readily distinguished from each other by one or more physical or analytical properties such as rate of dissolution, Infrared and Raman spectroscopy, X-ray diffraction techniques such as single crystal and powder diffraction techniques, solid state-NMR (SS-NMR), thermal techniques such as melting point, differential thermal analysis (DTA), differential scanning calorimetry (DSC), thermal gravimetric analysis (TGA) and other methods as disclosed elsewhere in the specification. Additional methods to characterize or distinguish a pseudopolymorph from another isostructural polymorph, pseudopolymorph, desolvate or anhydrate include elemental analysis, Karl-Fisher titration, dynamic vapor sorption analysis, thermogravimetric-infrared spectroscopic analysis (TG-IR), residual solvent gas chromatography, $^1$H-NMR and other methods as disclosed elsewhere in the specification.

The term "isostructural crystalline form," as used herein, refers to a crystal form of a substance that has a common structural similarity with another crystalline form, including approximately similar interplanar spacing in the crystal lattice. [A more detailed account of crystal lattices can be found in Chapters 2 and 3 of Stout and Jensen, X-Ray Structure Determination: A Practical Guide, MacMillan Co., New York (1968)]. Thus, isostructural crystalline forms will have similar molecular packing motifs, but differing unit cell parameters (a symmetry translation). Due to their common structural similarity, isostructural crystalline forms typically have similar, but not necessarily identical, X-ray powder diffraction patterns. An isostructural crystalline form may be based upon a substance that is a neutral molecule or a molecular complex. The isostructural crystalline form may be a solvate, including a hydrate, or a desolvated solvate crystalline form of the substance. Isostructural forms that are solvates of a polymorph are sometimes referred to as pseudopolymorphic to the unsolvated polymorph. A solvated crystalline form typically contains one or more solvents, including water, in the crystal lattice, that may be the solvent or solvents of crystallization used in preparing the crystalline form.

"Amorphous", as used herein, refers to a solid state form of a compound (e.g., Compound 1) wherein the solid state form has no long-range periodic atomic structure as determined by X-ray powder diffraction (XRPD). The XRPD pattern of amorphous material will appear as a halo with no distinctive peaks. Amorphous material for some compounds can be obtained by a number of methods known in the art. Such methods include, but are not limited to, heating, melt cooling, rapid melt cooling, solvent evaporation, rapid solvent evaporation, desolvation, sublimation, grinding, cryo-grinding and freeze drying.

"Formulation" or "pharmaceutically acceptable formulation" as used herein refers to a composition comprising an active pharmaceutical ingredient, such as 17α-ethynyl-5α-androstane-3α,17β-diol (i.e., Compound 1), present in a solid state form in addition to one or more pharmaceutically acceptable excipients or refers to a composition prepared from a solid state form of the active pharmaceutical ingredient, wherein the composition is suitable for administration to a human. The formulation may be comprised of, or be prepared from, one, two or more crystalline forms of the active pharmaceutical ingredient (e.g. a single polymorph or pseudopolymorph form of Compound 1, a mixture of two polymorph forms of Compound 1, a mixture of a polymorph form of Compound 1 and a pseudopolymorph form of Compound 1 or a mixture of a polymorph or pseudopolymorph form of Compound 1 and amorphous Compound 1. Typically, the formulations will be comprised of, or prepared from, a single crystalline form of Compound 1 (e.g., Form I, Form III, Form IV, Form V, Form VI, Form VII, Form VIII), amorphous Compound 1 or, less preferably, a mixture of a single polymorph or pseudopolymorph form and amorphous Compound 1.

"Solid state formulation" or "solid formulation" as used herein refers to a formulation comprising a solid state form of Compound 1 and one or more pharmaceutically acceptable excipients wherein the majority of the mass amount of the solid state form remains in that solid state form for at least about 6 months at ambient temperature, usually for at least about 12 months or 24 months at ambient temperature, when admixed with the excipients in proportions required for the solid state formulation. Dosage units containing a solid state formulation include tablets, capsules, caplets, gelcaps, ampoules, suspensions and other dosage units typically associated with parenteral or enteral (oral) administration of an active pharmaceutical ingredient in solid state form to a subject in need thereof.

"Liquid formulation" as used herein refers to a formulation wherein one or more solid state forms of Compound 1 has been admixed or contacted with one or more excipients, wherein at least one of the excipients is in liquid or non-solid state form (i.e. a non-solid excipient), in proportions required for the liquid formulation, such that a majority of the mass amount of Compound 1 is dissolved into the non-solid excipient. Dosage units containing a liquid formulation include syrups, gels, ointments and other dosage units typically associated with parenteral or enteral administration of an active pharmaceutical ingredient to a subject in need thereof in non-solid state form.

"Substantially free" as used herein refers to a compound such as Compound 1 wherein more than about 60% by weight of the compound is present as the given solid state form. For example, the term "crystalline Compound 1 substantially free of amorphous material" refers to a solid-state form of Compound 1 wherein more than about 60% of Compound 1 is crystalline Compound 1. Such compositions typically contain at least about 80%, preferably at least about 90%, of crystalline Compound 1 with the remaining present as amorphous or non-crystalline Compound 1. Formulations described herein will typically contain about 94-99% of a single crystalline or amorphous form of Compound 1, with about 97%, about 98% or about 99% preferred. In another example, the term "amorphous Compound 1 substantially free of crystalline forms" refers to a solid-state form of Compound 1 wherein more than about 60% of Compound 1 is amorphous. Such compositions typically contain at least about 80%, usually at least about 90%, preferably at least about 95%, of amorphous Compound 1, with the remaining present as crystalline Compound 1. In yet another example, the term "Form III substantially free of other crystalline forms" refers to a solid-state composition wherein more than about 60% of Compound 1 exists in crystalline form as Form III. Such compositions typically contain at least about 80%, preferably at least about 90% and more preferably at least about 97% of Compound 1 as Form III, with the remaining Compound 1 present as other crystalline or amorphous forms or a combination thereof.

"Substantially pure" as used herein refers to a solid state form of Compound 1 that contain less than about 3% or less than about 2% by weight total impurities, or more preferably less than about 1% by weight water, and/or less than about 0.5% by weight impurities such as decomposition or synthesis by-products or residual organic solvent that is not part of a solvate of a solid state form of Compound 1 (e.g. not part of a pseudopolymorph) or other "Substantially identical" as used herein refers to measured physical characteristics that are comparable in value or data traces that are comparable in peak position and amplitude or intensity with variations typically associated with sample positioning or handling or the identity of the instrument employed to acquire the traces or physical characteristics or due to other variations or fluctuations normally encountered within or between laboratory environments or analytical instrumentation.

"Essentially free" as used herein refers to a component so identified as not being present in an amount that is detectable under typical conditions used for its detection or would adversely affect the desired properties of a composition or formulation in which the component may be found. For example, "essentially free of liquid" means a composition or formulation in solid form that does not contain water or solvent, in liquid form, in an amount that would adversely affect the pharmaceutical acceptability of the formulation or composition for use in a solid dosage form to be administered to a subject in need thereof. A suspension is considered a solid formulation and for such formulations liquid excipient(s)

comprising the suspension formulation are not included within this definition. "Polymorph Form III essentially free of amorphous Compound 1" refers to a specific crystalline form of Compound 1 in which amorphous Compound 1 is not detected by XRPD analysis. Typically, the detection limit for amorphous material within a crystalline form is about 10%.

"Hydrate" as used here refers to solid state form of a compound so identified that contains water molecules as an integral part of the solid state form and does not refer to water that is non-specifically bound to the bulk compound. Hydrates of Compound 1 in a crystalline form can be isolated site hydrates or channel hydrates. In the crystal structure of an isolated site hydrate the water molecules are isolated from direct contact with other water molecules by the Compound 1 molecules, whereas in channel hydrates the water molecules are located next to each other along one direction in the lattice. Hydrates can contain stoichiometric or nonstoichiometric amounts of water molecules per Compound 1 molecule. An expanded channel hydrate can take up water into the channels when exposed to high humidity and release water when exposed to relatively low humidity. The crystal lattice of such hydrates can expand or contract as hydrate formation or dehydration proceeds, changing the dimensions of the unit cell. Typically, water will be present in a stoichiometric hydrate in the ratio of 0.25, 0.5, 1.0, 1.5 or 2.0 relative to Compound 1. Hydrates are usually more stable than their anhydrous counterparts at conditions below its dehydration temperature. Isolated site hydrates usually dehydrate at relatively higher temperatures than channel hydrates. The dehydration process of isolated site hydrates is sometimes destructive for the crystal structure since it sometimes requires rearrangement of the molecules in the unit cell in order to allow water molecules to escape the lattice.

"Solvate" as used here refers to solid state form of a compound so identified that contains solvent molecules that is combined in a definite ratio to the molecules of the compound and is an integral part of the solid state form and does not refer to solvent that is non-specifically bound to bulk compound. When the solvent molecule is water such solvates are referred to as hydrates. Typically, solvent will be present in a solvate in the ratio of 0.25, 0.5, 1.0, 1.5 or 2.0 relative to Compound 1.

"Hyperproliferation condition" or "cancer" as used here refers to a condition that is characterized by an abnormally high rate or a persistent state of cell division that is uncoordinated with that of the surrounding normal tissues, and persists after, e.g., cessation of the stimulus that may have initially evoked the change in cell division. This uncontrolled and progressive state of cell proliferation may result in a tumor that is benign, potentially malignant (premalignant) or frankly malignant. Hyperproliferation conditions include those characterized as a hyperplasia, dysplasia, adenoma, sarcoma, blastoma, carcinoma, lymphoma, leukemia or papilloma or other conditions described herein.

"Hormone associated cancer, precancer or benign hyperplasia" or "hormone sensitive cancer, precancer or benign hyperplasia" as used herein refers to a hyperproliferation condition that responds negatively or positively in a therapeutic sense, to hormone manipulation or is a condition whose genesis, persistence, invasiveness, refractivity, severity in symptoms or responsiveness to chemotherapy are attributable or related, in part or in whole, to hormone levels. Hormone associated or hormone sensitive cancers include, prostate cancer, breast cancer, ovarian cancer, cervical cancer, uterine cancer, endometrial carcinoma, adenocarcinoma, malignant melanoma or other conditions as described herein. Some additional hormone associated or related cancers are described in Miller, A. B. *Cancer Res.* 38: 3985-3990 (1978).

Precancers are usually defined as lesions that exhibit histological changes which are associated with an increased risk of cancer development and sometimes have some, but not all, of the molecular and phenotypic properties that characterize the cancer. Hormone associated or hormone sensitive precancers include, prostatic intraepithelial neoplasia (PIN), particularly high-grade PIN (HGPIN), atypical small acinar proliferation (ASAP), cervical dysplasia and ductal carcinoma in situ.

Hyperplasias generally refers to the proliferation of cells within an organ or tissue beyond that which is ordinarily seen that may result in the gross enlargement of an organ or in the formation of a benign tumor or growth. Hormone associated or hormone sensitive hyperplasias include, endometrial hyperplasia (endometriosis), benign prostatic hyperplasia and ductal hyperplasia.

An "excipient", "carrier", "pharmaceutically acceptable carrier" or similar terms mean one or more component(s) or ingredient(s) that is acceptable in the sense of being compatible with the other ingredients in compositions or formulations comprising Compound 1 as the active pharmaceutical ingredient that is in solid state form when admixed with the excipients. These excipients usually are not overly deleterious to a subject to whom the composition formulation is to be administered. As used here, "excipients" include liquids, such as water for injection, benzyl benzoate, cottonseed oil, N,N-dimethylacetamide, an alcohol such as methanol, ethanol, glycerol, peanut oil, a polyethylene glycol ("PEG"), vitamin E, poppy seed oil, propylene glycol, safflower oil, sesame oil, soybean oil and vegetable oil. Excipients also include dissolution aids typically used for active pharmaceutical ingredients that are sparingly soluble or insoluble in water. Dissolution aids include a cyclodextrin or a cyclodextrin derivative such as β-cyclodextrin, 2-hydroxypropyl-β-cyclodextrin and CAPTISOL™ (sulfobutyl ether-β-cyclodextrin) and a PEG or PEG derivative such as CHREMOPHOR™ (a polyethoxylated castor oil). Any solid excipient may be a fine powder or granulated. Excipients, as used herein may optionally exclude one or more excipient, e.g., chloroform, dioxane, vegetable oil, DMSO, other excipients or any combination of these. Excipients include one or more components typically used in the pharmaceutical formulation arts, e.g., one, two or more of fillers, binders, disintegrants, dispersants, preservatives, glidants, surfactants and lubricants. Exemplary excipients include povidone, crospovidone, corn starch, carboxymethyl cellulose, hydroxypropyl methylcellulose, microcrystalline cellulose, gum arabic, polysorbate 80, butylparaben, propylparaben, methylparaben, BHA, EDTA, sodium lauryl sulfate, sodium chloride, potassium chloride, titanium dioxide, magnesium stearate, castor oil, olive oil, vegetable oil, buffering agents such as sodium hydroxide, monobasic sodium phosphate, dibasic sodium phosphate, potassium hydroxide, monobasic potassium phosphate, dibasic potassium phosphate, tribasic potassium phosphate, potassium carbonate, potassium bicarbonate, ammonium hydroxide, ammonium chloride, saccharides such as mannitol, glucose, fructose, sucrose or lactose any of which may be compressible or any of which may be spray dried.

A "subject" means a human or an animal. Usually the animal is a mammal or vertebrate such as a non-human primate dog or rodent. Subsets of subjects include subjects of a given species or group of species of varying ages, e.g., young humans, e.g., about 1 week of age to about 9 years of age, adolescent humans, e.g., about 10-19 years of age, adult humans, e.g., about 20-100 years of age, and mature adult or elderly humans, e.g., at least about 55 years of age, at least about 60 years of age, at least about 65 years of age or a range of ages such as about 60-100 years of age. Thus, as used herein, prevention or treatment of a disease, condition or symptom may include or exclude any subset of subjects that are grouped by age.

The terms "effective amount", "effective dose" or the like generally means an amount of a solid state form of Compound 1 or an amount of Compound 1 in a formulation comprised of or prepared from a solid state form of Compound 1 that is sufficient to elicit a desired response, e.g., detectable restoration of normal physiological condition in a subject to which it is administered such as a decrease or stabilization in tumor burden, detectable decrease of a cancer or hyperproliferation biomarker, which may be a cell-surface biomarker or a circulating biomarker, a slowing in the rate of increase of the cancer or hyperproliferation biomarker or to detectable modulation or amelioration of a cellular parameter or a clinical condition or symptom. An effective amount may be a single dose or two or more subdoses of Compound 1 in a formulation comprised of or prepared from a solid state form of Compound 1 administered in one day, or it may be administered as multiple doses over a period of time, e.g., over 2 days to about 1, 2, 3, 4 or 5 years. The effective amount may also be administered in multiple treatment cycles as typically done in administration of cytotoxic agents for the treatment of cancer. The treatment cycles may be separated by one or more days or weeks, typically 1-4 weeks or may be separated by a longer period of time if remission of the hyperproliferation condition is achieved whereupon treatment is reinstituted upon recurrence of the condition. Treatment cycles include daily administration of Compound 1 for 4 weeks or 12 weeks.

"Prevent" or "prevention" of a condition or symptom as used here means that the onset of the condition or symptom can in some subjects be delayed for at least some period of time in at least some treated subjects. "Prevent" or "prevention" can also be viewed as a delay in detectable dissemination of the hyperproliferation condition as measured by delayed appearance of new lesions or metastasis. Such effects can be apparent in a significant minority of subjects (e.g., at least about 20% or more typically at least about 40%) or in a majority of subjects, which are observed in many clinical treatment situations, e.g., cancer treatments where a treatment can cause a disease to go into remission and the remission can be permanent or exist for some period of time, e.g. about 1-3 months, about 4-6 months, about a year or about two to five years. The treatments described herein can generate similar effects, which are referred to as preventing or prevention of the condition or the symptom. Thus, "prevent" or "prevention" is not restricted to keeping the occurrence of an event from ever happening or to preclude the possibility of the event from happening in all or a majority of all subjects, although such outcomes may occur.

"Subject to developing" as used herein refers to the likelihood of a subject, based upon risk factors predicated on pre-existing health status, family history, behavior, genetic marker(s) or biochemical marker(s) that have been derived from a population of subjects to which the subject belongs, to suffer from a condition so identified. Thus, a subject, such as a human, who is subject to developing a hyperproliferation condition refers to a human subject with a generally recognized statistically greater likelihood of developing the hyperproliferation condition as a result of the human subject possessing one or more of the known risk factors for the hyperproliferation condition. Individuals diagnosed with a precancer, e.g., cervical dysplasia or prostatic intraepithelial neoplasia are considered to be subject to developing cervical cancer or prostate cancer.

A "surface-active agent" (surfactant) means a substance, which, at low concentrations, interacts between the surfaces of a solid and fluid in which the solid is insoluble or sparingly soluble. The fluid may be a liquid excipient present in a suspension formulation comprising a solid state form of an active pharmaceutical ingredient, such as a crystalline Form I or Form III of Compound I, the liquid excipient and the surface active agent that acts to improve suspendability. Alternatively, the surface active agent may be present in an oral solid dosage form comprising a polymorph of Compound 1 (e.g., crystalline Form I or Form III), the amorphous form of Compound 1 or a mixture thereof and the surface active agent, which acts to improve dissolution rate of the active pharmaceutical ingredient in the gastric fluid. Surface-active agents are amphipathic in structure having both polar (hydrophilic) and non-polar (hydrophobic) regions in the same molecule. Examples of surface active agents used in the formulation arts are given in Corrigan, O. I.; Healy, A. M. "Surfactants in Pharmaceutical Products and Systems" in *Encyclopedia of Pharmaceutical Technology* $2^{nd}$ ed. Taylor and Francis, 2006, pp 3583-3596.

A "suspension" as used here unless specified or implied by context means a solid state form of Compound 1 suspended, usually as a finely divided (e.g., micronized) solid, in a liquid carrier (vehicle) at a time prior to administration of the suspension. The suspension may be either ready to use or a dry powder reconstituted as a suspension dosage form just prior to use. Suspensions are used when Compound 1 is insoluble or poorly soluble in a desired diluent or vehicle. Suspensions typically include a suspending or flocculating agent, a wetting agent, if the suspending or flocculating agent that is present does not already serve this purpose, a buffering agent and a preservative. In a colloidal suspension, the Compound 1 particles are typically less than about 1 μm in size. In a coarse suspension, they are larger than about 1 μm. The practical upper limit for individual suspendable Compound 1 particles in coarse suspensions is about 50 μm to 75 μm although some proportion of particles up to 200 μm may be suitable dependent upon the syringeability of the suspension. Design considerations for developing a suspension for oral or parenteral administration are given in Akers, et al. *J. Parenteral Sci. Tech.* 1987 41:88-96; Nash, R A "Suspensions" in Encyclopedia of Pharmaceutical Technology $2^{nd}$ ed. Taylor and Francis, 2006, pp 3597-3610 (which is hereby incorporated herein by reference with specificity into the present application).

Characterization and Identification Methods for Solid State Forms

Morphology

Crystal morphology refers to the symmetry in a crystal as exhibited by its crystal faces due to the ordered internal arrangement of atoms in the crystal structure. Crystal morphology of a particular crystalline form is typically described by the crystalline form's crystal system, namely, triclinic, monoclinic, orthorhombic, tetragonal, hexagonal or isometric. Crystal morphology may be determined by observation, for example by microscopic evaluation under at least about 2×, 10× or 100× magnification using normal or polarized light. Crystals with crystallographically distinct axes will interact with light in a manner that is dependent upon the orientation of the crystalline lattice with respect to the incident light angle and are referred to as anisotropic crystals. Thus, when light enters a non-equivalent axis, it is refracted into two rays each polarized with the vibration directions oriented at right angles to one another, and traveling at different velocities. This phenomenon is termed birefringence and is exhibited to a greater or lesser degree in all anisotropic crystals. When polarized light is vibrating in a plane of the birefringent crystal that is parallel to the direction of the polarizer there will be no contribution from light passing through the analyzer (because the single direction of light vibration is parallel to the polarizer) resulting in the crystal being very dark and almost invisible (i.e., extinction). Thus, a birefringent crystal will exhibit extinction when rotated under polarized light. Since many organic compounds in crystalline form are birefringent their crystals will exhibit extinction provided that are well formed (i.e. are not extensively fragmented or otherwise irregular in shape or contain significant number of crystal defects). Therefore, a solid state form of Compound 1 that does not exhibit extinction under examination with cross-polarized light does not necessarily mean that the solid state form is not crystalline.

Crystal morphology can also be determined experimentally from single crystal X-ray data or computationally form X-ray powder diffraction data by methods disclosed herein.

X-ray Powder Diffraction—

X-Ray powder diffraction (XRPD) is typically used to characterize or identify crystalline compounds (see, e.g., U.S. Pharmacopoeia, volume 23, 1995, method 941, p 1843-1845, U.S.P. Pharmacopeia Convention, Inc., Rockville, Md.; Stout et al, X-Ray Structure Determination; A Practical Guide, MacMillan Co., New York, N.Y. 1968). When an X-ray beam interacts with a crystalline form a diffraction pattern is typically produced characterized by sequences of intensity maximums at positions that depend on lattice features of the crystalline form. Thus, the positions and the relative intensity of the XRPD lines are indicative of a particular crystalline form that provide a "fingerprint" that is often specific for a given crystalline form, although weak or very weak diffraction peaks may not always appear in replicate diffraction patterns obtained from successive batches of crystals. This is particularly the case if other crystalline forms are present in the sample in appreciable amounts, e.g., when a polymorph or pseudopolymorph form has become partially hydrated, dehydrated, desolvated or heated to give a significant amount of another polymorph or pseudopolymorph form.

Furthermore, the relative intensities of bands, particularly at low angle X-ray incidence values (low 2θ), may vary due to preferred orientation effects arising from differences in, e.g., crystal habit, particle size and other conditions of measurement. Thus, the relative intensities of the diffraction peaks may not always be conclusively diagnostic of the crystal form in question. Instead, one typically looks to the relative positioning of the peaks coupled with their amplitude in order to determine that a crystalline form of Compound 1 is one of the forms described herein. Broad XRPD peaks, which may consist of two or more individual peaks located closely together, may be produced by amorphous components, disordered crystalline forms or parasitic scatter from the main beam. Broad peaks for different samples of the same solid state form are generally located within about 0.3-1 degree 2θ. Sharp isolated XRPD peaks for different samples of the same solid state form are usually found for normal resolution data within about 0.1 2θ degrees or occasionally within about 0.2 2θ degrees on successive XRPD analyses, if they are conducted within the same lab under reproducible environmental conditions following the same protocol. Thus, when a sharp isolated XRPD peak at a given position is identified as being located at, e.g., about 13.5 or 13.45 this means that the peak is at 13.5±0.1 or 13.45±0.10. When a broad XRPD peak at a given position is identified as being located at about a given degree 2θ value, this means that the peak is at that degree 2θ value±0.3.

Under reproducible intra-lab conditions using the same instrument and protocol to obtain the XRPD patterns, the differences in XRPD peak locations and intensities obtained from successive XRPD analyses on different samples of the same solid state form having the same degree of crystallinity are due primarily to differences in sample preparation or the purity of the sample.

It is usually not necessary to rely on all bands that one observes in a purified polymorph or pseudopolymorph sample disclosed herein, since even a single band may be diagnostic of a given polymorph or pseudopolymorph form of Compound 1. Rather, identification will typically focus on band position and general pattern, particularly on the selection of bands unique to the various polymorph and pseudopolymorph forms. Typically, an individual polymorph or pseudopolymorph form of Compound 1 is characterized by reference to the 2, 3 or 4 most intense or the 2, 3 or 4 most reproducible peaks XRPD peaks and optionally by reference to one or two other physical or analytical properties such as melting point, one or more thermal transitions observed in differential thermal analysis (DTA) and/or differential scanning calorimetry (DSC), one or more absorption peaks observed in infrared or Raman spectroscopy and/or intrinsic dissolution rate (DR) data in an aqueous or other solvent system. Standardized methods for obtaining XRPD, DTA, DSC, DR, etc. data have been described for example in U.S. Pharmacopoeia, volume 23, 1995, United States Pharmacopeial Convention, Inc., Rockville, Md., pp 2292-2296 and 2359-2765 (incorporated herein by reference).

One method to identify a known polymorph or pseudopolymorph form within a suspected solid state sample, such as a solid state formulation comprising the known polymorph or pseudopolymorph form, involves obtaining one or more XRPD patterns from sample(s) containing the known polymorph or pseudopolymorph form, which are then compared with the XRPD patterns of the suspected solid state sample using, for example, a heuristic clustering analysis method as described for example in US Pat. Appl. No. 2004/0103130 (incorporated herein by reference particularly at paragraphs 0067-0078 and paragraphs 0086-0115 inclusive). Heuristic clustering analysis may also be used for quantitative analysis of samples containing either mixed crystalline phases (e.g., mixture of two or more polymorph forms) or mixed crystalline and disordered phases (e.g. mixture of a polymorph and amorphous forms) as described for example in US Pat. Appl. No. 2004/0103130 (incorporated herein by reference, particularly at paragraphs 0116-0130 inclusive).

Comparisons of atomic pairwise distribution functions (PDFs) derived from XRPD patterns may also be used to identify a known polymorph or pseudopolymorph in a suspected solid state sample, such as a solid state formulation comprising the known polymorph or pseudopolymorph form. By definition, the PDF is the sine Fourier transform of the experimentally determined reduced structure factor obtained from a measured XRPD pattern and is obtained, for example, according to the procedure given in Peterson, et al. "Improved measures of quality for the atomic pairwise distribution function" *J. Acta Cryst*. Vol. 36, pp. 53-64 (2003). The PDF is an atomic density correlation function that describes the solid state form by providing interatomic distances as given by the PDF peak positions and the number of atoms having a specific interatomic distance as given by peak intensity. Thus, if two crystalline forms are of the same molecule with the same molecular packing, their PDFs will be essentially the same. To determine if two PDFs derived from, for example, a known polymorph form or pseudopolymorph form and a solid state formulation suspected of containing these crystalline forms are essentially identical, the PDFs are compared by, for example, the method described in US Pat. Appl. No. 2007/0243620 (incorporated herein by reference).

If high resolution XRPD pattern(s) of an essentially pure polymorph or pseudopolymorph may be obtained, then unit cell parameters (as described in the section on single crystal X-ray analysis) may be determined for the crystalline form by an indexing method as, for example, in US Pat. Appl. No. 2007/0270397 (incorporated herein by reference). For a pseudopolymorph, if an isostructural crystalline form (i.e., a reference crystalline form), such as an isostructural anhydrate, which may be derived from dehydration and/or desolvation of the pseudopolymorph, may be obtained, then comparison of the unit cell volume of the isostructural crystalline form with the unit cell volume determined from high resolution XRPD pattern(s) may allow determination of the stoichiometry of the pseudopolymorph (i.e., number of water or solvent molecules per molecule of Compound 1). In such applications, the unit cell parameters for the reference isostructural crystalline form may be obtained from single crystal X-ray analysis or derived from indexing of high resolution XRPD data for this reference form.

An XRPD pattern may be described by "Prominent Peaks", as is typically done for samples with only one XRPD pattern and limited other means to evaluate whether the sample provides a good approximation of the powder average. Prominent peaks are selected from observed peaks by identifying preferably non-overlapping, low-angle peaks, with strong intensity.

Single Crystal X-Ray Analysis—

Single X-ray crystallography identifies the smallest volume element, known as the unit cell that by repetition in three dimensions describes the crystalline form. The dimensions of the unit cell is described by three axes, a, b and c, and the angles between them α, β and γ. X-ray reflections from a series of planes are defined by the orientation and interplanar spacings of these planes using three integers h, k and l called indices. A given set of planes with indices h, k, l cut the a-axis of the unit cell in h sections, the b-axis in k sections and the c-axis in l sections. A zero value for an indicia means the planes are parallel to the corresponding axis.

Single crystal X-ray parameters that characterize the crystalline form will typically include the crystal system, space group, unit cell dimensions, Z value (number of molecules per unit cell) and unit cell volume. Typically, calculated density and ranges for indices h, k, l are also used for characterization. Using the atomic coordinates, space group and unit cell parameters determined from the single crystal data one may simulate the XRPD pattern which may then be compared with the experimentally determined XRPD pattern to confirm the correctness of the structure solution for the unit cell.

Vibrational Siectroscory—

Diagnostic techniques that one can optionally use to characterize crystalline forms of Compound 1, such as a polymorph or pseudopolymorph form, include vibrational spectroscopy techniques such as IR and Raman, which measure the effect of incident energy on a solid state sample due to the presence of particular chemical bonds within molecules of the sample that vibrate in response to the incident energy. Since the molecules in different polymorph or pseudopolymorph forms experience different intermolecular forces due to variations in conformational or environmental factors, perturbations of those vibrations occur that leads to differences in spectra due to differences in frequency and intensity of some modes of vibration. Because polymorphs and pseudopolymorph form may possess different IR and Raman characteristics from each other, IR and Raman spectrum provide complementary information and either may provide a fingerprint for identification of a particular polymorph. [see, Anderton, C. *European Pharmaceutical Review,* 9:68-74 (2004)].

Raman is capable of determining polymorph or pseudopolymorph identity and/or quantification in a complex matrix, distinguishing between amorphous and crystalline forms or differentiating between multiple polymorphic and pseudo polymorphic forms of Compound 1 [for example, see Pratiwia, D., et al. "Quantitative analysis of polymorphic mixtures of ranitidine hydrochloride by Raman spectroscopy and principal components analysis" *Eur. J. Pharm. Biopharm.* 54(3), 337-341 (2002)]. For identifying a polymorph or pseudopolymorph form in a solid formulation such as a tablet, powder samples of these pure crystalline forms of Compound 1 and excipients are gently compacted and scanned with Raman microscopy to build up a library of formulation component spectra. A partial least squares (PLS) model and multivariate classification are then used to analyze Raman mapping data obtained from sectioned tablets having low API content (about 0.5% w/w). Multivariate classification allows polymorph assignments to be made on individual microscopic pixels of Compound 1 identified in the data. By testing data from separate sets of tablets containing each specific crystalline form, specific form recognition may be demonstrated at about 0.5% w/w. For tablets containing a mixture of crystalline forms, recognition of about 10% polymorphic or pseudopolymorphic impurity of Compound 1 (representing an absolute detection limit of about 0.05% w/w), is possible.

For determining polymorph or pseudopolymorph identity or quantification for a crystalline form of Compound 1 within a complex matrix such as a solid formulation using the above vibrational spectroscopy methods, the technique of attenuated total reflectance (ATF) is sometimes used (for an example see Salari, H., et al. "Application of attenuated total reflectance FTIR spectroscopy to the analysis of mixtures of pharmaceutical polymorphs" *International Journal of Pharmaceutics* 163 (1): 157-166 (1998)].

Another technique for identification or quantification of a crystalline form is Diffuse Reflectance Infrared Fourier Transform Spectroscopy (DRIFTS) (for an example see Tantishaiyakul, V., et al. "Use of DRIFTS and PLS for the Determination of Polymorphs of Piroxicam alone and in combination with pharmaceutical excipients: A Technical Note" *AAPS Pharm Sci Tech* 9(1) 95-99 (2008)]. It is well known that particle size is a key variable in diffuse reflectance measurements, since large particles will result in scattering of the energy leading to the shift of the spectrum baseline and the broadening of IR bands. To conduct DRIFTS the sample containing solid state Compound 1 is prepared, by grinding or passing it through a sieve, to obtain uniform particles with the later preferred since the possibility of transformation of a metastable polymorph or pseudopolymorph form to another crystalline form is avoided.

In yet another technique, near-infrared (NIR) spectroscopy may also be used in identification or quantitative analysis of a crystalline form, such as a polymorphs or pseudo polymorph form (e.g. hydrate) of Compound 1 in mixture of solid state forms or identification of a polymorph or pseudopolymorph form in a solid formulation such as a tablet containing the polymorph or pseudopolymorph form of Compound 1.

Extensive overlap of IR or Raman bands from different crystalline forms of Compound 1 examined by the various vibration spectroscopy methods described herein may sometimes occur so that quantification requires deconvolution methods to extract information for each individual component. Such deconvolution methods include partial least squares regression, principle component analysis or other methodologies [for examples, see Reich, G. "Near-infrared spectroscopy and imaging: Basic principles and pharmaceutical applications" *Adv. Drug Deliv. Rev.* 57: 1109-43 (2005)].

Solid State Nuclear Magnetic Resonance (SS-NMR)—

Diagnostic techniques that one can optionally use to characterize polymorphs of Compound I include solid state NMR techniques [for examples see Tishmack, P. A., et al. "Solid-State Nuclear Magnetic Resonance Spectroscopy: Pharmaceutical Applications," *J. Pharm. Sci.* 92 (3): 441-474 (2003)]. These techniques offer the advantage of being non-destructive and noninvasive. SS-NMR spectroscopy is sometimes suitable for testing drug formulations, such as those comprising Compound 1, because the NMR resonances for most pharmaceutical excipients occur in a narrow range of the NMR spectrum. Thus, it is typically easy to distinguish excipients from Compound 1 NMR resonances. Spectral subtraction can even be used to eliminate interfering excipient peaks that are present from the spectrum.

SS-NMR usefulness in characterizing a particular polymorph or pseudopolymorph form of Compound 1 is due to different numbers of crystallographically non-equivalent sites in the unit cells of these crystalline forms, and its sensitivity to changes in the local chemical environment where slight changes in bond lengths, bond angles, interactions with neighboring molecules or, in the case of pseudo polymorphs, different hydration or salvation levels, can effect the SS-NMR signals relative to the solution spectrum.

For amorphous materials, SS-NMR spectroscopy may be used to examine the degree of disorder because various processing techniques (e.g., lyophilization, spray drying, melt-quench, cryomilling) can vary the overall degree of disorder in the sample or result in a change in polymorph form. For a less stable (i.e., metastable) polymorph or pseudopolymorph form of Compound 1, the relative instability of that crystalline form could be caused by the overall greater molecular mobility of Compound 1 in the solid state sample.

Sometimes, the same polymorphic or pseudopolymorphic form of a compound obtained from different lots may exhibit different physiochemical properties such as stability and dissolution rate, which could be caused by the degree of crystallinity in the sample. The presence of defect sites or less crystalline domains in the solid state sample causing a loss of degree of crystallinity sometimes may not be observed in X-ray powder diffraction. This is often not the case with SS-NMR spectroscopy, since these sites or domains provide another avenue for the relaxation process of the spin states in the solid state sample.

SS-NMR may also be applied to analyzing solid formulations comprising Compound 1 and thus may be useful for detecting different solid state forms of Compound 1 in the presence of excipients. For detecting amorphous Compound 1 the detection limit for SS-NMR is sometimes about 10-20%, depending on the relative location of the amorphous and crystalline Form peaks in the spectrum, because amorphous peaks generally are very broad. This is about the same detection limit for XRPD.

SS-NMR spectroscopy is suitable for testing drug formulations because the NMR resonances for most pharmaceutical excipients occur in a narrow range of the NMR spectrum. Thus, distinguishing NMR resonances of Compound 1 from excipients in a formulation containing a particular polymorph or pseudopolymorph form of Compound 1 is typically possible. If there are interfering excipient peaks in the spectrum, spectral subtraction may also be used to eliminate or reduce this interference.

For identification of a particular crystalline form of Compound 1 within a formulation, SSNMR is sometimes superior to XRPD, since NMR peaks associated with Compound 1 may be found that are not obscured by peaks from excipients of the formulation. This may not be the case in XRPD since many diffraction lines may overlap, thus limiting the detection of small amounts of a polymorph or pseudopolymorph form of Compound 1. Without interfering diffraction lines a detection limit of about 10%, and sometimes to about 5%, in XRPD for a Compound 1 polymorph or pseudopolymorph may be obtained, while SSNMR may attain detection limits down to about 0.5%. In addition, because NMR spectroscopy is inherently a quantitative technique (i.e., signal intensity is relative to the number of nuclear sites at that specific resonance frequency), SSNMR spectroscopy may allow one to determine the contribution of crystalline forms of Compound 1, or of crystalline and amorphous Compound 1, in a mixture of such forms.

Thermal Analysis Procedures—

Diagnostic techniques that one can optionally use to characterize polymorphs of Compound 1 include differential thermal analysis (DTA), differential scanning calorimetry (DSC), thermo-gravimetric analysis (TGA) and melting point measurements.

DTA and DSC measures thermal transition temperatures at which a crystalline form absorbs or releases heat when its crystal structure changes or it melts. TGA is used to measure thermal stability and the fraction of volatile components of a sample by monitoring the weight change as the sample is heated. If infrared spectroscopy is conducted on the volatile components outgassed during TGA analysis of a pseudopolymorph (TGA-IR), then the molecular composition of the polymorph may be discerned. These techniques are thus useful for characterizing solid state forms existing as solvates and/or hydrates.

DTA involves heating a test sample of a solid state form of Compound 1 and an inert reference under identical conditions while recording any temperature difference between the sample and reference. This differential temperature is plotted against temperature, and changes in the test sample that leads to absorption or liberation of heat can thus be determined relative to the inert sample.

DSC measures the energy needed to establish a nearly zero temperature difference between a sample and an inert reference as they are subjected to identical heating regimes. The energy required to do this is a measure of the enthalpy or heat capacity changes in the sample relative to the reference.

Thermal transition temperatures typically occur within about 2° C. on successive analyses using a temperature scan rate of 10° C./min and occur within about 1 degree depending on the temperature scan rate used (with slower scan rates such as 5° C./min or 1° C./min providing greater precision). When it is stated that a compound has a DTA transition at a given value, it means that the DTA transition will be within ±2° C. Different crystalline forms including polymorph or pseudopolymorph forms may be identified, at least in part, based on their different transition temperature profiles in their DTA thermographs.

Thermal analysis is usually conducted at a temperature scan rate of 10° C./min. Lower scan rates such as 5° C./min or 1° C./min may be used if overlap of temperature transitions is suspected. Thus, a suspected transition due to a change in polymorph form to a different, more stable polymorph prior to complete melting of the sample may be discerned using a slower scan rate. A transition during thermal analysis of a kinetically formed polymorph to a thermodynamically more stable polymorph prior to complete melting may be avoided using a faster scan rate that does not allow time for the transition to occur.

Data Acquisition for Characterization and Identification Methods

Data provided in the Figures, Tables and Examples were obtained using the following methods and instrumentation.

X-Ray Powder Diffraction—

XRPD patterns were obtained using a PANalytical X'Pert Pro diffractometer. An incident beam of Cu Kα radiation was produced using an Optix long, fine-focus source. An elliptically graded multilayer mirror was used to focus the Cu Kα X-rays of the source through the specimen and onto the detector. Data were collected and analyzed using X'Pert Pro Data Collector software (v. 2.2b). Prior to the analysis, a silicon specimen (NIST SRM 640c) was analyzed to verify the Si 111 peak position. The specimen was sandwiched between 3 μm thick films, analyzed in transmission geometry, and rotated to optimize orientation statistics. A beam-stop and a helium atmosphere were used to minimize the background generated by air scattering. Soller slits were used for the incident and diffracted beams to minimize axial divergence. Diffraction patterns were collected using a scanning position-sensitive detector (X'Celerator) located 240 mm from the specimen.

XRPD patterns were collected using an Inel XRG-3000 diffractometer equipped with a curved position sensitive detector with a 2θ range of 120°. An incident beam of Cu Kα radiation (40 kV, 30 mA) was used to collect data in real time at a resolution of 0.03° 2θ. Prior to the analysis, a silicon standard (NIST SRM 640c) was analyzed to verify the Si 111 peak position. Samples were prepared for analysis by packing them into thin-walled glass capillaries. Each capillary was mounted onto a goniometer head and rotated during data acquisition. The monochromator slit was set at 5 mm by 160 μm, and the samples were analyzed for 5 minutes.

XRPD patterns were also obtained on a Shimadzu WRD-6000 X-ray powder diffractometer with Cu Kα radiation. The solid state samples were prepared for analysis by placement in an aluminum holder with a silicon insert. The instrument was equipped with a long fine focus X-ray tube. The tube voltage and amperage were set to 40 kV and 40 mA, respectively. The divergence and scattering slits were set at 1° and the receiving slit was set at 0.15 mm. Prior to the analysis, a silicon standard (NIST SRM 640c) was analyzed to verify the Si 111 peak position. Diffraction radiation was detected by a sodium iodide scintillation detector. A θ-2θ continuous scan at 3°/min (0.4 sec/0.020 step) from 2.5 to 40° 2θ was used.

X-ray diffraction patterns presented herein are accompanied by labeled peaks and tables with peak lists. Reported peak data, under most circumstances, is within the range of up to about 30° 2θ. As previously discussed data will be instrument dependent and third party measurements on independently prepared samples on different instruments may lead to variability that is greater than ±0.1° 2θ. In addition, for technical reasons, different rounding algorithms were used to round each peak to the nearest 0.1° or 0.01° 2θ, depending upon the instrument used to collect the data and/or the inherent peak resolution.

The location of reported peaks along the x-axis (degree 2θ) in the figures and the tables were automatically determined using PATTERNMATCH™ 2.4.0 software and rounded to one or two significant figures after the decimal point based upon the above criteria. Peak position variability is given to within ±0.1° 2θ based upon recommendations outlined in the USP discussion of variability in X-ray powder diffraction given in United States Pharmacopeia, USP 31, NF 26, Vol. 1, pg. 374. For d-space listings, the wavelength used to calculate d-spacings was 1.541874 Å, a weighted average of the Cu—K$_{α1}$ and Cu—K$_{α2}$ wavelengths [*Phys. Rev. A* 56(6) 4554-4568 (1997)]. Variability associated with d-spacing estimates was calculated from the USP recommendation at each d-spacing and is provided in the respective data tables.

Differential Scanning Calorimetry (DSC)—

DSC was performed using a TA Instruments Q2000 differential scanning calorimeter. Temperature calibration was performed using NIST traceable indium metal. The sample was placed into an aluminum DSC pan, and the weight was accurately recorded. The pan was covered with a lid perforated with a laser pinhole, and the lid was crimped. A weighed, crimped aluminum pan was placed on the reference side of the cell. The sample cell was equilibrated at 25° C. and heated under a nitrogen purge at a rate of 10° C./minute, up to a final temperature of 25° C. Reported temperatures are at the transition maxima.

Differential Thermal Analysis (DTA)—

DTA and TGA were performed simultaneously using a Seiko SSC 5200 TG/DTA instrument. Temperature calibration was performed using NIST traceable indium metal. The sample was placed into an aluminum pan and loosely covered with a lid and the weight accurately recorded. The sample cell was equilibrated at 25° C. and then heated under a nitrogen purge at a rate of 10° C./minute, up to a final temperature of 250° C. Reported temperatures are at the transition maxima.

Thermogravimetric Analysis (TGA)—

TGA was performed using a TA Instruments Q5000 IR thermogravimetric analyzer. Temperature calibration was performed using nickel and ALUMEL™. Each sample was placed in an aluminum/or/platinum pan. The pan was hermetically sealed with a lid that was opened using a punching mechanism just before being inserted into the TG furnace. The furnace was heated under nitrogen at a rate of 10° C./minute to a final temperature of 350° C.

FT-Raman Spectroscopy—

Raman spectra were acquired on a Nexus 670 FT-Raman accessory module interfaced to a Nexus 670 FT-IR spectrophotometer (Thermo Nicolet) equipped with an indium gallium arsenide (InGaAs) detector. Wavelength verification was performed using sulfur and cyclohexane. Each sample was prepared for analysis by placing the sample into a glass tube and positioning the tube in a gold-coated tube holder. Approximately 0.5 W of Nd:YVO$_4$ laser power (1064 nm excitation wavelength) was used to irradiate the sample. Each spectrum represents 256 co-added scans collected at a spectral resolution of 4 cm$^{-1}$.

Karl Fischer Analysis—

Coulometric Karl Fischer (KF) analysis for water determination was performed using a Mettler Toledo DL39 KF titrator. A blank titration was carried out prior to analysis. The sample was prepared under a dry nitrogen atmosphere, and dissolved in approximately 1 mL dry HYDRANAL-COULOMAT AD™ in a pre-dried vial. The entire solution was added to the KF coulometer through a septum and mixed for 10 seconds. The sample was then titrated by means of a generator electrode, which produces iodine by electrochemical oxidation: 2 I$^-$→I$_2$+2e$^-$. Two replicates were obtained to ensure reproducibility.

Formulations—

Formulations comprising Compound 1 as the active pharmaceutical ingredient will have a significant percentage of Compound 1 in one or more of its solid state forms, typically in one or two solid state forms. Exemplary formulations contain at least about 60% or usually at least about 90% of Compound 1 in one solid state form. Formulations will usually comprise one or more given solid state forms of Compound 1, substantially free of other solid state forms, and one or more, typically 1, 2, 3 or 4 excipients or carriers. Other formulations can contain Compound 1 in one or more solid state forms, typically one or two. Other formulations are generally solids, precipitates, gels, suspensions and colloids that contain one or more solid state forms of Compound 1, such as the amorphous form of Compound 1, crystalline Form I or crystalline Form III of Compound 1 or a mixture thereof. Preferred oral unit dosages for human use will contain about 2 mg, 5 mg, 10 mg, 15 mg, 20 mg or 40 mg of a solid state form of Compound 1 per unit dose.

While it is possible to administer Compound 1 in its solid state as a pure compound to a subject, it is usually presented as a solid formulation essentially free of liquid or less frequently a solid suspension. Formulations will typically be used to prepare unit dosages, e.g., tablets, capsules or lozenges for oral, buccal or sublingual administration, that usually comprise about 0.1-500 mg, typically about 0.5-100, or about 1-100 mg (e.g., about 0.1, about 0.25, about 0.5, about 1, about 5, about 10, about 20, about 100 mg) of a formulation containing a solid state form of Compound 1 such as amorphous Compound 1, crystalline Form I or crystalline Form III of Compound 1. Alternatively, embodiments include a product for parenteral (e.g., subcutaneous, subdermal, intravenous, intramuscular, intraperitoneal or aerosol) administration made by the process of contacting a solid state form of Compound 1, such as amorphous Compound 1, crystalline Form I, or crystalline Form III of Compound 1, with a liquid excipient, e.g., any one, two, three or more of PEG 100, PEG 200, PEG 300, PEG 400, propylene glycol, benzyl benzoate, benzyl alcohol or ethanol, and optionally sterilizing the solution and optionally dispensing the solution into vials or ampoules (typically amber glass), which may be single-use or multi-use and optionally storing the formulation at reduced temperature (about 0-12° C., or about 2-10° C.). Such products for parenteral administration typically comprise Compound 1 at a concentration of about 0.1-100 mg/mL, usually at about 1-100 mg/mL or about 10-100 mg/mL, and optionally containing one or more of a salt, buffer or bacteriostat or preservative (e.g., NaCl, BHA, BHT or EDTA). Sometimes a surface active agent is used to affect a suspension or is incorporated into an oral solid dosage form to assist dissolution of the solid state form of Compound 1 into the gastric tract. In general, formulations for oral administration are preferred for human therapeutic applications.

Surface active agents used in a suspension or a solid form of Compound 1 in a liquid excipient(s) include nonionic, cationic and anionic surfactants. Examples of preferred surfactants include, but are not limited to, sodium lauryl sulfate, sodium dodecyl sulfate, polysorbate 40 and polysorbate 80.

In one embodiment, sodium lauryl sulfate is used as a surface active agent in a unit dosage form, such as a tablet or a capsule, for oral administration in treatment of a condition disclosed herein wherein the formulation comprises crystalline Form I or crystalline Form III of Compound 1 essentially free of other solid state forms of Compound 1 and the surface active agent, optionally comprising one or more additional excipients, typically 1, 2 or 3 additional excipients.

Examples of other excipients used in the preparation of formulations comprising a solid state form of Compound 1 (e.g., crystalline Form I or crystalline Form III), by way of illustration and not limitation, are given in Nema, S., et al. *PDA J. Pharm. Sci. Tech.* 1997, 51:166-171; Strickley, R. G. *Pharm. Res.* 2004, 21:201-230; Powell, M. F., et al. *PDA J. Pharm. Sci. Tech* 1998, 52:238-311; Akers, M. J. in "Drug Delivery: Parenteral Route" Encyclopedia of Pharmaceutical Technology, Informa Healthcare, USA, 2007, pp 1266-1278.

Micronization—

To improve dissolution rate of a crystalline form of Compound 1 in a formulation comprising at least one crystalline form of Compound 1 and one or more pharmaceutically acceptable excipients in a solid dosage form or to affect suspendability in a suspension for oral or parenteral administration comprising a crystalline form of Compound 1 and a liquid excipient(s), the crystalline form may be milled to an mean volume weighted particle size (Dv,50) or average diameter of about 0.01-200 μm, or about 0.1-100 μm or about 3-50 μm. Mean volume weighted particle size (Dv, 50) or average diameter for milled crystalline Compound 1 may thus be relatively small, e.g., about 0.03-2.0 μm or about 0.1-1.0 μm, or somewhat larger, e.g., about 3-100 μm, about 5-75 μm or about 10-30 μm. Milled crystalline Compound 1 is suitable for preparing solid and suspension formulations intended for oral or parenteral administration to a subject. Mean volume weighted particle size or average diameter include a range between about 0.01 and about 500 microns in 0.05 micron or in 0.1 micron, e.g., mean volume weighted particle size or average diameter of about 0.05, about 0.1, about 0.5, about 1.0, about 1.5, about 2.0, about 2.5, about 3.0, about 3.5, about 4.0, about 4.5, about 5.0, about 5.5, about 6, about 7, about 8, about 9, about 10, about 15, about 20, about 25, about 30, about 35, about 40, about 50, about 60, about 75, about 85, about 100, about 120, etc. microns). Preferably, mean volume weighted particle size (Dv,50) or average diameter are about 5, about 10, about 15 or about 20 micron. The particle size (Dv, 90) typically is about 5 micron, about 10, about 15, about 20, about 25 or about 30 micron. Preferred particle size has (Dv, 90) of ≦10 microns or about micron (Dv, 90) of ≦6.8 microns.

As used herein, reference to a mean volume weighted particle size or average diameter means that the material, e.g., crystalline compound 1, an excipient(s) or a composition that comprises both, is ground, milled, sieved or otherwise treated so as to comprise the specified particle size. It is to be understood that some particles may be larger or smaller (i.e., will exist in a distribution of particle sizes), but the composition or the crystalline form of Compound 1 (e.g. crystalline Form I or crystalline Form III) will comprise a significant proportion of the material with the specified size or within an acceptable range of the specified size. Micronization methods include milling by ball mills, pin mills, jet mills (e.g., fluid energy jet mills) and grinding, sieving and precipitation of a compound(s) from a solution, see, e.g., U.S. Pat. Nos. 4,919, 341, 5,202,129, 5,271,944, 5,424,077 and 5455049, which are specifically incorporated herein by reference herein). Particle size is determined by, e.g., transmission electron microscopy, scanning electron microscopy, light microscopy, X-ray diffractometry and light scattering methods or Coulter counter analysis (see, for example, "Characterization of Bulk Solids" D. McGlinchey, Ed., Blackwell Publishing, 2005).

Thus, crystalline Compound 1 may comprise or consist essentially of a powder that contains one, two or more of these mean volume weighted particle sizes or average diameter particle sizes and the powder may be contacted with a solid excipient(s), which can be mixed and optionally compressed or formed into a desired shape. Alternatively, crystalline Compound 1 formed into a powder a described above is contacted with a liquid excipient(s) to prepare a liquid formulation or a liquid composition that is incorporated into a solid formulation or suspension. Suitable micronized formulations thus include aqueous or oily suspensions of crystalline Compound 1.

Hyperproliferation Conditions—

Hyperproliferation conditions that can be treated with crystalline Compound 1, for example, an anhydrate crystalline form such as Form III, or amorphous Compound 1 include cancers, precancers and other hyperproliferation conditions comprising carcinomas, sarcomas, adenomas, dysplasias, blastomas, papillomas, naevus, pre-malignant tumors, benign tumors or malignant tumors including solid tumors and disseminated tumors such as one associated with or arising from prostate, lung, breast, ovary, skin, stomach, intestine, pancreas, neck, larynx, esophagus, throat, tongue, lip, oral cavity, oral mucosa, salivary gland, testes, liver, parotid, biliary tract, colon, rectum, cervix, uterus, vagina, pelvis, endometrium, kidney, bladder, central nervous system, glial cell, astrocyte, squamous cell, blood, bone marrow, muscle or thyroid cells or tissue.

One category of benign tumors encompasses functional tumors so named because they have functional effects on the affected tissue. For example, functional tumors of endocrine tissue, referred to as adenomas, overproduce certain hormones.

Another category of benign tumors that can be treated with crystalline Compound 1, for example, an anhydrate crystalline form such as Form III, or amorphous Compound 1 includes papillomas, which refer to benign epithelial tumors growing exophytically (outwardly projecting) in finger-like fronds, and naevus. Papillomas include Larynx papilloma, Choroid plexus papilloma, skin papilloma, squamous cell papilloma and transitional cell papilloma (also known as bladder papilloma).

Other benign tumors that can be treated with crystalline Compound 1, for example, an anhydrate crystalline form such as Form III, or amorphous Compound 1 are cystadenoma (or "cystoma"), which is a type of cystic adenoma derived from glandular tissue where secretions are retained and accumulate in cysts and include mucinous cystadenoma (produced by ovarian epithelial cells), papillary cystadenoma (any tumor that produces patterns that are both papillary and cystic), serous cystadenoma and thecomas, which are benign ovarian neoplasms that are typically estrogen-producing.

Non-malignant hyperproliferative conditions of the skin that can be treated with crystalline Compound 1, for example, an anhydrate crystalline form such as Form III, or amorphous Compound 1 include seborrheic keratosis, toxic eczema, allergic eczema, atopic dermatitis, ichthyosis, and psoriasis.

Benign prostate hyperplasia (BPH), arteriovenous malformations, heterotrophic bone formation, hyperplasia of the breast, focal epithelial hyperplasia, sebaceous hyperplasia and congenital adrenal hyperplasia are examples of hyperproliferation conditions that are hyperplasias that can be treated with crystalline Compound 1, for example, an anhydrate polymorphic form such as Form III, or amorphous Compound 1. Preferable treatments are for BPH.

Treatment options for BPH include crystalline Compound 1, for example, an anhydrate crystalline form such as Form III, or amorphous Compound 1 include $\alpha_1$-adrenergic receptor antagonists such as doxazosin, terazosin, alfuzosin, tamsulosin and 5α-reductase inhibitors such as finasteride and dutasteride.

Premalignant conditions or tumors that can be treated with crystalline Compound 1, for example, an anhydrate crystalline form such as Form III, or amorphous Compound 1 include colon polyps, actinic keratosis, squamous metaplasia, leukoplakia, erythroplakia, Barrett's esophagus, endometrial hyperplasia, cervix dysplasia, polycythemia rubra vera and carcinoma in situ (CIS). Preferably treated are endometrial hyperplasia and cervix displasia Prostatic interstitial neoplasia (PIN) can be treated with crystalline Compound 1, for example, an anhydrate crystalline form such as Form III, or amorphous Compound. PIN can be classified as high grade, medium grade and low grade.

Dysplasia (or heteroplasia) that can be treated with crystalline Compound 1, for example, an anhydrate crystalline form such as Form III, or amorphous Compound 1 refers to an abnormality in maturation of cells within a tissue and include myelodysplastic syndromes or dysplasia of blood-forming cells.

Malignant tumors (cancers) have properties that allow invasion and destruction of nearby tissue and spreading (metastasizing) to other parts of the body. Cancers are classified by the type of cell that resembles the tumor and, therefore, the tissue presumed to be the origin of the tumor. One general category of cancer that can be treated with crystalline Compound 1, for example, an anhydrate crystalline form such as Form III, or amorphous Compound 1 encompasses the carcinomas, which include common forms of breast, prostate, lung and colon cancer as well as basal cell carcinoma, malignant melanoma, squamous cell carcinoma, which is a malignant tumor of squamous epithelium, and also occurs in sites including the lips, mouth, esophagus, urinary bladder, prostate, lungs, vagina and cervix. Preferred treatments are for prostate and breast carcinoma. Also preferred are treatments for lung and cervix carcinoma.

Adenocarcinomas that can be treated with crystalline Compound 1, for example, an anhydrate crystalline form such as Form III, or amorphous Compound 1 represent a category of carcinomas and are of glandular origin (vide supra). To be classified as adenocarcinoma, the cells do not necessarily need to be part of a gland, as long as they have secretory properties. Adenocarcinomas sometimes begin in cells lining internal organs that have gland-like (secretory) properties and thus may arise in numerous tissues including those of breast, colon, lung, prostate, pancreas, stomach, cervix and vagina.

Carcinomas that can be treated with crystalline Compound 1, for example, an anhydrate crystalline form such as Form III, or amorphous Compound 1 include renal cell carcinoma, endometrial carcinoma and hepatocellular carcinoma (HCC), also called hepatoma. Preferred treatments are for HCC and endometrial carcinoma.

Another category of malignant tumors that also can be treated with crystalline Compound 1, for example, an anhydrate crystalline form such as Form III, or amorphous Compound 1 encompasses the neuroendocrine tumors which include insulinoma and glucagonoma.

Another category of malignant tumors that can be treated with crystalline Compound 1, for example, an anhydrate crystalline form such as Form III, or amorphous Compound 1 are sarcomas, including lymphomas, leukemias, germ cell tumors and blastomas such as glioblastoma and medulloblastoma, hepatoblastoma, nephroblastoma, neuroblastoma, osteoblastoma and retinoblastoma. Preferred treatments are for glioblastoma and osteoblastomas. Preferred leukemia and lymphoma treatments are for acute lymphoblastic leukemia (ALL), acute myelogenous leukemia (AML) and Hodgkin's disease.

The solid state forms of Compound 1 disclosed herein, e.g. an anhydrous crystalline form such as Form III, are useful to treat, prevent, slow the progression of, or ameliorate one or more symptoms of a cancer, precancer or other hyperproliferation conditions as described above.

In treating cancers or hyperproliferation conditions, the composition or formulation comprising a solid state form of Compound 1 may detectably modulate, e.g., decrease or increase, the expression or level or activity of one or more biomolecules associated with the prevention, establishment, maintenance or progression of the cancer or hyperproliferation condition. Such biomolecules include one or more of carcinoembryonic antigen, prostate specific antigen, her2/neu, Bcl-XL, bcl-2, p53, IL-1α, IL-1β, IL-6, or TNFα, GATA-3, COX-2, NFκB, IkB, an IkB kinase, e.g., IkB kinase-α, IkB kinase-β or IkB kinase-γ, NFAT, calcineurin, calmodulin, a ras protein such as H-ras or K-ras, cyclin D, cyclin E, xanthine oxidase, or their isoforms, homologs or mutant forms, which may have either reduced or enhanced biological activity(ies), and which may be detectably decreased. Biomolecules or their activity(ies) that can be detectably increased include IL-2, IFNγ, IL-12, T-bet, $O^6$-methylguanine-DNA-methyltransferase, calcineurin, calmodulin, a superoxide dismutase (e.g., Mn, Zn or Cu), a tumor suppressor protein such as the retinoblastoma protein (Rb) or CDKN2A (p16), BRCA1, BRCA2, MeCP2, MBD2, PTEN, NBR1, NBR2 or the isoforms, homologs or mutant forms, which may have either attenuated or enhanced biological activity(ies), of any of these molecules. One or more of these biomolecules may be modulated in any the cancers or conditions described herein.

In one embodiment, a decrease in circulating prostate specific antigen (PSA) or a decrease in velocity of PSA increase (e.g. decreased doubling time in the increase of serum PSA levels) is the detectable change consistent with improvement in a subject having a hyperproliferation condition wherein the condition is prostate cancer.

Dosing Protocols or Methods—

In treating any of the conditions or symptoms disclosed herein, one can continuously (daily) or intermittently administer the compositions or formulations comprising a crystalline form of Compound 1 to a subject suffering from or susceptible to the condition or symptom. In treating a hyperproliferation condition, such as prostate cancer, breast cancer or benign prostate hyperplasia or other conditions disclosed herein with a composition or formulation comprising a solid state form of Compound 1 (e.g., crystalline Form I or crystalline Form III) intermittent dosing can avoid or ameliorate some of the undesired aspects normally associated with discontinuous dosing. Such undesired aspects include failure of the patient or subject to adhere to a daily dosing regimen, tendency to acquire disease tolerance to treatment or requirement to reduce the dosages of other therapeutic agents given concomitantly due to their associated unwanted side effects or toxicities. Intermittent dosing is also employed if tachyphylaxis occurs whereupon the dosing schedule is adjusted to avoid or minimize the adverse response.

In any of the continuous (daily) or intermittent dosing protocols described herein, or in treating any of the diseases, conditions or symptoms described herein, an appropriate composition or formulation comprising a solid state form of Compound 1 (e.g. crystalline Form I or crystalline Form III) can be administered by one or more suitable routes, e.g., oral, buccal, sublingual, intramuscular (i.m.), subcutaneous (s.c.), intravenous (i.v.), intradermal, another parenteral route or by an aerosol wherein the active pharmaceutical ingredient is a solid state form of Compound 1 (e.g. crystalline Form I or crystalline Form III). The daily dose in such methods may include about 0.0025 mg/kg/day to about 5.0 mg/Kg/day. Typically, the daily dose in such administration methods will comprise about 0.01 mg/kg/day Compound 1 in solid state form (e.g., crystalline Form I or crystalline Form III), to about 3 mg/kg/day, or about 0.1 to about 1 mg/kg/day, including about 0.3 mg/kg/day to 0.5 mg/kg/day. Higher dosages, e.g., to about 60 mg/Kg/day, may also be used in some veterinary applications. In some embodiments, suspension formulations described herein comprising a crystalline form of Compound 1 are administered i.m. or s.c. Preferred unit doses contain 0.5 to 100 mg or more of one or more, typically one or two solid state forms of Compound 1 typically administered q.d, b.i.d, t.i.d or q.i.d. with 5, 15, 10 or 25 mg of a single solid state form of Compound 1 administered b.i.d. particularly preferred. Preferred unit dosage forms include those suitable for oral dosing such as tablets and capsules.

In some embodiments, such as treating a hormone sensitive or hormone associated cancer, a composition or formulation comprising a solid state form of Compound 1 is administered daily q.d. or b.i.d for 14-180 days, typically 30-90 days or until a biomarker for the hyperproliferative condition being treated indicates subsidence, lack of progression (i.e. stabilization) or remission of the disease. Dosing then resumes if the biomarker indicates resurgence or recurrence of the disease. In one such embodiment the cancer is prostate cancer and the biomarker is circulating prostate specific antigen. In another such embodiment the cancer is metastatic prostate cancer and the biomarker is the spread of disease to the bone as estimated from bone scans. In another embodiment, the cancer is breast cancer and the biomarker is tumor burden.

Dosages of Compound 1 in solid state form administered by the routes described herein and the use of combination therapies with other standard therapeutic agents or treatments could be applied essentially as described above for any of the diseases or conditions that are disclosed herein. Thus, the Compound 1 in solid state form may be administered prophylactically or therapeutically in chronic conditions or they may be administered at the time of or relatively soon after an acute event such as a pain flare associated with a condition being treated.

Dosages of Compound 1 in solid state form, routes of administration and the use of combination therapies with other standard therapeutic agents or treatments could be applied essentially as described above for cancer or hyperproliferation conditions or other conditions as disclosed herein. This, in some embodiments, the use of a solid state form of Compound 1 is optionally combined with one or more additional therapies for a cancer or precancer(s), e.g., one or more of surgery and treatment with an antiandrogen or an antiestrogen as described herein or in the cited references, an antineoplastic agent such as an alkylating agent, a nitrogen mustard, a nitrosourea, an antimetabolite or cytotoxic agent, or an analgesic such as propoxyphene napsylate, acetaminophen or codeine. Exemplary anticancer and adjunct agents include methotrexate, thioguanine, mercaptopurine, adriamycin, chlorambucil, cyclophosphamide, cisplatin, procarbazine, hydroxyurea, allopurinol, erythropoietin, G-CSF, bicalutamide, anastrozole, fludarabine phosphate and doxorubicin. Such therapies would be used essentially according to standard protocols and they would precede, be essentially concurrent with and/or follow treatment with a solid state form of Compound 1. In some embodiments, such additional therapies will be administered at the same time that a solid state form of Compound 1 is being used or within about 1 day to about 16 weeks before or after at least one round of treatment with the solid state form of Compound 1 is completed. Other exemplary therapeutic agents and their use have been described in detail, see, e.g., *Physicians Desk Reference* $54^{th}$ edition, 2000, pages 303-3250, ISBN 1-56363-330-2, Medical Economics Co., Inc., Montvale, N.J. One or more of these exemplary agents can be used in combination with a solid state form of Compound 1 to ameliorate, slow the establishment or progression of, prevent or treat any of the appropriate cancers, precancers or related conditions described herein, or any of their symptoms.

In one embodiment the cancer being treated is prostate cancer which may be androgen ablation sensitive or androgen ablation insensitive. If the cancer is androgen ablation sensitive, a solid state form of Compound 1 is administered in an appropriate formulation either alone in combination with androgen receptor antagonist such as CASODEX™ (also known as bicalutamide) optionally in combination with luteinizing hormone-releasing hormone or Leuprorelin (a gonadotropin-releasing hormone agonist), to a subject with prostate cancer who may or may not be castrated. The combination therapies may be co-administered either combined within a single dosage form (e.g., co-formulation of Compound 1 with bicalutamide) or in separate dosage forms (e.g. Compound 1 formulated in an oral dosage form with bicalutamide in a separate oral dosage form or with a hormone agonist administered parenterally in a suspension formulation) either contemporaneously with each other (0-15 min apart) or within 15 min-24 hours, 30 min-24 hours apart or 1-24 hours apart, or administered using different dosage schedules (i.e., administered on different days) to permit optimal additive or synergistic interactions with each therapy component or to minimize adverse events by dosage reduction of one or more of the therapy components. If the subject with prostate cancer is androgen ablation insensitive, which includes prostate cancer that is androgen-independent, castrate-independent or hormone refractory, a solid state form of Compound 1 in an appropriate formulation is administered in combination with a cytotoxic agent such as an anti-microtubule agent, including but not limited to a taxane compound such as docetaxel or paclitaxel. The combination therapies may be co-administered either combined within a single dosage form (i.e., co-formulated where appropriate) or in separate dosage forms as previously described. Again, dosing amount and schedule may be varied to provide optimal therapy. Combination therapies using cytotoxic agents are typically initiated after the subject becomes symptomatic with metastatic disease.

In another embodiment the cancer being treated is breast cancer by administration of a solid state form of Compound 1 in an appropriate formulation either alone in combination with one or more other therapeutic agents common to the treatment of breast cancer. In one embodiment a solid dosage from of Compound 1 is used in combination with a gonadotropin-releasing hormone agonist such as leuprolide. In another embodiment the solid dosage from of Compound 1 may be used in combination with HERCEPTIN™ depending on the Her2/neu status of the tumor. In another embodiment the solid dosage form of Compound 1 is used in combination with an irreversible aromatase inhibitor such as exemestane, which forms a covalent bond with the aromatase enzyme or inhibitors such as anastrozole, or letrozole, which inhibit the aromatase enzyme by reversible competition. In another embodiment the solid dosage form of Compound 1 is used in combination a selective estrogen receptor modulator, such as tamoxifen or raloxifene, depending on the estrogen receptor status of the tumor. The combination therapies may be co-administered either combined within a single dosage form (i.e., co-formulated where appropriate) or in separate dosage forms as previously described. Again, dosing amount and schedule may be varied to provide optimal therapy. Compound 1 in solid state form is typically given to a subject having breast cancer alone or concurrent with hormone manipulation. Hormone manipulation is typically accomplished with TAMOXIFEN™ and an aromatase inhibitor such as ARIMIDEX™ (anastrozole) and is conducted after initial primary therapy, which may be surgery, chemotherapy, radiation or a combination thereof, to prevent recurrence. Compound 1 is this setting may replace tamoxifen or be administered in addition to TAMOXIFEN™. When used concurrently with a chemotherapeutic agent, as is sometime done in late stage disease, Compound 1 is administered in combination with a taxane compound, such as docetaxel or paclitaxel, to prolong the time before the next course of chemotherapy or is used to reduce the amount of chemotherapeutic agent to be given so as to mitigate the agent's side effects or to prevent or slow the emergence of resistance to the agent.

Numbered Embodiments.

Several aspects of the invention and related subject matter include the following numbered embodiments.

1. A solid state form of 17α-ethynyl-5α-androstane-3α,17β-diol.

2. The solid-state form of embodiment 1 wherein the solid-state form is one or more crystalline forms of 17α-ethynyl-5α-androstane-3α,17β-diol substantially free of 17α-ethynyl-5α-androstane-3α,17β-diol in amorphous form.

3. The solid-state form of embodiment 1 wherein solid-state form is a polymorph or pseudopolymorph of 17α-ethynyl-5α-androstane-3α,17β-diol and is essentially free of amorphous 17α-ethynyl-5α-androstane-3α,17β-diol.

4. The solid-state form of embodiment 1 wherein the solid-state form is a crystalline form of 17α-ethynyl-5α-androstane-3α,17β-diol and is essentially free of amorphous and other crystalline forms of 17α-ethynyl-5α-androstane-3α,17β-diol.

5. The solid state form of embodiment 4 wherein the solid-state form is characterized by: (a) an X-ray powder pattern with 2-theta values of 10.6, 14.7, 16.0±0.1 and optionally one or more 2-theta values of 12.3, 14.3, 15.9, 16.4, 17.5, 20.3, 24.0 and 27.2±0.1 and (b) optionally with differential thermal analysis thermogram (DTA) having a broad endotherm centered at about 81° C. and a prominent endotherm at about 164° C. (onset at about 162° C.) obtained with a heating rate of 10° C./min or is characterized by (a) and (b).

6. The solid state form of embodiment 5 further characterized by thermogravimetric analysis (TGA) thermogram with 12 wt % weight loss from about 40° C. to about 105° C. obtained with a heating rate of 10° C./min.

7. The solid state form of embodiment 5 further characterized by DTA thermogram with an exotherm at about 100° C.

8. The solid state form of embodiment 4 wherein the solid-state form is characterized by: (a) an X-ray powder pattern with 2-theta values of 11.3, 13.5, 16.2 and 16.5±0.1 and optionally one or more 2-theta values of 9.3, 9.9, 16.0. 17.4, and 19.0±0.10 and (b) optionally with DTA thermogram having a prominent endotherm at about 164° C. (onset at about 162° C.) and a TGA thermogram having negligible wt % weight loss from about 40° C. to about 105° C., obtained with a heating rate of 10° C./min or is characterized by (a) and (b).

9. The solid-state form of embodiment 8 further characterized by Raman spectra substantially identical to FIG. 5.

10. The solid-state form of embodiment 4 wherein the solid-state form is characterized by an X-ray powder diffraction pattern and differential scanning calorimetry (DSC) thermogram substantially identical to the X-ray powder diffraction pattern of FIG. 7 and DSC-TGA thermograms of FIG. 8.

11. The solid-state form of embodiment 10 further characterized by Raman spectra substantially identical to FIG. 9.

12. The solid-state form of embodiment 4 wherein the solid-state form is characterized by an X-ray powder diffraction pattern and DSC-TGA thermograms substantially identical to the X-ray powder diffraction pattern of FIG. 1 or FIG. 2 and DSC-TGA thermograms of FIG. 3.

13. The solid state form of embodiment 3 wherein the solid-state form is characterized by: (a) an X-ray powder pattern with 2-theta values of 9.8, 13.0, 14.7 and 17.0±0.1 and optionally one or more 2-theta values of 8.3, 11.3, 13.9, 15.0, 15.4, 16.1, 16.5, 17.8, 18.7, 20.0, 20.8, 22.1 and 25.1±0.1 and (b) optionally with DTA thermogram having a broad endotherm centered at about 88 C and a prominent endotherm at about 164° C. (onset at about 162° C.).

14. The solid state form of embodiment 13 further characterized by a TGA thermogram having between about 5-6 wt % weight loss from about 60° C. to about 105° C. or about 7 wt % weight loss from about 40° C. to about 160° C., obtained with a heating rate of 10° C./min or is characterized by (a) and (b).

15. The solid state form of embodiment 13 further characterized by DTA thermogram with an exotherm at about 106° C.

16. The solid state form of embodiment 3 wherein the solid-state form is characterized by an X-ray powder diffraction pattern and DTA-TGA thermograms substantially identical to the X-ray powder diffraction pattern of FIG. 12 and DTA-TGA thermograms of FIG. 13.

17. The solid state form of embodiment 3 wherein the solid-state form is characterized by: (a) an X-ray powder pattern with 2-theta values of 5.8, 9.5, 11.5, 15.2 and 18.9±0.1 and optionally one or more 2-theta values of 13.5, 16.0, 16.5, 17.3, 19.3, 20.9, 24.5 and 29.3±0.10 and (b) optionally with DTA thermogram having a prominent endotherm at about 164° C. (onset at about 162° C.) and TGA thermogram with negligible weight loss from about 40° C. to about 160° C., obtained with a heating rate of 10° C./min.

18. The solid state form of embodiment 3 wherein the solid-state form is characterized by an X-ray powder diffraction pattern substantially identical to the X-ray diffraction pattern of FIG. 15.

19. The solid state form of embodiment 3 wherein the solid-state form is characterized by: (a) an X-ray powder pattern with 2-theta values of 9.8, 13.3, 15.0 and 18.7±0.1 and optionally one or more 2-theta values of 6.7, 7.2, 7.5, 14.3, 14.6, 16.0, 17.0, 17.7, 18.3, 20.9 and 21.8±0.1 and (b) optionally with DTA thermogram having a prominent endotherm at about 164° C. (onset at about 162° C.) and TGA thermogram with about 5 wt % weight loss from about 40° C. to about 85° C. or about 12% weight loss from about 40° C. to about 180° C., obtained with a heating rate of 10° C./min.

20. The solid state form of embodiment 3 wherein the solid-state form is characterized by an X-ray powder diffraction pattern substantially identical to the X-ray diffraction pattern of FIG. 16 and DTA-TGA thermograms substantially identical to the DTA-TGA thermograms of FIG. 17.

21. The solid state form of embodiment 3 wherein the solid-state form is characterized by: (a) an X-ray powder pattern with 2-theta values of 9.8, 13.5, 14.2, 15.8, 19.5±0.1 and optionally one or more 2-theta values of 5.9, 8.3, 11.4, 11.9, 17.8, 21.4 and 26.9±0.10 and (b) optionally with DTA thermogram having a prominent endotherm at about 164° C. (onset at about 162° C.) and TGA thermogram with negligible wt % weight loss from about 40° C. to about 160° C.

22. The solid state form of embodiment 3 wherein the solid-state form is characterized by an X-ray powder diffraction pattern substantially identical to the X-ray diffraction pattern of FIG. 18.

23. The solid state form of embodiment 3 wherein the solid-state form is characterized by: (a) an X-ray powder pattern with 2-theta values of 11.1, 16.0, 11.6, 17.7 and 18.7±0.1 and optionally one or more 2-theta values of 9.4, 10.1, 19.1, 23.7, 24.3 and 28.4±0.10 and (b) optionally with DTA thermogram having a prominent endotherm at about 164° C. (onset at about 162° C.) and TGA thermogram with negligible wt % weight loss from about 40° C. to about 160° C.

Figure 19:
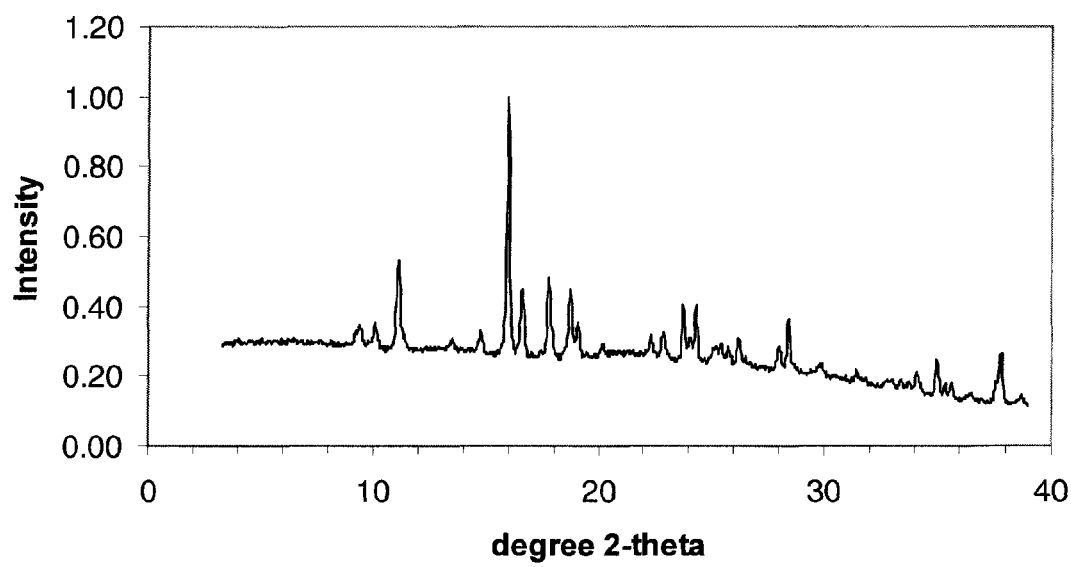
FIG. 19 provides an low resolution X-ray powder diffraction pattern of a sample comprising Form VIII 17α-ethynyl-5α-androstane-3α,17β-diol.

24. The solid state form of embodiment 3 wherein the solid-state form is characterized by an X-ray powder diffraction pattern substantially identical to the X-ray diffraction pattern of FIG. 19.

25. The solid-state form of embodiment 10 further characterized by Raman spectra substantially identical to FIG. 20.

26. The solid-state form of embodiment 1 wherein the solid-state form is amorphous 17α-ethynyl-5α-androstane-3α,17β-diol substantially free of 17α-ethynyl-5α-androstane-3α,17β-diol in crystalline form.

27. The solid-state form of embodiment 1 wherein the solid-state form is amorphous 17α-ethynyl-5α-androstane-3α,17O-diol essentially free of 17α-ethynyl-5α-androstane-3α,17β-diol in crystalline form 28. A solid formulation comprising a solid state form of 17α-ethynyl-5α-androstane-3α,17β-diol and at least one pharmaceutically acceptable excipient.

29. The formulation of embodiment 28 wherein the solid state form is one or more crystalline forms of 17α-ethynyl-5α-androstane-3α,17β-diol.

30. The formulation of embodiment 29 wherein one crystalline form is a polymorph or pseudopolymorph form of 17α-ethynyl-5α-androstane-3α,17β-diol and is substantially free of 17α-ethynyl-5α-androstane-3α,17β-diol in amorphous form.

31. The formulation of embodiment 29 wherein one crystalline form is a polymorph or pseudopolymorph form of 17α-ethynyl-5α-androstane-3α,17β-diol and is essentially free of amorphous 17α-ethynyl-5α-androstane-3α,17β-diol.

32. The formulation of embodiment 28 wherein the solid-state form is a crystalline form of 17α-ethynyl-5α-androstane-3α,17β-diol and is essentially free of amorphous and other crystalline forms of 17α-ethynyl-5α-androstane-3α, 17β-diol.

33. The formulation of embodiment 32 wherein the crystalline form is an anhydrate, optionally selected from the group consisting of crystalline Form Ill. Form V, Form VII and Form VIII 34. The formulation of embodiment 32 wherein the crystalline form is a solvate, optionally selected from the group consisting of crystalline Form I and Form IV 35. The formulation of embodiment 32 wherein the crystalline form is Form I 36. The formulation of embodiment 32 wherein the crystalline form is Form Ill.

37. The formulation of embodiment 32 wherein the crystalline form is Form IV

38. The formulation of embodiment 32 wherein the crystalline form is Form V.

39. The formulation of embodiment 32 wherein the crystalline form is Form VII.

40. The formulation of embodiment 32 wherein the crystalline form is Form VIII.

41. The formulation of embodiment 28 wherein the solid state form is amorphous 17α-ethynyl-5α-androstane-3α, 17β-diol.

42. The formulation of embodiment 41 wherein amorphous 17α-ethynyl-5α-androstane-3α,17β-diol is substantially free of crystalline 17α-ethynyl-5α-androstane-3α,17β-diol.

43. The formulation of any one of embodiments 28-42 wherein the formulation is in a capsule or tablet for oral dosing and the pharmaceutically acceptable excipient is a surface active agent in an amount sufficient to provide 90% dissolution of the formulation in water at ambient temperature after 30 min.

44. The formulation of embodiment 43 wherein the surface active agent is sodium lauryl sulfate.

45. The formulation of any one of embodiments 28-42 wherein the pharmaceutically acceptable excipients are comprised of sodium lauryl sulfate, microcrystalline cellulose and magnesium stearate 46. The formulation of any one of embodiments 28-42 wherein the pharmaceutically acceptable excipients consist essentially of sodium lauryl sulfate, microcrystalline cellulose and magnesium stearate in relative amounts to the solid state form of 17α-ethynyl-5α-androstane-3α,17β-triol as provided by Table 13 or Table 14.

47. A method to treat a hyperproliferation condition comprising administering to a subject in need thereof an effective amount of 17α-ethynyl-5α-androstane-3α,17β-triol in a solid state form or in a solid formulation comprising the solid state form of 17α-ethynyl-5α-androstane-3α,17β-triol and at least one pharmaceutically acceptable excipient.

48. The method of embodiment 29 wherein the solid state form is a crystalline form of 17α-ethynyl-5α-androstane-3α,17β-triol substantially free of 17α-ethynyl-5α-androstane-3α,17β-triol in amorphous form.

49. The method of embodiment 48 wherein the solid state form is a polymorph or pseudopolymorph form of 17α-ethynyl-5α-androstane-3,17β-triol essentially free or substantially free of amorphous and other crystalline forms of 17α-ethynyl-5α-androstane-3α,17β-triol.

50. The method of embodiment 31 wherein the polymorph or pseudopolymorph form is crystalline Form Ill.

51. The method of embodiment 29 wherein the hyperproliferation condition is a hormone sensitive or hormone associated cancer.

52. The method of embodiment 29 wherein the hyperproliferation condition is prostate cancer, breast cancer, benign prostatic hyperplasia or prostatic interstitial neoplasia.

53. A method of preparing a solid formulation of any one in embodiments 12-24 comprising the step of blending a solid state form of 17α-ethynyl-5α-androstane-3α,17β-triol with one, two, three or four pharmaceutically acceptable excipients wherein at least one excipient is a surface active agent.

54. The method of claim 53 wherein the solid state form is crystalline Form III.

55. The method of claim 53 wherein the solid state form is amorphous 17α-ethynyl-5α-androstane-3α,17β-triol.

56. The method of embodiment 53 wherein at least one excipient is sodium lauryl sulfate.

57. A method of preparing a liquid formulation comprising 17α-ethynyl-5α-androstane-3α,17β-triol and a pharmaceutically acceptable excipients wherein at least one excipient is a liquid excipient comprising the step of contacting or admixing a solid state form of 17α-ethynyl-5α-androstane-3α,17β-triol with the liquid excipient, optionally in the presence of another excipient.

58. The method of embodiment 55 wherein the solid state form is crystalline Form Ill.

59. The method of claim 57 wherein the solid state form is amorphous 17α-ethynyl-5α-androstane-3α,17β-triol.

60. A method to treat a hyperproliferation condition comprising administering to a subject in need thereof an effective amount of 17α-ethynyl-5α-androstane-3α,17β-triol in a liquid formulation prepared according to the method of claim 57, 58 or 59.

61. The method of claim 60 wherein the hyperproliferation condition is a hormone associated or a hormone sensitive cancer.

62. The method of claim 61 wherein the hyperproliferation condition prostate cancer, breast cancer, benign prostatic hyperplasia or prostatic interstitial neoplasia.

63. A product prepared by a process comprising the steps of admixing a methanolic solution of Compound 1 with sufficient water to form a precipitate.

64. A product prepared by a process comprising the step of heating a pseudopolymorph of Compound 1 under reduced pressure to effect desolvation of the pseudopolymorph.

65. The product of embodiment 64 wherein the pseudopolymorph is Form I

66. A product prepared by a process comprising the steps of admixing a hot EtOAc solution of Compound 1 with sufficient heptane to effect crystallization upon cooling to ambient temperature.

67. A product prepared by a process comprising the steps of (1) removing solvent from a THF solution of Compound 1 under ambient temperature and pressure to provide a gel (2) removing residual solvent from the gel under reduced pressure at ambient temperature.

68. A product prepared by a process comprising the step of fast evaporation of a solution of Compound 1 in 2:3 acetonitrile:water or admixing an acetonitrile solution of Compound 1 with sufficient water to effect crash precipitation.

69. A product prepared by a process comprising the steps of (1) admixing an acetonitrile solution of Compound 1 with water to provide 2:3 acetonitile:water solution and (2) removing solvent from the acetonitrile-water solution under ambient temperature and pressure.

70. A product prepared by a process comprising the steps of (3) removing solvent from an acetone solution of Compound 1 under ambient temperature and pressure.

71. A product prepared by a process comprising the steps of (1) admixing Form III Compound 1 with 2,2,2-trifluoroethanol (TFE) to form a slurry (2) agitating the TFE slurry at about 30° C. for up to about 6 days.

72. A product prepared by a process comprising the steps of (1) removing solvent from a dioxane solution of Compound 1 under ambient temperature and pressure to provide a gel (2) removing residual solvent from the gel under reduced pressure for up to 1 day at ambient temperature.

73. A product prepared by a process comprising the steps of (1) admixing a ethanolic slurry of Compound 1 with sufficient isopropyl acetate to effect dissolution under sonication; (2) removing sufficient solvent from the ethanol-isopropyl acetate solution to form solids such that complete re-dissolution will occur upon heating to about 47° C.; (3) cooling the re-dissolved solution to about 5° C.

74. A product prepared by a process comprising the steps of removing solvent from a dichloromethane solution of Compound 1 under ambient temperature and pressure.

Further aspects of the invention related to crystalline 17α-ethynyl-androstane-3α,17β-diol includes the following numbered embodiments.

1A. A crystalline form 17α-ethynyl-5α-androstane-3α,17β-diol.

2A. The crystalline form of embodiment 1A wherein the crystalline form is a pseudopolymorph, a polymorph or a mixture thereof.

3A. The crystalline form of embodiment 2A wherein the pseudopolymorph is a solvate.

4A. The crystalline form of embodiment 2A wherein the pseudopolymorph is a hydrate.

5A. The crystalline form of embodiment 3A wherein the solvate is a mixed solvate of water and an alcohol.

6A. The crystalline form of claim 2A wherein the crystalline form is a pseudopolymorph wherein the pseudopolymorph consists essentially of 17α-ethynyl-5α-androstane-3α,17β-diol, water and an alcohol wherein the alcohol is methanol.

7A. The crystalline form of 4A wherein the pseudopolymorph is a mixed solvate containing water and methanol in a water:methanol ratio of between about 2:1 to 1:1.

8A. The crystalline form of embodiment 4A wherein the crystalline form is a pseudopolymorph characterized by the molecular formula of $C_{21}H_{32}O_2 \cdot 1\, CH_3OH \cdot 1H_2O$.

9A. The crystalline form of embodiment 4A wherein the pseudopolymorph is essentially free of 17α-ethynyl-5α-androstane-3α,17β-diol in other crystalline forms and has a thermal gravimetric analysis thermogram with about 12 wt % when heated from about 25° C. to 60° C. to about 105° C. using a temperature ramp of 10° C./min.

10A. The crystalline form of embodiment 1A wherein the crystalline form is a product prepared by a process comprising the step of partial or complete desolvation of a pseudopolymorph of 17α-ethynyl-5α-androstane-3α,17β-diol.

11A. The crystalline form of embodiment 10A wherein the pseudopolymorph is a hydrate or a mixed solvate of water and methanol.

12A. The crystalline form of embodiment 10A wherein the pseudopolymorph is crystalline Form I, Form IV or Form VI 13A. The crystalline form of embodiment 1A wherein the crystalline form is an anhydrate.

14A. The crystalline form of embodiment 13A wherein the anhydrate is a product prepared from a process comprising the step of complete desolvation of crystalline Form I, Form IV or Form VI.

15A. The crystalline form of embodiment 13A wherein the anhydrate is crystalline Form Ill.

16A. The crystalline form of embodiment 1A wherein the crystalline form is characterized by one or more, typically 2, 3 or 4 XRPD prominent peaks in Table 1 or Table 2 optionally with a thermogram event obtained from a thermal analysis method disclosed herein.

17A. The crystalline form of embodiment 1A wherein the crystalline form is characterized by one or more, typically 2, 3 or 4 XRPD prominent peaks in Table 5. optionally with a thermogram event obtained from a thermal analysis method disclosed herein.

18A. The crystalline form of embodiment 1A wherein the crystalline form is characterized by one or more, typically 2, 3 or 4 XRPD prominent peaks in Table 8. optionally with a thermogram event obtained from a thermal analysis method disclosed herein.

19A. The crystalline form of embodiment 1A wherein the crystalline form is characterized by one or more, typically 2, 3 or 4 XRPD prominent peaks in Table 9. optionally with a thermogram event obtained from a thermal analysis method disclosed herein.

20A. The crystalline form of embodiment 1A wherein the crystalline form is characterized by one or more, typically 2, 3 or 4 XRPD prominent peaks in Table 10. optionally with a thermogram event obtained from a thermal analysis method disclosed herein.

21A. The crystalline form of embodiment 1A wherein the crystalline form is characterized by one or more, typically 2, 3 or 4 XRPD prominent peaks in Table 11. optionally with a thermogram event obtained from a thermal analysis method disclosed herein.

22A. The crystalline form of embodiment 1A wherein the crystalline form is characterized by one or more, typically 2, 3 or 4 XRPD prominent peaks in Table 12. optionally with a thermogram event obtained from a thermal analysis method disclosed herein.

23A. The crystalline form of embodiment 1A wherein the crystalline form is characterized by a pairwise distribution function calculated from the XRPD pattern of FIG. 2.

24A. The crystalline form of embodiment 1A wherein the crystalline form is characterized by a pairwise distribution function calculated from the XRPD pattern of FIG. 7.

25A. The crystalline form of embodiment 1A wherein the crystalline form is characterized by one or more absorptions, typically one or two absorptions, in Raman identified in FIG. 5.

26A. The crystalline form of embodiment 1A wherein the crystalline form is characterized by one or more absorptions, typically one or two absorptions, in Raman identified in FIG. 9.

Further aspects of the invention related to crystalline 17α-ethynyl-androstane-3α,17β-diol includes the following numbered embodiments.

1B. Crystalline 17α-ethynyl-androstane-3α,17β-diol.

2B. The crystalline 17α-ethynyl-androstane-3α,17β-diol of embodiment 1B wherein the crystalline 17α-ethynyl-androstane-3α,17β-diol is substantially free of amorphous 17α-ethynyl-androstane-3α,17β-diol, optionally as characterized an analytic method described herein such as XRPD, DSC, TGA, melting point, Raman spectroscopy, Karl Fisher and/or elemental analysis. Crystalline forms of 17α-ethynyl-androstane-3α,17β-diol includes anhydrates, hydrates and solvates, which include mixed water-solvent solvates. In these embodiments, crystalline 17α-ethynyl-androstane-3α,17β-diol that is substantially free of amorphous 17α-ethynyl-androstane-3α,17β-diol will typically and preferably contain less than about 10% w/w or less than about 7% w/w of the amorphous material.

3B. The crystalline 17α-ethynyl-androstane-3α,17β-diol of embodiment 1B or 2B as Form I crystals. This form of 17α-ethynyl-androstane-3α,17β-diol is a mixed solvate material with a 1:1:1 ratio of 17α-ethynyl-androstane-3α,17β-diol:water:methanol and is typically substantially free of amorphous 17α-ethynyl-androstane-3α,17β-diol.

4B. The crystalline Form I 17α-ethynyl-androstane-3α,17β-diol of embodiment 3B that contains less than about 10% w/w or less than about 7% w/w of other crystalline forms of 17-ethynyl-androstane-3α,17β-diol, optionally as characterized by an analytic method described herein such as XRPD, DSC, TGA, melting point, Raman spectroscopy, Karl Fisher and/or elemental analysis.

5B. The crystalline of 17α-ethynyl-androstane-3α,17β-diol of embodiment 3A characterized by (1) space group $P2_12_12$, (No. 19); Z=4 or (2) unit cell parameters of a=7.4893(4) Å, b=11.0586(8) Å, c=25.5095(15) Å, α=90.00°, β=90.00°, γ=90.00°, V=2112.7(2) Å$^3$.

6B. The crystalline form of 17α-ethynyl-androstane-3α,17β-diol of embodiment 3A characterized by (1) an XRPD pattern with prominent peaks at about 10.59, 12.33, 14.29, 14.72, 16.04, 16.41, 17.49, 20.27, 24.04 and 27.21 degrees 2θ, optionally with (2) a DTA or DSC thermogram having an endotherm with onset at about 160° C.±3° and TGA thermogram with wt % loss of at least about 10% or water content of about 5% by Karl-Fischer titration 7B. The crystalline form or 17α-ethynyl-androstane-3α,17β-diol of embodiment 3A characterized by (1) an XRPD pattern with peaks at about 9.30, 9.85, 11.33, 13.45, 15.96, 16.16, 16.48 and 17.42 degrees 2θ optionally with (2) a DTA or DSC thermogram having an endotherm onset at about 160° C.±3° and a TGA thermogram with negligible wt % loss, weight of 2% or less, or weight loss of 0.3% from about 40° C. to about 105° C. or from about 40° C. to about 160° C. using a temperature ramp of 10° C./min.

8B. The crystalline form of embodiment 1B or 2B wherein the crystalline is Form III characterized by sufficient bioavailability of the crystalline material to be suitable for once daily or twice daily administration of unit oral doses of 5 mg, 10 mg, 15 mg, 20 mg or 50 mg to a human, such as a human having a cancer or a precancer, optionally benign prostatic hypertrophy, prostate cancer or breast cancer.

9B. The crystalline form of embodiment 1B, 2B or 8B wherein the crystalline form is Form III characterized by sufficient stability on storage at 65° C. and 75% relative humidity for at least 6 months wherein sufficient stability is characterized by a change of less than about 5% w/w in the degradation of 17α-ethynyl-androstane-3α,17β-diol to a degradant or by conversion of less than about 5% w/w to another solid state form.

10B. The crystalline 117-ethynyl-androstane-3α,17β-diol of embodiment 1B or 2B as Form III crystals. This form of 17α-ethynyl-androstane-3α,17β-diol is an anhydrate and does not contain a solvent as measured by an analytical method described herein such as Karl Fisher titration, gas chromatography analysis, proton-NMR spectroscopy and/or elemental analysis, and in preferred embodiments it is substantially free of amorphous 17α-ethynyl-androstane-3α,17β-diol, optionally as measured by an analytical method described herein such as XRPD, DSC/DTA, TGA, Raman spectroscopy or solid state NMR spectroscopy 11B. The crystalline Form III 17α-ethynyl-androstane-3α,17β-diol of embodiment 10B that contains less than about 10% w/w or less than about 7% w/w of other crystalline forms of 17α-ethynyl-androstane-3α,17β-diol, optionally as characterized by an analytical method described herein such as XRPD, DSC/DTA, TGA, Raman spectroscopy or solid state NMR spectroscopy.

12B. The crystalline Form III 17α-ethynyl-androstane-3α,17β-diol of embodiment 10B or 11B having (1) an XRPD pattern with prominent peaks at about 9.30, 9.85, 11.33, 13.45, 15.96, 16.16, 16.48 and 17.42 degrees or (2) a Raman trace substantially identical to that shown in FIG. 5 or a combination of (1) and (2).

The crystalline Form III 17α-ethynyl-androstane-3α,17β-diol of embodiment 10B that contains less than about 10% w/w or less than about 7% w/w of other crystalline forms of 17α-ethynyl-androstane-3α,17β-diol, optionally as characterized by an analytical method described herein such as XRPD, DSC/DTA, TGA, Raman spectroscopy or solid state NMR spectroscopy.

12B. The crystalline Form I 17α-ethynyl-androstane-3α, 177-diol of embodiment 3B characterized by (1) an XRPD pattern with prominent peaks at about 10.59, 12.33, 14.29, 14.72, 16.04, 16.41, 17.49, 20.27, 24.04 and 27.21 degrees 2θ or (2) a Raman trace substantially identical to that shown in FIG. 9 or a combination of (1) and (2).

13B. The crystalline 17α-ethynyl-androstane-3α,17β-diol of embodiment 1B or 2B as Form IV crystals. This form of 17α-ethynyl-androstane-3α,17β-diol is a hydrate and contains water in a 1:1 ratio. In preferred embodiments it is substantially free of amorphous 17α-ethynyl-androstane-3α, 17β-diol, optionally as measured by an analytical method described herein such as XRPD, DSC/DTA, TGA, Raman spectroscopy and/or solid state NMR.

14B. The crystalline Form IV 17α-ethynyl-androstane-3α, 17β-diol of embodiment 13B that contains less than about 10% w/w or less than about 7% w/w of other crystalline forms of 17α-ethynyl-androstane-3α,17β-diol, optionally as characterized by an analytic method described herein such as XRPD, DSC, TGA, Raman spectroscopy and/or solid state NMR.

15B. The crystalline Form IV 17α-ethynyl-androstane-3α, 17β-diol of embodiment 13B or 14B characterized by (1) an XRPD pattern with prominent peaks at about 8.31, 9.84, 11.28, 13.02, 13.86, 14.73, 15.00, 16.14, 16.53, 17.01, 17.76 and 18.72 degrees 2θ, (2) a DTA or DSC thermogram with an exotherm onset at about 105° C.±3°, (3) a TGA thermogram with a weight loss on heating to the melting point that corresponds to complete loss of water for a monohydrate or (4) a combination of the foregoing such as (1) and (2), (1) and (3) or (2) and (3).

16B. The crystalline 17α-ethynyl-androstane-3α,17β-diol of embodiment 1B or 2B as Form V crystals. This form of 17α-ethynyl-androstane-3α,17β-diol is an anhydrate. In preferred embodiments it is substantially free of amorphous 17α-ethynyl-androstane-3α,17β-diol, optionally as measured by an analytical method described herein such as XRPD, DSC/DTA, TGA, Raman spectroscopy and/or solid state NMR.

17B. The crystalline Form V 17α-ethynyl-androstane-3α, 17β-diol of embodiment 13B that contains less than about 10% w/w or less than about 7% w/w of other crystalline forms of 17α-ethynyl-androstane-3α,17β-diol, optionally as characterized by an analytic method described herein such as XRPD, DSC, TGA, melting point, Raman spectroscopy and/ or solid state NMR.

17B. The crystalline Form V 17α-ethynyl-androstane-3α, 17β-diol of embodiment 16B or 17B characterized by (1) an XRPD pattern with prominent peaks at about 5.82, 9.48, 11.49, 13.50, 15.21, 17.28 and 18.93 degrees 2E, (2) a TGA thermogram with negligible weight loss, 2% or less weight loss, or 0.3% or less weight loss on heating to the melting point (3) a DTA or DSC thermogram having an endotherm at about 164° C. or (4) a combination of (1) and (2) or (1) and (3).

18B. The crystalline 17α-ethynyl-androstane-3α,17β-diol of embodiment 1B or 2B as Form VI crystals. This form of 17α-ethynyl-androstane-3α,17β-diol is a dioxane solvate in a 1:1 ratio. In preferred embodiments it is substantially free of amorphous 17α-ethynyl-androstane-3α,17β-diol, optionally as measured by an analytical method described herein such as XRPD, DSC/DTA, TGA, Raman spectroscopy and/or solid state NMR.

19B. The crystalline Form VI 17α-ethynyl-androstane-3α, 17β-diol of embodiment 18B that contains less than about 10% w/w or less than about 7% w/w of other crystalline forms of 17α-ethynyl-androstane-3α,17β-diol, optionally as characterized by an analytical method described herein such as XRPD, DSC/DTA, TGA, Raman spectroscopy and/or solid state NMR.

20B. The crystalline Form VI 17α-ethynyl-androstane-3α, 17β-diol of embodiment 16B or 17B characterized by (1) an XRPD pattern with prominent peaks at about 7.17, 9.78, 13.26, 14.25, 14.61, 15.00 and 18.69 degrees 2θ, (2) a TGA thermogram with a weight loss on heating to the melting point with the loss corresponding to complete loss of dioxane from a mono solvate (3) proton NMR spectrum obtained in CDCl₃ with a peak at about δ=3.6 ppm, (4) a DSC or DTA thermogram with an endotherm at about 164° C. or (5) a combination of the forgoing such as (1) and (2), (1) and (3), (1) and (4) or (2), (3) and (4).

21B. The crystalline 17α-ethynyl-androstane-3α,17β-diol of embodiment 1B or 2B as Form VII crystals. This form of 17α-ethynyl-androstane-3α,17β-diol is an anhydrate. In preferred embodiments it is substantially free of amorphous 17α-ethynyl-androstane-3α,17β-diol, optionally as measured by an analytical method described herein such as XRPD, DSC/DTA, TGA, Raman spectroscopy, and/or solid state NMR.

22B. The crystalline Form VII 17α-ethynyl-androstane-3α,17β-diol of embodiment 19A that contains less than about 10% w/w or less than about 7% w/w of other crystalline forms of 17α-ethynyl-androstane-3α,17β-diol, optionally as characterized by an analytical method described herein such as XRPD, DSC/DTA, TGA, Raman spectroscopy and/or solid state NMR.

23B. The crystalline Form VII 17α-ethynyl-androstane-3α,17β-diol of embodiment 20B or 21B characterized by (1) an XRPD pattern with prominent peaks at about 5.91, 9.78, 13.47, 14.16, 15.78, 17.85, 19.50 and 21.45 degrees 2θ or (2) a TGA thermogram with negligible weight loss, 2% or less weight loss, or 0.3% or less weight loss on heating to the melting point (3) a DTA or DSC thermogram having an endotherm at about 164° C. or a combination of the foregoing such as (1) and (2), (1) and (3) or (1) (2) and (3).

24B. The crystalline 17α-ethynyl-androstane-3α,17β-diol of embodiment 1B or 2B as Form VIII crystals. This form of 17α-ethynyl-androstane-3α,17β-diol is an anhydrate. In preferred embodiments it is substantially free of amorphous 17α-ethynyl-androstane-3α,17β-diol, optionally as measured by an analytical method described herein such as XRPD, DSC/DTA, TGA, Raman spectroscopy, and/or solid state NMR.

24B. The crystalline Form VIII 17α-ethynyl-androstane-3α,17β-diol of embodiment 24B that contains less than about 10% w/w or less than about 7% w/w of other crystalline forms of 17α-ethynyl-androstane-3α,17β-diol, optionally as characterized by an analytic method described herein such as XRPD, DSC, TGA, melting point, Raman spectroscopy, Karl Fisher and/or elemental analysis.

25B. The crystalline Form VIII 17α-ethynyl-androstane-3α,17β-diol of embodiment 23B or 24B characterized by (1) an XRPD pattern with prominent peaks at about 11.13, 15.96, 16.62, 17.76 and 18.75 degrees 2θ, (2) a TGA thermogram with negligible weight loss, 2% or less weight loss, or 0.3% or less weight loss on heating to the melting point (3) a DTA or DSC thermogram having an endotherm at about 164° C. or a combination of the foregoing such as (1) and (2), (1) and (3) or (1) (2) and (3).

26B. Use of crystalline 17α-ethynyl-androstane-3α,17β-diol, or use of a composition comprising one or more excipients and crystalline 17α-ethynyl-androstane-3α,17β-diol, for the preparation of a medicament for the treatment or prophylaxis of a cancer or a precancer, optionally wherein the cancer or precancer is prostate cancer, breast cancer, ovarian cancer, endometrial cancer, lung cancer, pancreatic cancer or benign prostatic hypertrophy. In these embodiments, the use of crystalline Forms 1, III, IV, V, VII and VIII of 17α-ethynyl-androstane-3α,17β-diol are preferred, with Forms III most preferred. In these uses appreciable amounts of two crystal forms can be present, but there is preferably only 1 crystalline form present, e.g., a single crystal form comprises at least about 90% w/w or at least about 93% w/w of the ethynyl-androstane-3α,17β-diol that is present.

27B. Use according to embodiment 26B wherein the crystalline 17α-ethynyl-androstane-3α,17β-diol is substantially free of amorphous 17α-ethynyl-androstane-3α,17β-diol, optionally as characterized by an analytical method described herein such as XRPD, DSC/DTA, TGA, Raman spectroscopy and/or solid state NMR.

Further aspects of the invention related to amorphous 17α-ethynyl-androstane-3α,17β-diol include the following numbered embodiments.

1C. Amorphous 17α-ethynyl-5α-androstane-3α,17β-diol.

2C. The amorphous 17α-ethynyl-5α-androstane-3α,17β-diol of embodiment 1C wherein the amorphous 17α-ethynyl-5α-androstane-3α,17β-diol is substantially free of crystalline 17α-ethynyl-5α-androstane-3α,17β-diol as measured by XRPD analysis, optionally wherein the amorphous 17α-ethynyl-5α-androstane-3α,17β-diol is substantially free of crystalline Form I and/or Form III 17α-ethynyl-5α-androstane-3α,17β-diol.

3C. The amorphous 17α-ethynyl-5α-androstane-3α,17β-diol of embodiment 1C or 2C wherein the amorphous 17α-ethynyl-5α-androstane-3α,17β-diol contains less than about 8% w/w of crystalline 17α-ethynyl-5α-androstane-3α,17β-diol.

4C. The amorphous 17α-ethynyl-androstane-3α,17β-diol of embodiment 1C, 2C or 3C wherein the amorphous 17α-ethynyl-androstane-3α,17β-diol contains less than about 5% w/w of crystalline 17α-ethynyl-5α-androstane-3α,17β-diol.

5C. A pharmaceutical formulation comprising one or more excipients and amorphous 17α-ethynyl-5α-androstane-3α,17β-diol, optionally wherein the amorphous 17α-ethynyl-5α-androstane-3α,17β-diol is as described in embodiment 1C, 2C, 3C or 4C.

6C. A product, amorphous 17α-ethynyl-5α-androstane-3α,17β-diol, produced by a process comprising the step of adding 10% by volume water to a filtered solution of about 0.25 mg/mL Compound 1 in methanol with agitation 7C. The product of embodiment 6C wherein the amorphous 17α-ethynyl-5α-androstane-3α,17β-diol (1) is substantially free of crystalline 17α-ethynyl-androstane-3α,17β-diol as measured by XRPD analysis, or (2) contains less than about 8% w/w of crystalline 17α-ethynyl-5α-androstane-3α,17β-diol, or (3) contains less than about 5% w/w of crystalline 17α-ethynyl-5α-androstane-3α,17β-diol, optionally wherein the crystalline 17α-ethynyl-5α-androstane-3α,17β-diol is Form I and/or Form I 17α-ethynyl-5α-androstane-3α,17β-diol.

8C. Use of amorphous 17α-ethynyl-5α-androstane-3α,17β-diol, or use of a composition comprising one or more excipients and amorphous 17α-ethynyl-5α-androstane-3α,17β-diol for the preparation of a medicament for the treatment or prophylaxis of a cancer, precancer or hyperplasia, optionally wherein the cancer or hyperplasia is prostate cancer, breast cancer, ovarian cancer, endometrial cancer or benign prostatic hypertrophy. In these uses, amorphous material preferably comprises at least about 90% w/w or at least about 95% w/w of the 17α-ethynyl-5α-androstane-3α,17β-diol that is present.

9C. Use according to embodiment 8C wherein the amorphous 17α-ethynyl-androstane-3α,17β-diol is substantially free of crystalline 17α-ethynyl-5α-androstane-3α,17β-diol as measured by XRPD analysis or wherein the amorphous 17α-ethynyl-5α-androstane-3α,17β-diol contains less than about 8% w/w or less than about 5% w/w of crystalline 17α-ethynyl-5α-androstane-3α,17β-diol.

EXAMPLES

Example 1

Synthesis of 17-ethynyl-5α-androstane-3α,17β-diol

Step A. Synthesis of 3α-trimethylsilyoxy-androst-5-en-17-one (TMS-3α-DHEA): 3α-DHEA is combined with 1,1, 1,3,3,3-hexamethyldisilazane (HMDS) and saccharin (as catalyst) in acetonitrile. The reaction mixture is heated to reflux for several hours with stirring under a nitrogen atmosphere. Liberated ammonia is purged under slight vacuum. The volume is then reduced by distillation, followed by cooling the mixture and collecting the precipitated product by filtration. The filter cake of TMS-3α-DHEA product is washed with cold acetonitrile and dried with warm nitrogen to provide the title compound.

Step B. n-Butyl lithium is added slowly to Me$_3$Si—C≡CH in THF under a nitrogen atmosphere at approximately 0° C. to produce the lithium acetylide Me$_3$Si—C≡C—Li. The temperature is raised to about 20° C., and TMS-3α-DHEA is added as a solution in THF, and stirred for about 3 hours. The reaction is quenched by raising the temperature to about 40° C. followed by the slow addition of methanol. Liberated acetylene is purged under slight vacuum. Concentrated KOH is then slowly added until gas evolution subsides, and the volume is reduced by approximately 50% by vacuum distillation at approximately 45° C. Excess 6 N HCl is slowly added, while maintaining the temperature at approximately 40° C. The reaction mixture is diluted with water and chilled to approximately 5° C. before collecting the product by filtration and washing the filter cake with cold 50/50 methanol water. The product is dried with warm nitrogen to provide 17β-ethynyl-androst-5-ene-3α,17α-diol.

Step C. To 9.0 Kg of the title compound in a 250 L reactor was added 71.2 Kg methanol. The agitated mixture was heated to reflux until the solids had dissolved. After cooling to 55-60° C. the reactor contents were filtered through a 25-micron filter and the reactor was then rinsed with 2.4 Kg MeOH heated to 55-60° C. and filtered as above to combine the filtrates. To the combined filtrates agitated in a 250 L reactor was added over a period of 30-60 min. 81.0 Kg of deionized water to form a slurry while maintaining the temperature between 35-60° C. The slurry was then cooled to 0-5° C. over a period of at least 2 h and the temperature was maintained for at least 1 h whereupon the solids were collected by filtration. The filter cake was washed by slurring with 10 Kg deionized water (repeated 2×). The filter cake was allowed to dry under vacuum at about 28.5 in. Hg at about 45° C. to loss on drying of 0.5% or less. Obtained was 8.4 Kg of the title material in crystalline form.

The crystalline form of Compound 1 obtained from this synthetic procedure is represented by the low resolution XRPD pattern of FIG. 1. Peak listing for the X-Ray Powder Diffraction (XRPD) pattern of FIG. 1 is provided in Table 1.

TABLE 1

| Peak Listing for XRPD Pattern of Synthesis Product-Low Resolution | |
|---|---|
| °2θ | Intensity (%) |
| 9.38 ± 0.10 | 9 |
| 9.66 ± 0.10 | 21 |
| 11.32 ± 0.10 | 30 |
| 13.44 ± 0.10 | 100 |
| 15.94 ± 0.10 | 57 |
| 16.46 ± 0.10 | 37 |
| 17.38 ± 0.10 | 21 |
| 18.66 ± 0.10 | 17 |
| 19.40 ± 0.10 | 40 |
| 19.44 ± 0.10 | 40 |
| 20.74 ± 0.10 | 10 |
| 21.44 ± 0.10 | 11 |
| 21.56 ± 0.10 | 13 |
| 24.76 ± 0.10 | 10 |
| 25.42 ± 0.10 | 8 |
| 26.64 ± 0.10 | 12 |

TABLE 1-continued

| Peak Listing for XRPD Pattern of Synthesis Product-Low Resolution | |
|---|---|
| °2θ | Intensity (%) |
| 27.04 ± 0.10 | 8 |
| 27.68 ± 0.10 | 13 |
| 27.92 ± 0.10 | 10 |
| 28.94 ± 0.10 | 6 |
| 29.68 ± 0.10 | 7 |
| 33.26 ± 0.10 | 6 |
| 34.00 ± 0.10 | 10 |
| 35.40 ± 0.10 | 10 |
| 36.44 ± 0.10 | 8 |
| 37.84 ± 0.10 | 10 |
| 38.64 ± 0.10 | 7 |

Thermal analysis for the synthesis product provides a thermogravimetric analysis (TGA) thermogram showing negligible weight loss from about 35° C. to about 105° C. using a temperature ramp of 10° C./min and a differential thermal analysis (DTA) thermogram showing a prominent endotherm at about 164° C. and is otherwise featureless. Thus, thermal analysis indicates that the prominent or sole polymorphic form within the product is most likely an anhydrate. XRPD, DTA and TGA data is thus consistent with crystalline Form III, discussed in subsequent example, as the dominant or sole crystalline form in the synthesis product.

Example 2

Preparation and Analysis of Crystalline Form III
17α-ethynyl-5α-androstane-3α,17β-diol (Form III
Compound 1)

Compound 1 (65.8 g) synthesis product from the immediately preceding example was dried under vacuum at 80° C. to constant weight, typically requiring heating overnight, to provide 57.9 g. This dried material was dissolved into 230 mL HPLC grade EtOAc at 80° C. agitated by swirling. The solution was hot filtered through a coarse glass fritted funnel to remove residual solids then transferred to a 2 L flask to resume heating at 80° C. HPLC grade heptane (1.158 L) was the added in about 100 mL aliquots with swirling. After completion of addition, the mixture was allowed to cool to ambient temperature and allowed to stand overnight. The crystalline material was collected by filtration, air dried for 20 min and under vacuum overnight to provide 48.8 g of Form III 17α-ethynyl-5α-androstane-3α,17β-diol. Form III was also prepared by dissolving Compound 1 (44.0 mg) in tetrahydrofuran (600 µL). The solution was filtered through 0.2 µm nylon filter to a clean vial. The solvent was slowly evaporated under ambient conditions yielding a gel that was vacuum dried at ambient temperature for 4 days to provide Compound 1 in crystalline Form Ill.

Additionally, Form III may produced by vapor stressing a melt-quench sample of Compound 1 as described in a subsequent example for amorphous material.

Figure 2:
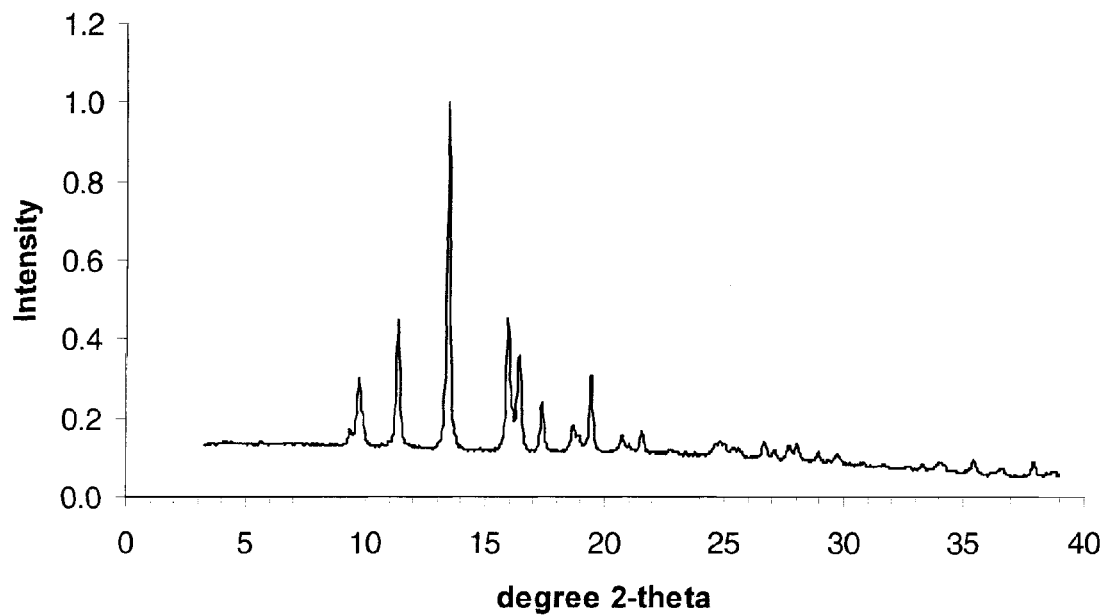
FIG. 2 provides a high resolution X-ray powder diffraction pattern of a sample comprising Form III 17α-ethynyl-5α-androstane-3α,17β-diol.

The high resolution XRPD for Form III, prepared according to the immediately preceding procedure is given in FIG. 2. Peak listing for this XRPD pattern is given in Table 2. Prominent peaks are at 9.30, 9.85, 11.33, 13.45, 15.96, 16.16, 16.48 and 17.42±0.10 degrees 2θ.

TABLE 2

Peak Listing for XRPD Pattern of Form III-High Resolution

| °2θ | d space (Å) | Intensity (%) |
|---|---|---|
| 9.30 ± 0.10 | 9.506 ± 0.103 | 18 |
| 9.70 ± 0.10 | 9.122 ± 0.095 | 8 |
| 9.85 ± 0.10 | 8.976 ± 0.092 | 15 |
| 11.33 ± 0.10 | 7.807 ± 0.069 | 53 |
| 13.45 ± 0.10 | 6.584 ± 0.049 | 100 |
| 15.96 ± 0.10 | 5.552 ± 0.035 | 29 |
| 16.16 ± 0.10 | 5.484 ± 0.034 | 39 |
| 16.48 ± 0.10 | 5.379 ± 0.033 | 91 |
| 17.42 ± 0.10 | 5.092 ± 0.029 | 24 |
| 18.70 ± 0.10 | 4.744 ± 0.025 | 5 |
| 18.95 ± 0.10 | 4.682 ± 0.025 | 11 |
| 19.46 ± 0.10 | 4.563 ± 0.023 | 8 |
| 19.78 ± 0.10 | 4.488 ± 0.023 | 1 |
| 20.75 ± 0.10 | 4.281 ± 0.021 | 7 |
| 21.08 ± 0.10 | 4.214 ± 0.020 | 2 |
| 21.60 ± 0.10 | 4.114 ± 0.019 | 2 |
| 22.79 ± 0.10 | 3.902 ± 0.017 | 2 |
| 24.62 ± 0.10 | 3.616 ± 0.015 | 1 |
| 24.80 ± 0.10 | 3.590 ± 0.014 | 6 |
| 25.01 ± 0.10 | 3.560 ± 0.014 | 8 |
| 25.39 ± 0.10 | 3.508 ± 0.014 | 3 |
| 25.65 ± 0.10 | 3.474 ± 0.013 | 5 |
| 26.67 ± 0.10 | 3.342 ± 0.012 | 7 |
| 27.09 ± 0.10 | 3.291 ± 0.012 | 3 |
| 27.69 ± 0.10 | 3.221 ± 0.011 | 2 |
| 28.04 ± 0.10 | 3.183 ± 0.011 | 3 |
| 28.93 ± 0.10 | 3.086 ± 0.010 | 5 |
| 29.84 ± 0.10 | 2.994 ± 0.010 | 2 |

Crystalline Form III, and all other crystalline forms of 17α-ethynyl-5α-androstane-3α,17β-diol such as Form I, Form IV, Form V, Form VI, Form VII and Form VIII is optimally characterized at least in part by reference to 1 or more, typically 2, 3, 4, 5, or 6 prominent, representative or characteristic peaks in the XRPD pattern by reference to peak positions (degrees 2-theta) and optionally to peak intensities.

Figure 3:
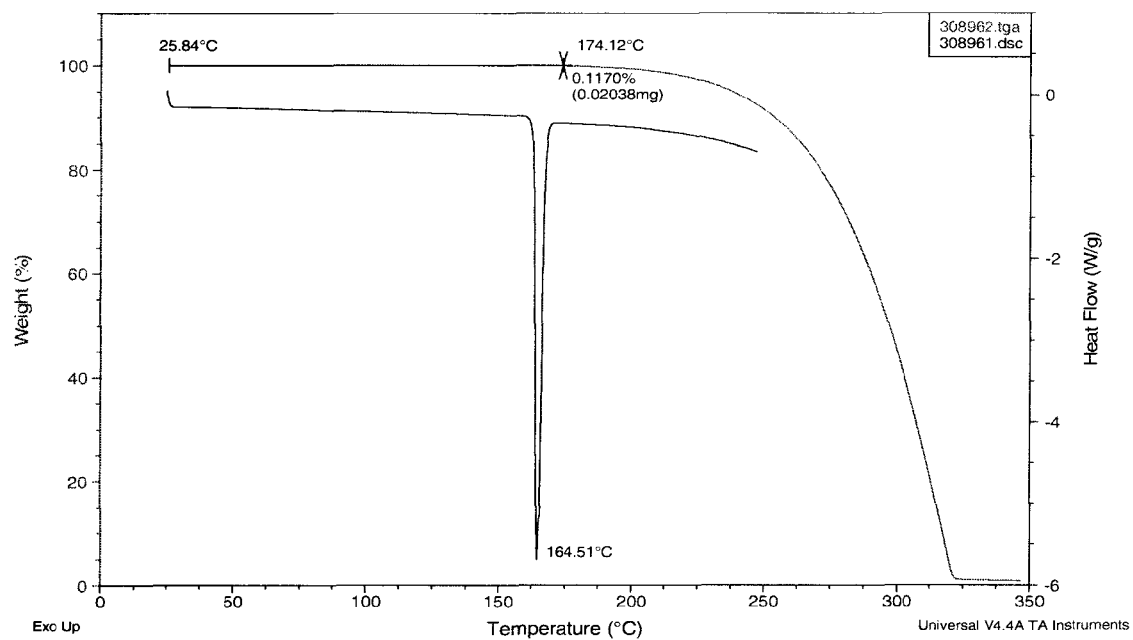
FIG. 3 provides differential scanning calorimetry and thermogravimetric analysis thermograms of a sample comprising Form III 17α-ethynyl-5α-androstane-3α,17β-diol.

Differential scanning calorimetry (DSC) and TGA thermograms for Form III are presented in FIG. 3. TGA shows negligible weight loss from about 35° C. to about 105° C. indicating that the polymorphic forms within the solid state mixture are most likely anhydrates. DSC shows a prominent endotherm at about 164° C. and is otherwise featureless, further indicating anhydrous material.

Figure 4A:
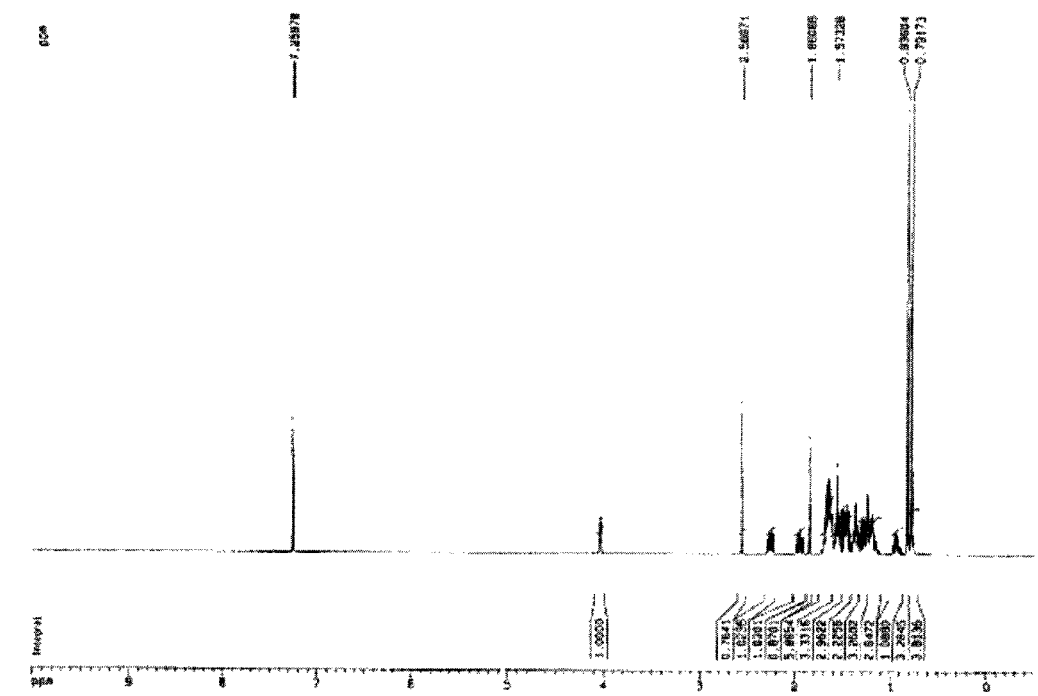
FIG. 4 provides a proton NMR spectroscopy spectrum of a sample comprising Form III 17α-ethynyl-5α-androstane-3α,17β-diol.
Figure 4B:
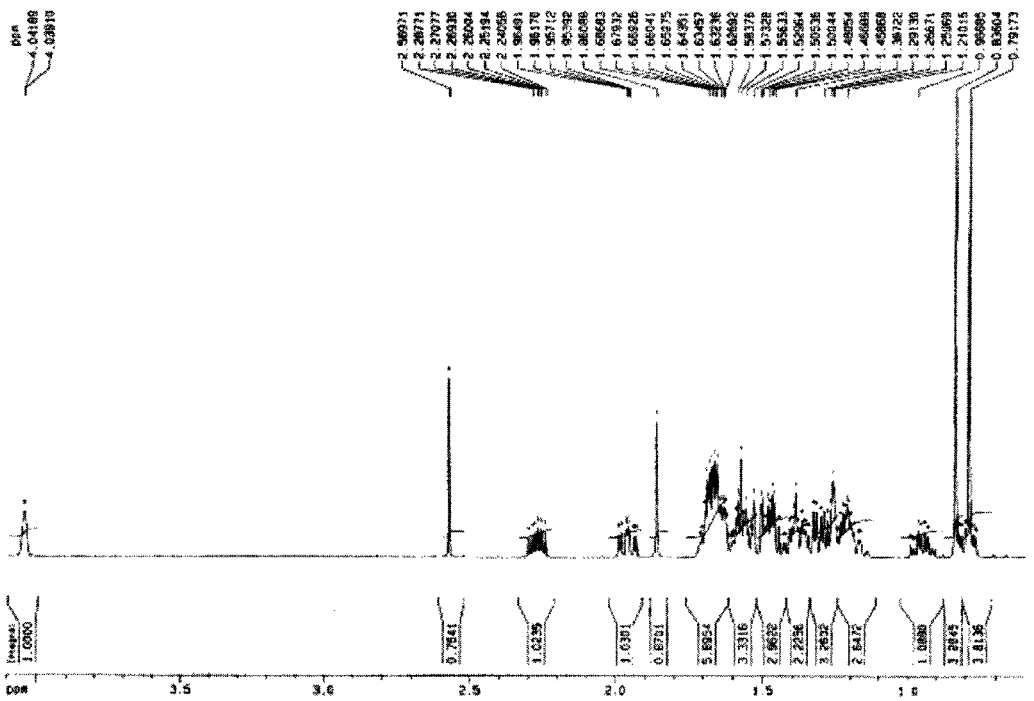

FIG. 4 is a proton FT-NMR (CDCl$_3$) of Form III 17α-ethynyl-5α-androstane-3α,17β-diol, which does not exhibit additional resonances due to solvent, thus further confirming that Form III is not a solvate.

FIG. 5 is a Raman spectroscopy spectrum of Form III 17α-ethynyl-5α-androstane-3α,17β-diol Peak position for this Raman spectrum is given in Table 2B.

TABLE 2B

| Position (cm$^{-1}$) | Intensity |
|---|---|
| 131.4 | 0.983 |
| 206.2 | 1.448 |
| 236.0 | 2.170 |
| 272.3 | 0.808 |
| 324.1 | 0.736 |
| 373.9 | 0.806 |
| 384.0 | 0.858 |
| 395.4 | 1.003 |
| 432.1 | 1.040 |
| 454.7 | 0.879 |
| 466.7 | 0.672 |
| 489.7 | 1.598 |
| 510.4 | 0.517 |
| 526.1 | 1.600 |
| 549.1 | 1.194 |
| 602.5 | 1.328 |
| 619.2 | 1.152 |
| 648.3 | 1.225 |
| 657.5 | 0.978 |
| 702.9 | 1.360 |
| 733.2 | 2.078 |
| 797.6 | 0.392 |
| 825.1 | 0.598 |
| 833.0 | 0.670 |
| 874.3 | 0.327 |
| 890.8 | 0.631 |
| 907.5 | 0.584 |
| 928.8 | 0.459 |
| 963.3 | 0.825 |
| 986.2 | 0.430 |
| 1006.9 | 0.754 |
| 1038.0 | 0.615 |
| 1051.5 | 0.554 |
| 1093.1 | 0.362 |
| 1110.6 | 0.655 |
| 1150.0 | 1.014 |
| 1166.4 | 1.105 |
| 1189.8 | 0.775 |
| 1235.8 | 0.972 |
| 1254.5 | 1.603 |
| 1293.4 | 0.592 |
| 1317.3 | 0.559 |
| 1335.1 | 0.863 |
| 1352.8 | 0.751 |
| 1376.3 | 0.686 |
| 1386.0 | 0.691 |
| 1434.8 | 1.856 |
| 1457.4 | 1.468 |
| 1469.5 | 0.969 |
| 2103.9 | 2.626 |
| 2648.4 | 0.150 |
| 2857.1 | 1.486 |
| 2864.7 | 1.509 |
| 2942.9 | 2.821 |
| 2964.2 | 1.509 |
| 2982.8 | 0.774 |
| 3303.4 | 0.581 |

Calculated theoretical percentages of Compound 1 as the anhydrous, hemi-hydrate, and monohydrate forms compared with the measured elemental analysis values are given in Table 3. The measured percent values for the solid state obtained from the procedure described directly above lot are within the American Chemical Society recommendation values of 0.4% for the theoretical carbon and hydrogen percentage for anhydrous Compound 1. Therefore, elemental analysis confirms crystalline Form III obtained from the immediately proceeding procedure is an anhydrous solid state form of Compound 1, as shown by the DSC/TGA thermograms and as further confirmed by low residual water determination of 0.20% by Karl Fischer analysis.

TABLE 3

Calculated v Actual % C and H for Form III

| Mol. Form. | $C_{21}H_{30}O_3$ | $C_{21}H_{30}O_3 \cdot \frac{1}{2}H_2O$ | $C_{21}H_{30}O_3 \cdot H_2O$ | Measured |
|---|---|---|---|---|
| Carbon % | 79.70 | 77.49 | 75.40 | 79.3 |
| Hydrogen % | 10.11 | 10.22 | 10.25 | 10.3 |

Since crystalline Form III 17α-ethynyl-androstane-3α,17β-diol is an anhydrate, it does not contain any organic solvent such as methanol or dioxane, and thus it has the advantage of being free of additional organic material that can affect the biological activity of Compound 1 or that may increase the intrinsic toxicity of the compound. Thus, in animal studies where relatively high levels of 17α-ethynyl-androstane-3α,17β-diol can be used to characterize anti-tumor activity or toxicity, e.g., about 60 mg/kg or about 100 mg/kg in mice or rats, such high levels can contribute significant amounts of a solvent such as methanol or dioxane in the solvate. Such organic molecules can affect the 17α-ethynyl-androstane-3α,17β-diol itself in vivo when such solvents, e.g., induce or otherwise modulate liver enzymes that adversely affect 17α-ethynyl-androstane-3α,17β-diol metabolism or disposition. However, anhydrates may have decreased thermodynamic stability in relationship to a corresponding hydrate, which is exhibited by hygroscopicity, particularly at high relative humidity. Hygroscopic materials may also be problematic due to decreasing potency in a drug substance due to its increasing weight as water is absorbed or to instability of a drug product or unit dosage form of the drug product (e.g., tablet crumbling).

Example 3

Determination of Form III 17α-ethynyl-5α-androstane-3α,17β-diol Unit Cell Parameters by XRPD Pattern Indexing Indexing of the high resolution XRPD pattern by a indexing method described elsewhere in the specification, provides the indexing solution given in Table 4.

TABLE 4

Indexing Solution for XRPD Pattern of Form III Compound 1

| Family and Space Group | Trigonal P3$_1$ (#144)/P3$_2$ (#145) | Trigonal/Hexagonal P3$_1$12 (#151)/P3$_2$12 (#153) P3$_1$21 (#152)/P3$_2$21 (#154) P6$_2$ (#171)/P6$_4$ (#172) |
|---|---|---|
| Z'/Z | 2/6 | 1/6 |
| a (Å) | | 10.962 |
| b (Å) | | 10.962 |
| c (Å) | | 27.356 |
| α (deg) | | 90 |
| β (deg) | | 90 |
| γ (deg) | | 120 |
| Volume (Å$^3$/cell) | | 2846.8 |
| V/Z (Å$^3$/asym. unit) | | 474.5 |
| Assumed Composition | | C$_{21}$H$_{32}$O$_2$ |
| Density (g/cm$^3$) | | 1.11 |

Figure 6:
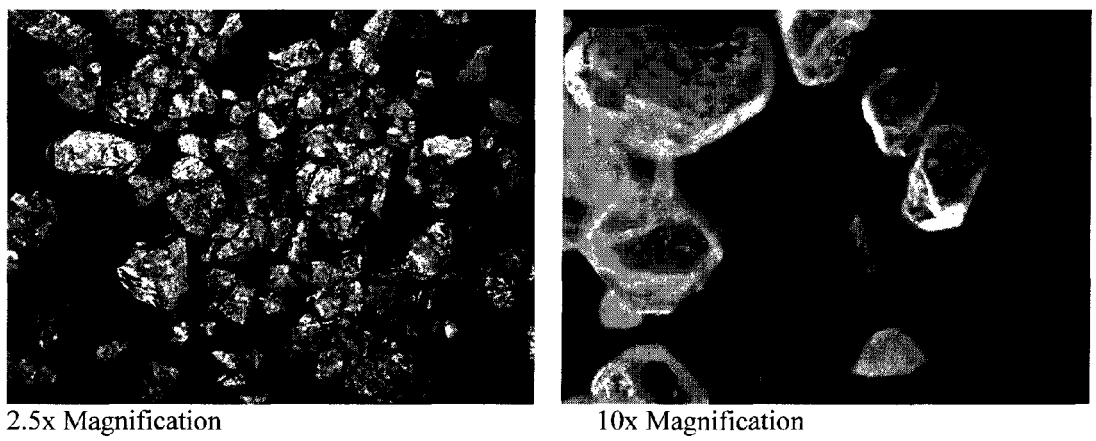
FIG. 6 provides a microscope photograph of crystals of Form III 17α-ethynyl-5α-androstane-3α,17β-diol under 10× magnification.

The crystal form for Form III 17α-ethynyl-5α-androstane-3α,17β-diol may be further indicated by the photograph of FIG. 6 obtained from microscopic examination of a sample of Form III.

Example 4

Preparation and Analysis of Crystalline Form I 17α-ethynyl-5α-androstane-3α,17β-diol (Form I Compound 1)

Form I 17α-ethynyl-5α-androstane-3α,17β-diol was prepared by dissolving Compound 1 (32 mg) methanol (200 μL) at 65° C. using an oil bat. The solution was warm filtered through 0.2 μm nylon filter into a clean vial, which was then replaced in the oil bath. Water (200 μL) was added to the solution, which caused some precipitation of solids. To increase yield, the sample was refrigerated to 5° C. The resulting solids were collected by vacuum filtration. Form I may also be prepared from Form III according to a procedure given in a subsequent example.

Figure 7:
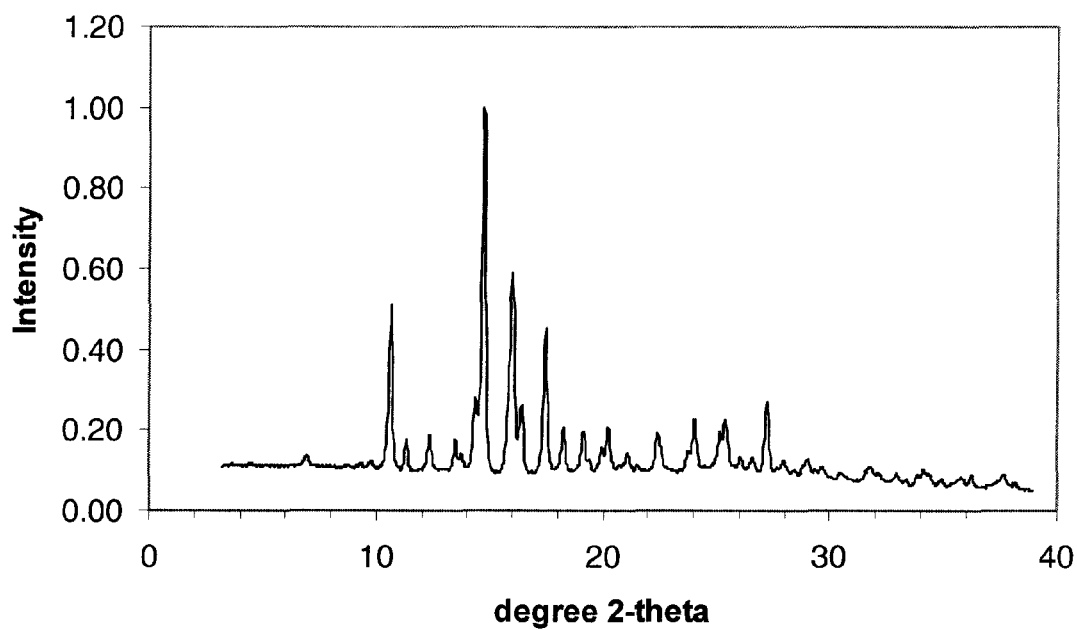
FIG. 7 provides a high resolution X-ray powder diffraction pattern of a sample comprising Form I 17α-ethynyl-5α-androstane-3α,17β-diol.

The high resolution XRPD for Form I prepared from Form III is given in FIG. 7. Listing of observed peaks for the XRPD pattern of Form I is provided in Table 5. Prominent peaks are at 10.59, 12.33, 14.29, 14.72, 16.04, 16.41, 17.49, 20.27, 24.04 and 27.21±0.10 degrees 2θ.

TABLE 5

Peak Listing for XRPD Pattern of Form I-High Resolution

| °2θ | d space (Å) | Intensity (%) |
|---|---|---|
| 6.92 ± 0.10 | 12.770 ± 0.187 | 1 |
| 8.73 ± 0.10 | 10.133 ± 0.117 | 1 |
| 9.69 ± 0.10 | 9.130 ± 0.095 | 1 |
| 10.59 ± 0.10 | 8.354 ± 0.079 | 21 |
| 11.34 ± 0.10 | 7.802 ± 0.069 | 1 |
| 12.33 ± 0.10 | 7.180 ± 0.058 | 11 |
| 13.46 ± 0.10 | 6.576 ± 0.049 | 2 |
| 13.73 ± 0.10 | 6.449 ± 0.047 | 4 |
| 14.29 ± 0.10 | 6.197 ± 0.043 | 30 |
| 14.72 ± 0.10 | 6.019 ± 0.041 | 100 |
| 15.79 ± 0.10 | 5.614 ± 0.036 | 5 |
| 15.91 ± 0.10 | 5.570 ± 0.035 | 11 |
| 16.04 ± 0.10 | 5.526 ± 0.034 | 48 |
| 16.41 ± 0.10 | 5.401 ± 0.033 | 13 |
| 17.49 ± 0.10 | 5.070 ± 0.029 | 24 |
| 17.73 ± 0.10 | 5.004 ± 0.028 | 1 |
| 18.29 ± 0.10 | 4.852 ± 0.026 | 5 |
| 19.15 ± 0.10 | 4.634 ± 0.024 | 6 |
| 19.46 ± 0.10 | 4.563 ± 0.023 | 1 |
| 19.98 ± 0.10 | 4.444 ± 0.022 | 4 |
| 20.27 ± 0.10 | 4.380 ± 0.021 | 13 |
| 21.15 ± 0.10 | 4.200 ± 0.020 | 1 |
| 22.42 ± 0.10 | 3.965 ± 0.018 | 3 |
| 22.58 ± 0.10 | 3.938 ± 0.017 | 3 |
| 23.78 ± 0.10 | 3.743 ± 0.016 | 3 |
| 24.04 ± 0.10 | 3.702 ± 0.015 | 16 |
| 24.41 ± 0.10 | 3.647 ± 0.015 | 1 |
| 24.79 ± 0.10 | 3.591 ± 0.014 | 1 |
| 25.15 ± 0.10 | 3.540 ± 0.014 | 8 |
| 25.41 ± 0.10 | 3.505 ± 0.014 | 6 |
| 25.77 ± 0.10 | 3.457 ± 0.013 | 1 |
| 26.10 ± 0.10 | 3.414 ± 0.013 | 4 |
| 26.62 ± 0.10 | 3.349 ± 0.012 | 1 |
| 27.21 ± 0.10 | 3.277 ± 0.012 | 15 |
| 27.64 ± 0.10 | 3.227 ± 0.011 | 1 |
| 27.96 ± 0.10 | 3.191 ± 0.011 | 1 |
| 28.43 ± 0.10 | 3.140 ± 0.011 | 1 |
| 28.81 ± 0.10 | 3.099 ± 0.011 | 2 |
| 29.04 ± 0.10 | 3.075 ± 0.010 | 4 |
| 29.37 ± 0.10 | 3.042 ± 0.010 | 1 |
| 29.67 ± 0.10 | 3.011 ± 0.010 | 2 |

Figure 8:
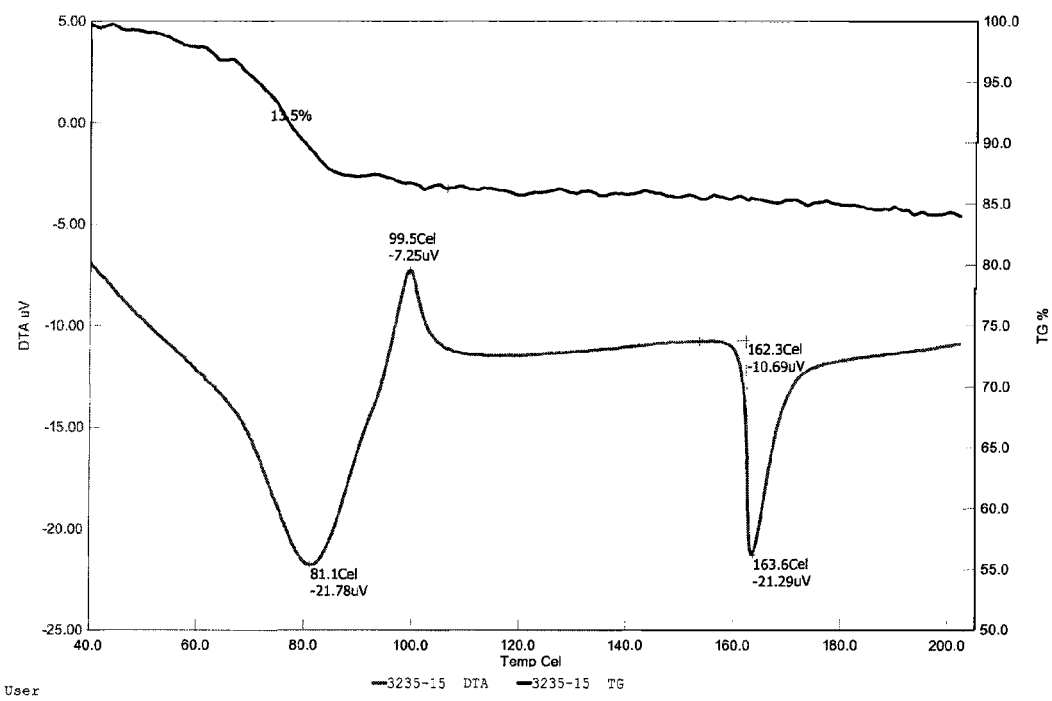
FIG. 8 provides differential scanning calorimetry and thermogravimetric analysis thermograms of a sample comprising Form I of 17α-ethynyl-5α-androstane-3α,17β-diol.

DSC and TGA thermograms for Form I 17α-ethynyl-5α-androstane-3α,17β-diol using a temperature ramp of 10° C./min, is presented in FIG. 8. The TGA thermogram shows a weight loss of about 12% between about 60° C. and about 105° C. that is accompanied by an endotherm at 88° C. in the DSC thermogram to form what may be a desolvate or partial desolvate of Form I. The DSC additionally shows a endotherm at 115° C. that is not associated with TGA weight loss and may represent lattice rearrangement(s) of a desolvated form with or without involvement of a further underlying desolvation event. The DSC further exhibits a prominent endotherm at about 164° C.

Figure 9A:
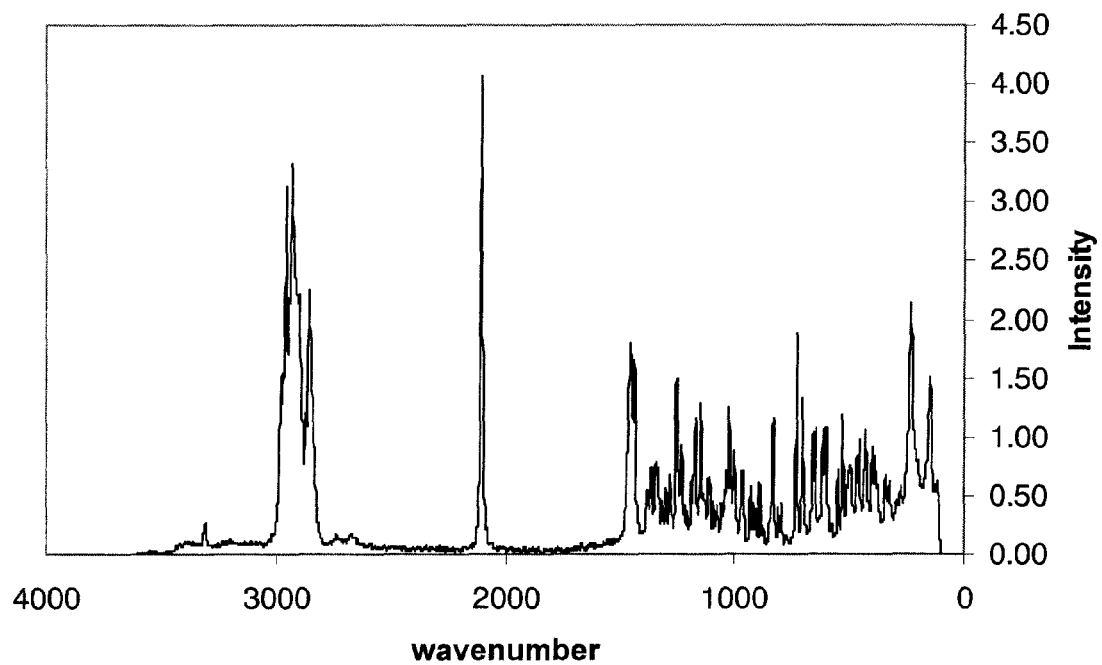
FIG. 9 provides a Raman spectrum with expanded region for a sample comprising Form I 17α-ethynyl-5α-androstane-3α,17β-diol.
Figure 9B:
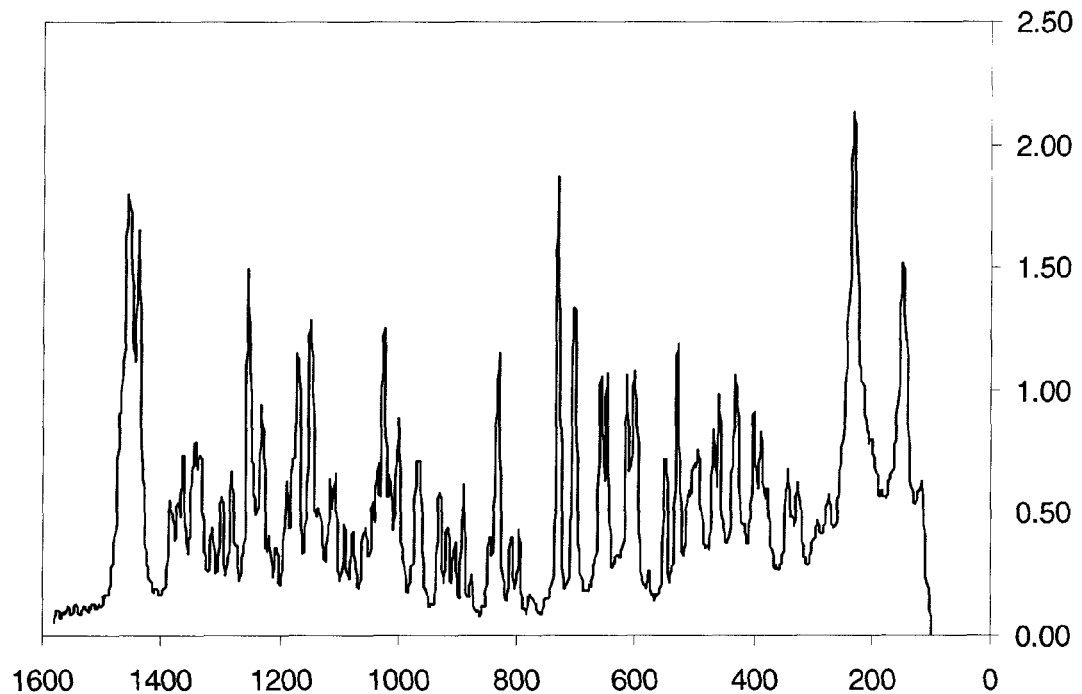

The proton FT-NMR (CDCl$_3$) spectrum of Form I 17α-ethynyl-5α-androstane-3α,17β-diol exhibits an additional resonance (δ 3.49 ppm) as compared the proton NMR spectrum of anhydrate Form III, which is due to methanol solvent. Thus NMR spectroscopy indicates that Form I is at least a methanol solvate, which is supported by the DSC/TGA data for Form I. FIG. 9 is a Raman spectroscopy spectrum of Form I 17α-ethynyl-5α-androstane-3α,17β-diol. Peak position for this Raman spectrum is given in Table 5B.

TABLE 5B

| Position (cm$^{-1}$) | Intensity |
| --- | --- |
| 147.8 | 1.523 |
| 231.3 | 2.136 |
| 324.5 | 0.628 |
| 342.3 | 0.696 |
| 387.4 | 0.830 |
| 399.5 | 0.912 |
| 429.7 | 1.063 |
| 457.3 | 0.989 |
| 466.7 | 0.837 |
| 493.6 | 0.761 |
| 528.5 | 1.191 |
| 548.5 | 0.745 |
| 600.6 | 1.100 |
| 613.9 | 1.081 |
| 647.8 | 1.070 |
| 657.6 | 1.053 |
| 702.9 | 1.378 |
| 730.1 | 1.912 |
| 796.3 | 0.430 |
| 809.2 | 0.406 |
| 831.2 | 1.151 |
| 890.3 | 0.628 |
| 904.7 | 0.382 |
| 916.2 | 0.442 |
| 929.5 | 0.581 |
| 965.5 | 0.711 |
| 1000.0 | 0.906 |
| 1024.7 | 1.275 |
| 1076.1 | 0.422 |
| 1090.8 | 0.459 |
| 1107.0 | 0.663 |
| 1112.6 | 0.647 |
| 1148.2 | 1.310 |
| 1169.8 | 1.170 |
| 1188.3 | 0.631 |
| 1230.5 | 0.940 |
| 1253.8 | 1.500 |
| 1281.1 | 0.678 |
| 1297.7 | 0.564 |
| 1314.1 | 0.451 |
| 1332.3 | 0.749 |
| 1342.5 | 0.791 |
| 1362.4 | 0.754 |
| 1383.7 | 0.567 |
| 1438.1 | 1.658 |
| 1455.5 | 1.799 |
| 2104.2 | 4.072 |
| 2856.5 | 2.259 |
| 2932.2 | 3.378 |
| 2957.5 | 3.178 |
| 2975.8 | 1.537 |
| 3306.9 | 0.266 |

Indexing of the high resolution XRPD pattern by a indexing method described elsewhere in the specification and comparison to the indexing solution of Form III, indicates that Form I is a methanol solvate with additional presence of water, which remains consistent with the DSC/TGA data obtained for Form I. Thus, Form I is a mixed methanol:water solvate of Compound 1. Karl-Fischer (KF) analysis indicates between about 5% water. Single crystal X-ray crystallography, described in a subsequent example, on Form I 17α-ethynyl-5α-androstane-3α,17β-diol confirms Form I to be a methanol-water solvate which has solvate stoichiometry of 1:1:1 Compound 1:methanol:water.

Crystalline Form I 17α-ethynyl-androstane-3α,17β-diol has the advantage of being a relatively thermodynamically stable pseudopolymorph in the presence of water. Typically, the most stable polymorphic form is chosen for commercial development to circumvent problems from changes in crystalline form that may occur during preparation of the drug substance or drug product or on storage of the drug product to ensure adequate shelf-life. However, less thermodynamically stable polymorphic forms may be desirable due to their expected greater intrinsic dissolution rates, which could positively impact oral bioavailability. Additionally, if the most stable polymorphic form is a solvate (i.e. is a pseudopolymorph) there will be toxicology considerations if the solvate is other than of water. If the solvate is of water (i.e., the pseudopolymorph is a hydrate) other considerations come into play such as expected decrease of intrinsic dissolution rate of hydrates in aqueous solution as compared to the corresponding anhydrate, which could negatively impact oral bioavailability.

Example 5

Conversion of Crystalline Form III 17α-ethynyl-5α-androstane-3α,17β-diol to Form I Form III Compound 1 (77.1 mg) was added to a glass vial, followed by MeOH (0.8 mL) and a stirring bar. The sample was placed in an oil bath at 65° C. and solids completely dissolved. Additional Form III was added so that excess solids remained and the mixture stirred for about 20 minutes. Additional MeOH (0.2 mL) was added and the mixture was hot filtered into a clean vial using a 0.2 μm nylon filter, and the filtrate was then placed in the oil bath at 65° C. Water (1 mL) was added and the mixture cooled to 20° C. over 2 hours. XRPD analysis confirms that Form III has converted to Form I as described by the immediately preceding example. Form I was also produced from a slurry of Form III in 1:1 methanol water or 3:1 methanol:water that is seeded with samples having XRPD patterns of Form IV, Form V, Form VI, Form VII and Form VIII and stirred for 5 da at about 65° C. or 7 da at about 5° C. This interconversion of Form III to Form I, in the presence of various other crystalline forms with Form I excluded indicates that Form I is the most stable polymorphic form in methanol-water compared to Forms IIII-VIII.

Example 6

Single X-Ray Crystallography of Crystalline Form I 17α-ethynyl-5α-androstane-3α,17β-diol (Form I Compound 1)

Single Crystal Preparation:
A single crystal of Form I suitable for single crystal X-ray crystalography was prepared by a slow cool of a solution of Compound 1 in MeOH-water (1:1) to refrigerator temperature.

Data Collection:
A colorless needle of $C_{22}H_{38}O_4$ ($C_{21}H_{32}O_2 \cdot 1CH_3OH \cdot 1H_2O$) having approximate dimensions of 0.25×0.08×0.06 mm, was mounted on a glass fiber in random orientation. Preliminary examination and data collection were performed with Cu K$_α$ radiation (λ=1.54184 Å) on a Rigaku Rapid II™ diffractometer equipped with a graphite crystal, incident beam monochromator. Refinements were performed on a LINUX™ PC using SHELX97™ (Sheldrick, G. M. Acta Cryst., 2008, A64, 112). Cell constants and an orientation matrix for data collection were obtained from least-squares refinement using the setting angles of 2719 reflections in the range 5°<θ<72°. The refined mosaicity from CRYSTALCLEAR™ (CrystalClear: "An Integrated Program for the Collection and Processing of Area Detector Data", Rigaku Corporation,© 1997-2002) is 0.35° indicating good crystal quality. The space group was determined by the program XPREP™ (Bruker, XPREP in SHELXTL v. 6.12., Bruker AXS Inc., Madison, Wis., USA, 2002. From the systematic presence of the following conditions: h00 h=2n; 0k0 k=2n; 00l/=2n, and from subsequent least-squares refinement, the space group was determined to be P2₁2₁2, (No. 19). The data were collected to a maximum 2θ value of 143.69°, at a temperature of 298±1 K.

Data Reduction:

Frames were integrated with CRYSTALCLEAR™. A total of 9981 reflections were collected, of which 3879 were unique. Lorentz and polarization corrections were applied to the data. The linear absorption coefficient is 0.577 mm$^{-1}$ for Mo K$_\alpha$ radiation. An empirical absorption correction using CRYSTALCLEAR™ was applied. Transmission coefficients ranged from 0.856 to 0.966. Intensities of equivalent reflections were averaged. The agreement factor for the averaging was 9.1% based on intensity.

Structure Solution and Refinement:

The structure was solved by direct methods using SIR2004 (Burla, M. C., et al. *J. Appl. Cryst.* 2005, 38, 381).

The standard deviation of an observation of unit weight (goodness-of-fit) was 0.735. The highest peak in the final difference Fourier had a height of 0.16 e/Å$^3$. The minimum negative peak had a height of −0.17 e/Å$^3$.

Figure 10:
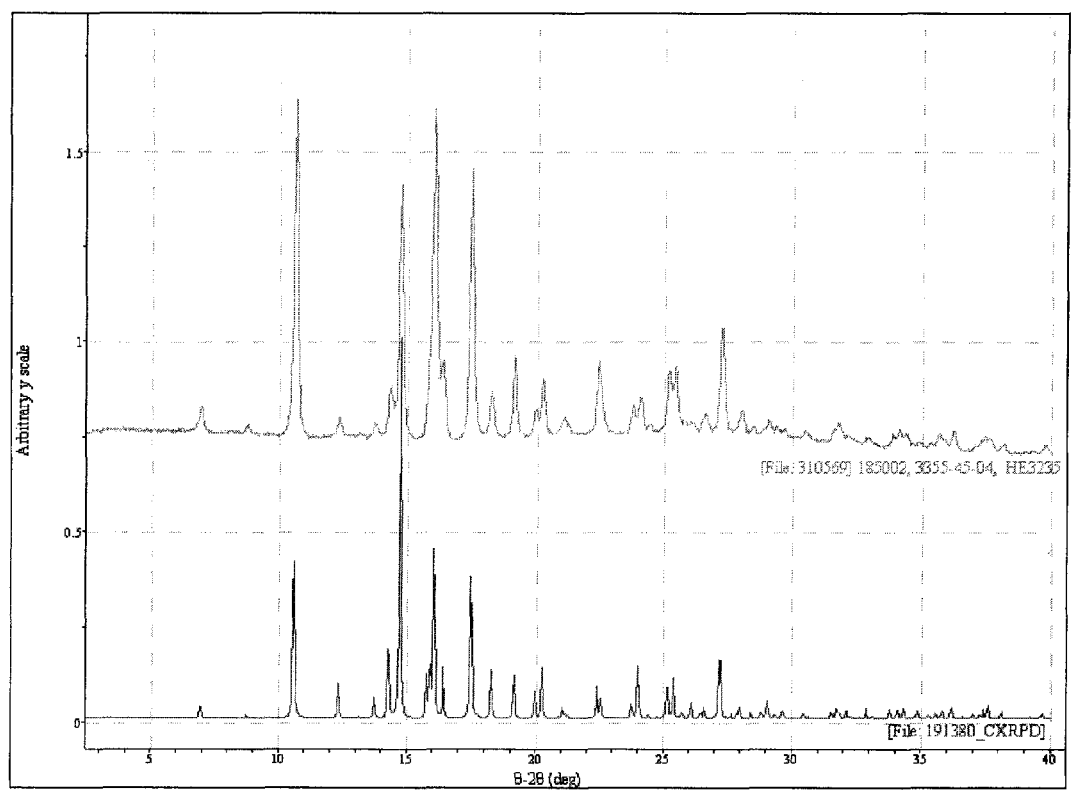
FIG. 10 provides a comparison of calculated and experimentally derived X-Ray powder diffraction patterns for Form I 17-ethynyl-5α-androstane-3α,17β-diol.

A calculated XRPD pattern was generated for Cu radiation using POWDERCELL™ 2.3 (Kraus, W.; Nolze, G. "PowderCell for Windows Version 2.3" Federal Institute for Materials Research and Testing, Berlin Germany, EU, 1999) and compared to the experimentally acquired XRPD to confirm the solution. FIG. 10 shows a comparison of the calculated XRPD pattern of Form I Compound 1 generated from single crystal data, with the experimental pattern of Form I. All peaks in the experimental pattern are represented in the calculated XRPD pattern, indicating the bulk material is likely a single phase. In general, differences in intensities between the calculated and experimental powder diffraction patterns are typically due to preferred orientation. Preferred orientation is the tendency for crystals, usually plates or needles, to be aligned with some degree of order. This preferred orientation of the sample can significantly change peak intensities, but not peak positions, in the experimental powder diffraction pattern.

Single crystal data and data collection parameters are provided in Table 6 and atomic coordinates are in Table 7. The orthorhombic cell parameters and calculated volume are: a=7.4893(4) Å, b=11.0586(8) Å, c=25.5095(15) Å, α=90.00°, β=90.00°, γ=90.00°, V=2112.7(2) Å$^3$. The formula weight of the asymmetric unit in the crystal structure of Form I Compound 1 is 366.55 amu·(formula unit)$^{-1}$ with Z=4, results in a calculated density of 1.152 g cm$^3$. The space group was determined to be P2₁2₁2₁. The quality of the structure obtained is high, as indicated by the R-value of 0.049 (4.9%). Usually R-values in the range of 0.02 to 0.06 are quoted for the most reliably determined structures Glusker, J, P., et al. "Crystal Structure Analysis: A Primer", 2$^{nd}$ ed.; Oxford University press: New York, 1985; p. 87.

TABLE 6

Crystal Data and Data Collection Parameters for Form I Compound 1

| formula | C₂₂H₃₈O₄ |
|---|---|
| formula weight | 366.55 |
| space group | P2₁2₁2₁ (No. 19) |
| a, Å | 7.4893(4) |
| b, Å | 11.0586(8) |
| c, Å | 25.5095(15) |
| V, Å$^3$ | 2112.7(2) |
| Z | 4 |

TABLE 6-continued

Crystal Data and Data Collection Parameters for Form I Compound 1

| $d_{calc}$, g cm$^{-3}$ | 1.152 |
|---|---|
| crystal dimensions, mm | 0.25 × 0.08 × 0.06 |
| temperature, K | 298. |
| radiation (wavelength, Å) | Cu K$_\alpha$ (1.54184) |
| monochromator | graphite |
| linear abs coef, mm$^{-1}$ | 0.577 |
| absorption correction applied | empirical$^a$ |
| transmission factors: min, max | 0.856, 0.966 |
| diffractometer | Nonius KappaCCD |
| h, k, l range | −9 to 6 −8 to 13 −28 to 31 |
| 2θ range, deg | 10.40-143.69 |
| mosaicity, deg | 0.35 |
| programs used | SHELXTL |
| F₀₀₀ | 808.0 |
| weighting | $1/[s^2(F_o^2) + (0.0151P)^2 + 0.0000P]$ where P = $(F_o^2 + 2F_c^2)/3$ |
| data collected | 9981 |
| unique data | 3879 |
| R$_{int}$ | 0.091 |
| data used in refinement | 3879 |
| cutoff used in R-factor calculations | $F_o^2 > 2.0s(F_o^2)$ |
| data with I > 2.0s(I) | 1501 |
| number of variables | 258 |
| largest shift/esd in final cycle | 0.00 |
| R(F$_o$) | 0.049 |
| R$_w$(F$_o^2$) | 0.077 |
| goodness of fit | 0.735 |

TABLE 7

Positional Parameters and Their Estimated Standard Deviations for Form I Compound 1

| Atom | x | y | z | U(Å$^2$) |
|---|---|---|---|---|
| O1W | −0.0438(4) | 0.8199(3) | 0.96234(12) | 0.0749(12) |
| O31 | −0.3061(4) | 1.3642(3) | 0.52670(11) | 0.0586(9) |
| O171 | −0.2218(3) | 1.8239(3) | 0.86469(9) | 0.0557(9) |
| O911 | 0.4544(4) | 1.7308(3) | 0.89214(13) | 0.0793(10) |
| C1 | −0.4852(4) | 1.5524(3) | 0.59621(10) | 0.0497(10) |
| C2 | −0.5224(4) | 1.5235(3) | 0.53815(10) | 0.0505(12) |
| C3 | −0.3548(5) | 1.4846(3) | 0.50871(12) | 0.0528(12) |
| C4 | −0.2024(4) | 1.5732(3) | 0.51687(11) | 0.0474(9) |
| C5 | −0.1678(4) | 1.5973(3) | 0.57550(11) | 0.0411(9) |
| C6 | −0.0029(4) | 1.6772(3) | 0.58395(10) | 0.0489(10) |
| C7 | 0.0429(4) | 1.6841(3) | 0.64227(10) | 0.0452(10) |
| C8 | −0.1187(4) | 1.7286(3) | 0.67539(10) | 0.0387(9) |
| C9 | −0.2860(4) | 1.6515(3) | 0.66401(10) | 0.0372(9) |
| C10 | −0.3361(4) | 1.6463(3) | 0.60464(11) | 0.0387(9) |
| C11 | −0.4445(3) | 1.6896(3) | 0.69980(10) | 0.0442(9) |
| C12 | −0.3944(4) | 1.6880(3) | 0.75845(10) | 0.0483(9) |
| C13 | −0.2289(4) | 1.7654(3) | 0.76893(11) | 0.0379(9) |
| C14 | −0.0767(4) | 1.7226(3) | 0.73391(11) | 0.0414(9) |
| C15 | 0.0892(4) | 1.7883(3) | 0.75501(11) | 0.0570(12) |
| C16 | 0.0511(4) | 1.8020(3) | 0.81432(11) | 0.0577(12) |
| C17 | −0.1400(4) | 1.7528(3) | 0.82396(12) | 0.0459(10) |
| C18 | −0.2752(4) | 1.8999(3) | 0.76101(11) | 0.0570(10) |
| C19 | −0.3946(4) | 1.7704(3) | 0.58417(10) | 0.0535(10) |
| C171 | −0.1343(6) | 1.6254(4) | 0.84154(12) | 0.0592(13) |
| C172 | −0.1224(7) | 1.5266(4) | 0.85662(14) | 0.0917(17) |
| C912 | 0.4047(6) | 1.6084(4) | 0.89996(14) | 0.0987(18) |
| H31 | −0.219(7) | 1.347(5) | 0.521(2) | 0.18(3)* |
| H171 | −0.311(5) | 1.785(4) | 0.8736(14) | 0.105(18)* |
| H1W1 | −0.081(5) | 0.767(3) | 0.9783(13) | 0.072(15)* |
| H1W2 | −0.082(5) | 0.835(4) | 0.9320(13) | 0.119(18)* |
| H911 | 0.441(7) | 1.770(4) | 0.9170(16) | 0.14(2)* |
| H3 | −0.382 | 1.481 | 0.471 | 0.064 |
| H5 | −0.140 | 1.519 | 0.591 | 0.049 |
| H8 | −0.144 | 1.813 | 0.666 | 0.046 |
| H9 | −0.255 | 1.569 | 0.674 | 0.045 |
| H14 | −0.059 | 1.637 | 0.742 | 0.050 |
| H1A | −0.594 | 1.582 | 0.612 | 0.060 |
| H1B | −0.452 | 1.478 | 0.614 | 0.060 |
| H2A | −0.610 | 1.459 | 0.536 | 0.061 |

TABLE 7-continued

Positional Parameters and Their
Estimated Standard Deviations for Form I Compound 1

| Atom | x | y | z | U(Å²) |
|---|---|---|---|---|
| H2B | −0.572 | 1.595 | 0.521 | 0.061 |
| H4A | −0.231 | 1.649 | 0.499 | 0.057 |
| H4B | −0.095 | 1.541 | 0.501 | 0.057 |
| H6A | 0.097 | 1.644 | 0.565 | 0.059 |
| H6B | −0.026 | 1.758 | 0.571 | 0.059 |
| H7A | 0.142 | 1.739 | 0.647 | 0.054 |
| H7B | 0.079 | 1.605 | 0.655 | 0.054 |
| H11A | −0.483 | 1.770 | 0.690 | 0.053 |
| H11B | −0.544 | 1.635 | 0.694 | 0.053 |
| H12A | −0.494 | 1.718 | 0.779 | 0.058 |
| H12B | −0.371 | 1.605 | 0.769 | 0.058 |
| H15A | 0.103 | 1.867 | 0.738 | 0.069 |
| H15B | 0.196 | 1.741 | 0.749 | 0.069 |
| H16A | 0.058 | 1.886 | 0.825 | 0.069 |
| H16B | 0.137 | 1.756 | 0.835 | 0.069 |
| H172 | −0.113 | 1.447 | 0.869 | 0.110 |
| H18A | −0.369 | 1.922 | 0.785 | 0.085 |
| H18B | −0.314 | 1.913 | 0.725 | 0.085 |
| H18C | −0.171 | 1.948 | 0.768 | 0.085 |
| H19A | −0.506 | 1.793 | 0.600 | 0.080 |
| H19B | −0.410 | 1.767 | 0.547 | 0.080 |
| H19C | −0.305 | 1.829 | 0.593 | 0.080 |
| H91A | 0.507 | 1.557 | 0.896 | 0.148 |
| H91B | 0.315 | 1.586 | 0.875 | 0.148 |
| H91C | 0.358 | 1.599 | 0.935 | 0.148 |

Figure 11:
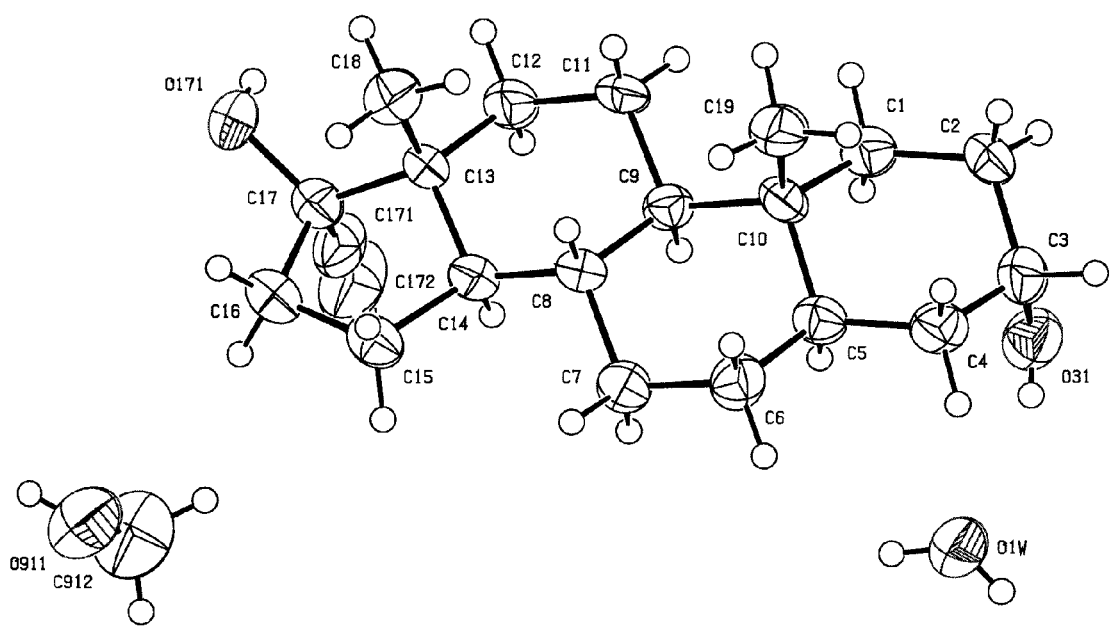
FIG. 11 is an ORTEP representation of the unit cell for crystalline Form I 17α-ethynyl-5α-androstane-3α,17β-diol determined from single crystal X-ray crystallography.

Starred atoms were refined isotropically
$U_{eq} = (1/3)\Sigma_i\Sigma_j U_{ij}a^*_i a^*_j a_i \cdot a_j$
Hydrogen atoms are included in calculation of structure factors but not refined ORTEP representation of the Form I unit cell is given by FIG. 11. The ORTEP diagram was prepared using ORTEP III™ program (Johnson, C. K. ORTEP III, Report ORNL-6895, Oak Ridge National Laboratory, TN, U.S.A. 1996; Farrugia, L. J. "OPTEP-3 for Windows V1.05", J. Appl. Cryst. 1997, 30, 565) within the PLATON software package (Spek, A. L. "PLATON. Molecular Graphics Program" Utrecht University, Utrecht, The Netherlands, 2008; Spek, A. L, J. Appl. Cryst. 2003, 36, 7). Atoms are represented by 50% probability anisotropic thermal ellipsoids. Packing diagrams were prepared using CAMERON™ modeling software (Watkin, D. J.; Prout, C. K.; Pearce, L. J. CAMERON, Chemical Crystallography Laboratory, University of Oxford, Oxford, 1996).

The molecule observed in the asymmetric unit of the single crystal structure is consistent with the molecular structure of Compound 1, although FIG. 11 displays the opposite stereochemical configuration. This configuration was arbitrarily chosen, since the absolute configuration could not be assigned as the crystal was a racemic twin. The asymmetric unit shown in FIG. 11 contains one molecule of Compound 1 with one water molecule and one methanol molecule.

Example 7

Preparation and Analysis of Crystalline Form IV
17α-ethynyl-androstane-3α,17β-diol (Form IV Compound 1)

Solids with XRPD pattern of Form IV was prepared from fast evaporation of a solution of Compound 1 in 2:3 acetonitrile:water solution or from crash precipitation of an acetonitrile solution of Compound 1 by adding water. Alternatively, Form IV was prepared form Compound 1 (34 mg) dissolved in acetonitrile (6 mL). This solution was filtered through 0.2 µm nylon filter into a clean vial, whereupon water (9 mL) was added. The resulting solution was allowed to evaporate under ambient conditions and the solids were isolated by vacuum filtration. Form IV was also prepared by dissolving Compound 1 (31 mg) into acetone (500 µL), filtering the solution through 0.2 µm nylon filter into a clean vial, and then adding water (250 µL). The solution so formed is allowed to evaporate under ambient conditions. Solids were isolated by vacuum filtration.

Needle crystal morphology was found for well formed crystals under 10× magnification with birefringence and extinction observed under polarized light due the anisotropic nature of these crystals.

Figure 12:
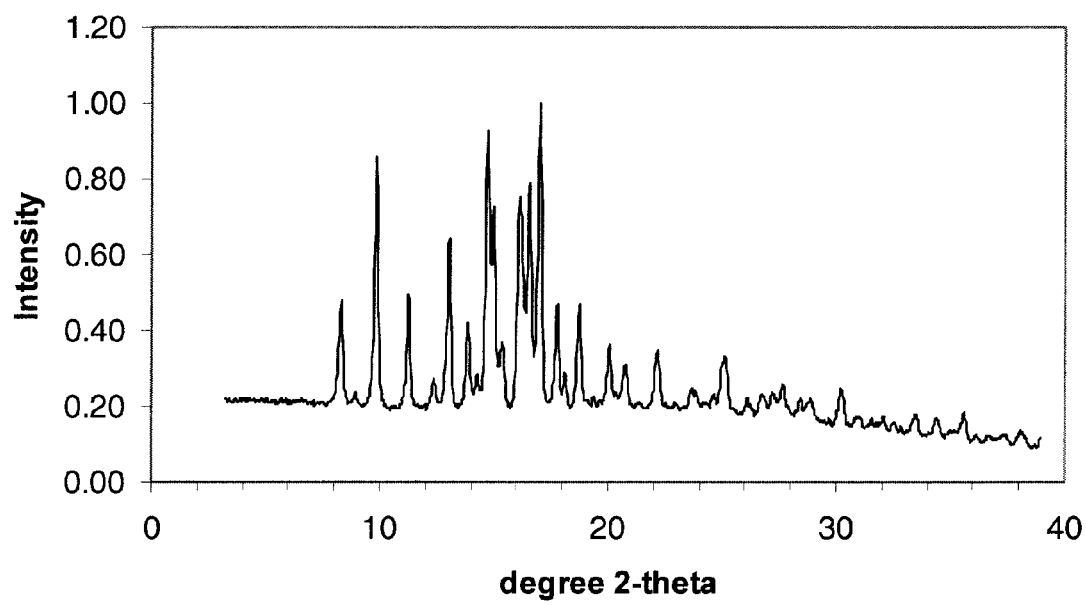
FIG. 12 provides a low resolution X-ray powder diffraction pattern of a sample comprising Form IV 17α-ethynyl-5α-androstane-3α,17β-diol.

The low resolution XRPD for Form IV prepared by the immediately preceding procedure is given in FIG. 12. Listing of observed peaks for the XRPD pattern of Form IV is provided in Table 8. Prominent peaks are at 8.31, 9.84, 11.28, 13.02, 13.86, 14.73, 15.00, 16.14, 16.53, 17.01, 17.76 and 18.72±0.10 degrees 2θ.

TABLE 8

Peak Listing for XRPD Pattern of Form IV-Low Resolution

| °2θ | d space (Å) | Intensity (%) |
|---|---|---|
| 8.31 ± 0.10 | 10.640 ± 0.129 | 35 |
| 8.91 ± 0.10 | 9.925 ± 0.112 | 5 |
| 9.84 ± 0.10 | 8.989 ± 0.092 | 82 |
| 11.28 ± 0.10 | 7.844 ± 0.070 | 39 |
| 12.36 ± 0.10 | 7.161 ± 0.058 | 10 |
| 13.02 ± 0.10 | 6.800 ± 0.052 | 57 |
| 13.86 ± 0.10 | 6.390 ± 0.046 | 28 |
| 14.25 ± 0.10 | 6.216 ± 0.044 | 11 |
| 14.73 ± 0.10 | 6.014 ± 0.041 | 93 |
| 15.00 ± 0.10 | 5.906 ± 0.039 | 66 |
| 15.36 ± 0.10 | 5.769 ± 0.038 | 22 |
| 16.14 ± 0.10 | 5.492 ± 0.034 | 70 |
| 16.53 ± 0.10 | 5.363 ± 0.032 | 75 |
| 17.01 ± 0.10 | 5.213 ± 0.031 | 100 |
| 17.76 ± 0.10 | 4.994 ± 0.028 | 35 |
| 18.12 ± 0.10 | 4.896 ± 0.027 | 11 |
| 18.72 ± 0.10 | 4.740 ± 0.025 | 34 |
| 19.35 ± 0.10 | 4.587 ± 0.024 | 4 |
| 20.04 ± 0.10 | 4.431 ± 0.022 | 21 |
| 20.31 ± 0.10 | 4.373 ± 0.021 | 6 |
| 20.76 ± 0.10 | 4.279 ± 0.020 | 15 |
| 21.36 ± 0.10 | 4.160 ± 0.019 | 2 |
| 22.14 ± 0.10 | 4.015 ± 0.018 | 20 |
| 22.95 ± 0.10 | 3.875 ± 0.017 | 3 |
| 23.67 ± 0.10 | 3.759 ± 0.016 | 8 |
| 23.79 ± 0.10 | 3.740 ± 0.016 | 7 |
| 24.27 ± 0.10 | 3.667 ± 0.015 | 3 |
| 24.63 ± 0.10 | 3.615 ± 0.015 | 6 |
| 25.14 ± 0.10 | 3.542 ± 0.014 | 18 |
| 26.10 ± 0.10 | 3.414 ± 0.013 | 6 |
| 26.73 ± 0.10 | 3.335 ± 0.012 | 7 |
| 27.24 ± 0.10 | 3.274 ± 0.012 | 7 |
| 27.66 ± 0.10 | 3.225 ± 0.011 | 12 |
| 28.41 ± 0.10 | 3.142 ± 0.011 | 8 |
| 28.92 ± 0.10 | 3.087 ± 0.010 | 7 |

Figure 13:
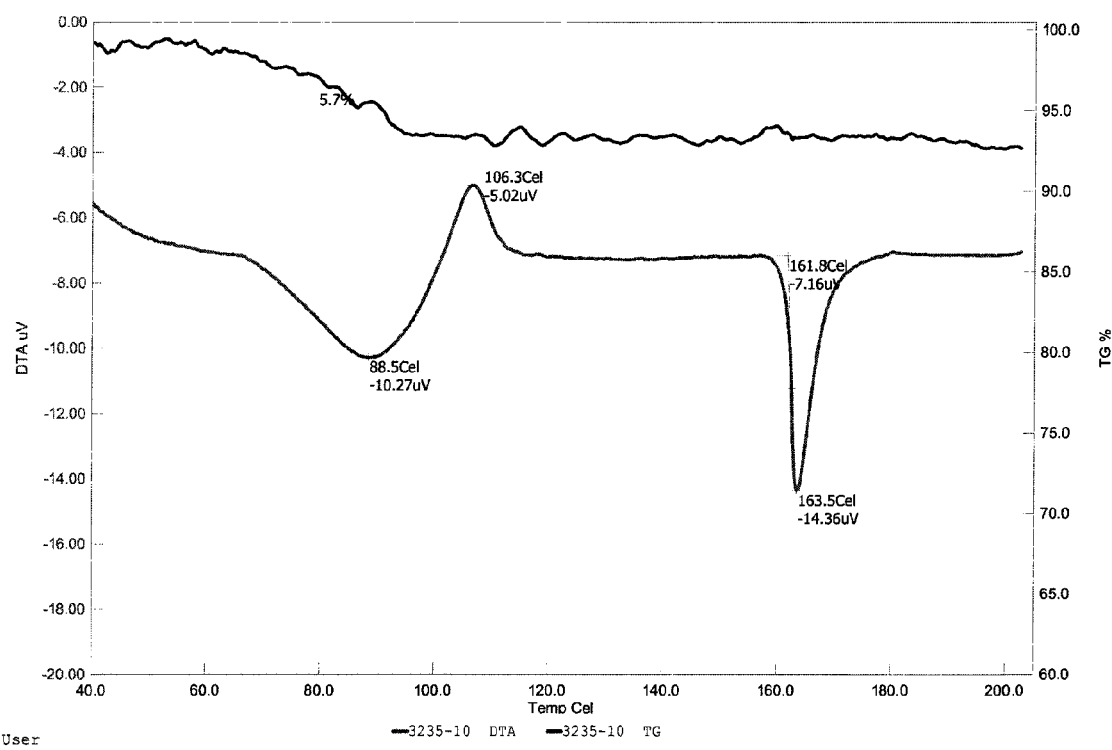
FIG. 13 provides differential thermal analysis and thermogravimetric analysis thermograms of a sample comprising Form IV 17α-ethynyl-5α-androstane-3α,17β-diol.

DTA and TGA thermograms for Form IV 17α-ethynyl-5α-androstane-3α,17β-diol using a temperature ramp of 10° C./min, are presented in FIG. 13. The TGA thermogram for Form IV shows between about 5-6% weight loss from about 60° C. to about 105° C. or about 7% weight loss from between about 40° C. to about 160° C. concomitant with a broad endotherm in the DTA thermogram centered at about 88° C. followed by an endotherm at about 106° C. These transitions are consistent with a monohydrate pseudopolymorph than undergoes transition to a more thermodynamically stable polymorphic form following its dehydration. A prominent endotherm is then observed at about 164° C.

Figure 14:
FIG. 14 provides a microscope photograph of crystals of Form IV 17α-ethynyl-5α-androstane-3α,17-diol under 2× and 10× magnification FIG. 15 provides a low resolution X-ray powder diffraction pattern of a sample comprising Form V 17α-ethynyl-5α-androstane-3α,17β-diol.
Figure 14:

Since crystalline Form IV 17α-ethynyl-androstane-3α, 17β-diol is a monohydrate, it does not contain an organic solvent such as methanol or dioxane and thus has the advantage of being free of organic material that can affect biological activity of Compound 1 or that may increase its intrinsic toxicity. The presence of water in the crystal lattice is expected to contribute to this crystal form's stability with respect to absorbing water on prolonged storage because water is already present in the crystal lattice and thus should not be as hygroscopic as the corresponding anhydrate or a lower hydrate. Based on the expected physical property of a solid with the morphology of FIG. 14, crystalline Form IV is also expected to have a favorable intrinsic dissolution rate due its high surface to volume ratio compared to other crystal morphologies. Flow characteristics for mechanical manipulations (e.g., blending), however, may not be as favorable compared to other crystal morphologies due to the directional asymmetry of the crystal shape.

Example 8

Preparation of Crystalline Form V
17α-ethynyl-androstane-3α,17β-diol (Form V
Compound 1)

Solids having the XRPD pattern of Form V was obtained by adding Form III Compound 1 (41 mg) to 2,2,2-trifluoroethanol (1600 μL). Additional Form III Compound 1 was added to form a slurry that was stirred at 30° C. for 6 days. Solids were isolated by vacuum filtration, air-dried and analyzed by XRPD. No definite crystal morphology was found for the solids so formed at 10× magnification and birefringence and extinction under polarized light was not observed, which indicates a highly disordered crystalline state for this solid state form.

Figure 15:
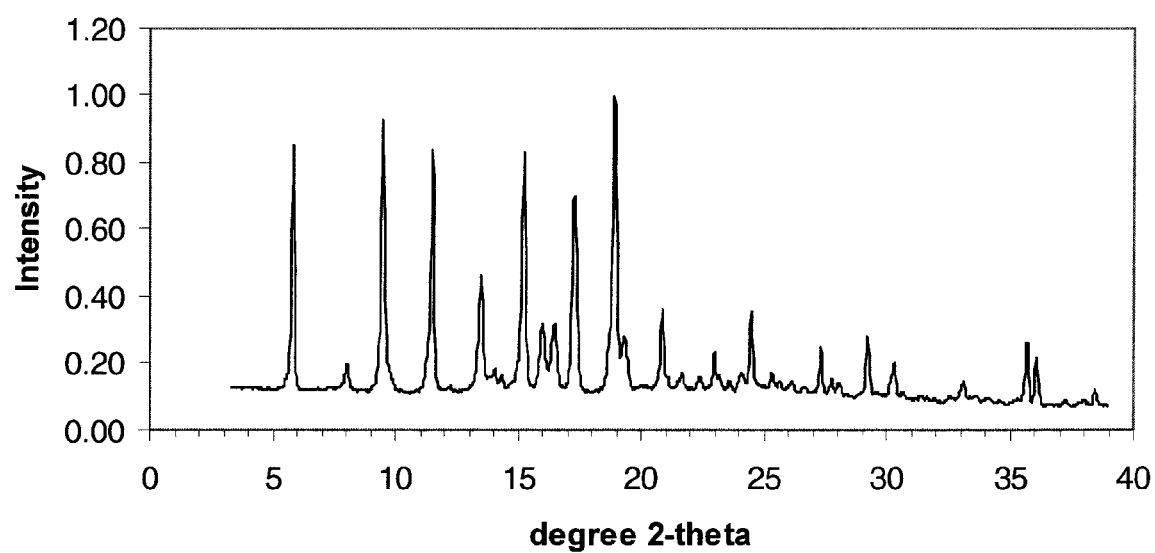

The low resolution XRPD for Form V prepared by the immediately preceding procedure is given in FIG. 15. Listing of observed peaks for the XRPD pattern of Form V is provided in Table 9. Prominent peaks are at 5.82, 9.48, 11.49, 13.50, 15.21, 17.28 and 18.93±0.10 degrees 2θ.

TABLE 9

Peak Listing for XRPD Pattern of Form V-Low Resolution

| °2θ | d space (Å) | Intensity (%) |
| --- | --- | --- |
| 5.82 ± 0.10 | 15.186 ± 0.265 | 81 |
| 8.04 ± 0.10 | 10.997 ± 0.138 | 9 |
| 9.48 ± 0.10 | 9.330 ± 0.099 | 90 |
| 11.49 ± 0.10 | 7.702 ± 0.067 | 80 |
| 12.24 ± 0.10 | 7.231 ± 0.059 | 2 |
| 13.50 ± 0.10 | 6.559 ± 0.049 | 38 |
| 14.04 ± 0.10 | 6.308 ± 0.045 | 7 |
| 14.34 ± 0.10 | 6.177 ± 0.043 | 5 |
| 15.21 ± 0.10 | 5.825 ± 0.038 | 78 |
| 15.99 ± 0.10 | 5.543 ± 0.035 | 23 |
| 16.47 ± 0.10 | 5.382 ± 0.033 | 23 |
| 17.28 ± 0.10 | 5.132 ± 0.030 | 65 |
| 18.93 ± 0.10 | 4.688 ± 0.025 | 100 |
| 19.32 ± 0.10 | 4.594 ± 0.024 | 18 |
| 20.85 ± 0.10 | 4.261 ± 0.020 | 27 |
| 21.66 ± 0.10 | 4.103 ± 0.019 | 6 |
| 22.41 ± 0.10 | 3.967 ± 0.018 | 5 |
| 23.01 ± 0.10 | 3.865 ± 0.017 | 13 |
| 23.22 ± 0.10 | 3.831 ± 0.016 | 5 |
| 23.61 ± 0.10 | 3.768 ± 0.016 | 3 |
| 24.12 ± 0.10 | 3.690 ± 0.015 | 6 |
| 24.51 ± 0.10 | 3.632 ± 0.015 | 27 |
| 25.32 ± 0.10 | 3.518 ± 0.014 | 7 |
| 25.65 ± 0.10 | 3.473 ± 0.013 | 4 |
| 26.13 ± 0.10 | 3.410 ± 0.013 | 4 |
| 26.61 ± 0.10 | 3.350 ± 0.012 | 2 |
| 27.33 ± 0.10 | 3.263 ± 0.012 | 16 |

TABLE 9-continued

Peak Listing for XRPD Pattern of Form V-Low Resolution

| °2θ | d space (Å) | Intensity (%) |
| --- | --- | --- |
| 27.75 ± 0.10 | 3.215 ± 0.011 | 5 |
| 28.05 ± 0.10 | 3.181 ± 0.011 | 5 |
| 29.25 ± 0.10 | 3.053 ± 0.010 | 21 |

TGA thermogram for Form V 17α-ethynyl-5α-androstane-3α,17β-diol using a temperature ramp of 10° C./min shows negligible weight loss from about 40° C. to about 160° C. while the DTA thermogram shows a prominent endotherm at about 164° C. and is otherwise featureless. Thus, crystalline Form V of 17α-ethynyl-androstane-3α,17β-diol is an anhydrate (i.e., has no solvent in its crystal structure). On prolonged standing, a sample of Form V was found to have undergone a polymorphic transition to Form III as evidenced by XRPD reanalysis.

Compared to a solvate containing an organic solvent, this material is expected to have the advantage of containing no organic solvent such as dioxane or methanol. In animal studies where relatively high levels of 17α-ethynyl-androstane-3α,17β-diol may be used to characterize anti-tumor or other biological activity or toxicity of the material, such high levels can contribute significant amounts of a solvent such as methanol or dioxane in the solvate. Such organic molecules can affect the 17α-ethynyl-androstane-3α,17β-diol itself in vivo when such solvents, e.g., induce or otherwise modulate liver enzymes that adversely affect 17α-ethynyl-androstane-3α,17β-diol or disposition. However, anhydrates may have decreased thermodynamic stability in relationship to a corresponding hydrate, which is exhibited by hygroscopicity, particularly at high relative humidity. Hygroscopic materials may also be problematic due to decreasing potency in a drug substance due to its increasing weight as water is absorbed or to instability of a drug product or unit dosage form of the drug product (e.g., tablet crumbling). Offsetting such disadvantages is the disordered crystalline state of Form V that may prove advantageous due to an expected higher intrinsic dissolution rate, since there will be less crystalline lattice forces to be overcome, compared to a crystalline form with highly ordered crystalline state.

Example 9

Preparation and Analysis of Crystalline Form VI
17α-ethynyl-androstane-3α,17β-diol (Form VI
Compound 1)

Form VI was prepared by dissolving Compound 1 (66 mg) in dioxane (2800 μL) with sonication. The solution was filtered through 0.2 μm nylon filter into a clean vial and allowed to evaporate under ambient conditions, yielding a gel, which was then dried under vacuum for 1 day at ambient temperature.

Irregular crystal fragments were observed, but no definite crystal morphology could be discerned at 10× magnification; however, birefringence and extinction under polarized light was observed, which indicates an anisotropic crystalline shape that may appear highly disordered in bulk amount due to the presence of significant numbers of crystal defects.

Figure 16:
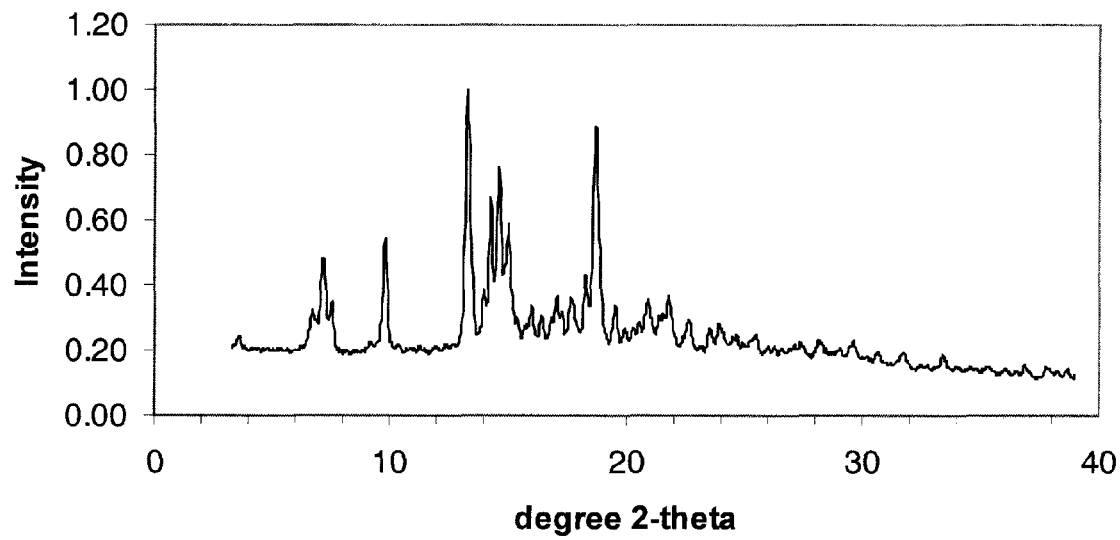
FIG. 16 provides a low resolution X-ray powder diffraction pattern of a sample comprising Form VI 17α-ethynyl-5α-androstane-3α,17β-diol.

The low resolution XRPD for Form VI prepared by the immediately preceding procedure is given in FIG. 16. Listing of observed peaks for the XRPD pattern of Form VI is provided in Table 10. Prominent peaks are 7.17, 9.78, 13.26, 14.25, 14.61, 15.000 and 18.69±0.10 degrees 2θ.

TABLE 10

Peak Listing for XRPD Pattern of Form VI-Low Resolution

| °2θ | d space (Å) | Intensity (%) |
|---|---|---|
| 3.60 ± 0.10 | 24.544 ± 0.701 | 6 |
| 6.69 ± 0.10 | 13.213 ± 0.200 | 16 |
| 7.17 ± 0.10 | 12.329 ± 0.174 | 36 |
| 7.50 ± 0.10 | 11.787 ± 0.159 | 19 |
| 9.15 ± 0.10 | 9.665 ± 0.107 | 4 |
| 9.78 ± 0.10 | 9.044 ± 0.093 | 43 |
| 13.26 ± 0.10 | 6.677 ± 0.051 | 100 |
| 13.95 ± 0.10 | 6.348 ± 0.046 | 21 |
| 14.25 ± 0.10 | 6.216 ± 0.044 | 57 |
| 14.61 ± 0.10 | 6.063 ± 0.042 | 69 |
| 15.00 ± 0.10 | 5.906 ± 0.039 | 44 |
| 15.39 ± 0.10 | 5.758 ± 0.037 | 9 |
| 15.99 ± 0.10 | 5.543 ± 0.035 | 14 |
| 16.44 ± 0.10 | 5.392 ± 0.033 | 9 |
| 16.83 ± 0.10 | 5.268 ± 0.031 | 8 |
| 17.04 ± 0.10 | 5.204 ± 0.030 | 17 |
| 17.28 ± 0.10 | 5.132 ± 0.030 | 11 |
| 17.67 ± 0.10 | 5.019 ± 0.028 | 16 |
| 18.27 ± 0.10 | 4.856 ± 0.026 | 25 |
| 18.69 ± 0.10 | 4.748 ± 0.025 | 84 |
| 19.53 ± 0.10 | 4.545 ± 0.023 | 14 |
| 19.92 ± 0.10 | 4.457 ± 0.022 | 6 |
| 20.31 ± 0.10 | 4.373 ± 0.021 | 7 |
| 20.52 ± 0.10 | 4.328 ± 0.021 | 9 |
| 20.91 ± 0.10 | 4.248 ± 0.020 | 18 |
| 21.39 ± 0.10 | 4.154 ± 0.019 | 12 |
| 21.57 ± 0.10 | 4.120 ± 0.019 | 12 |
| 21.78 ± 0.10 | 4.081 ± 0.019 | 20 |
| 22.65 ± 0.10 | 3.926 ± 0.017 | 11 |
| 23.55 ± 0.10 | 3.778 ± 0.016 | 8 |
| 23.91 ± 0.10 | 3.722 ± 0.015 | 11 |
| 24.66 ± 0.10 | 3.610 ± 0.014 | 7 |
| 25.50 ± 0.10 | 3.493 ± 0.014 | 7 |
| 26.01 ± 0.10 | 3.426 ± 0.013 | 3 |
| 26.28 ± 0.10 | 3.391 ± 0.013 | 3 |
| 26.61 ± 0.10 | 3.350 ± 0.012 | 3 |
| 27.12 ± 0.10 | 3.288 ± 0.012 | 5 |
| 27.39 ± 0.10 | 3.256 ± 0.012 | 6 |
| 28.17 ± 0.10 | 3.168 ± 0.011 | 7 |
| 29.10 ± 0.10 | 3.069 ± 0.010 | 4 |
| 29.64 ± 0.10 | 3.014 ± 0.010 | 8 |

Figure 17:
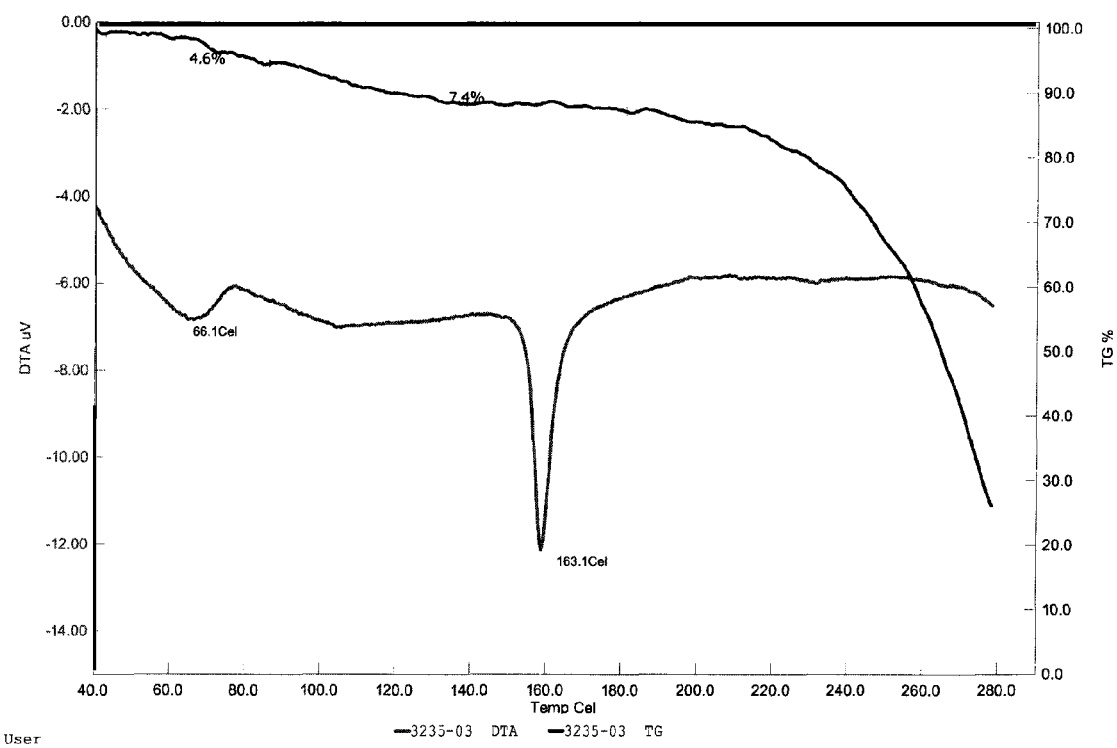
FIG. 17 provides differential thermal analysis and thermogravimetric analysis thermograms of a sample comprising Form VI 17α-ethynyl-5α-androstane-3α,17β-diol.

Thermal analysis of Form V 17α-ethynyl-5α-androstane-3α,17β-diol shown in FIG. 17 provides a TGA thermogram with about 5% weight loss from about 40° C. to about 85° C. and about 12% weight loss from about 40° C. to about 180° C. and a DTA thermogram (after calibration correction) with a broad endotherm centered at about 70° C. immediately followed by a poorly defined broad exotherm. This thermal data is consistent with a solvate that desolvates with rearrangement of the crystal lattice to form a thermodynamically more stable desolvate or partial desolvate. The DTA further shows a subsequent prominent endotherm at 164° C.

The $^1$H-NMR (CDCl$_3$) spectrum of Form VI 17α-ethynyl-5α-androstane-3α,17β-diol exhibits additional resonance (δ 3.64 ppm) as compared the proton NMR spectrum of anhydrate Form III, due to dioxane solvent. Prior to dissolution of Form VI for NMR analysis, the Form VI sample was washed with CCl$_4$ to remove non-specifically absorbed surface solvent. Proton NMR spectroscopy thus indicates Form VI is a dioxane solvate, which is supported by the DTA/TGA data, and is most likely a mono dioxane solvate based upon integration of the δ 3.64 ppm resonance and the weight loss in TGA. After prolonged standing at ambient temperature and pressure, the Form VI sample was reanalyzed by DTA/TGA and proton NMR. The thermal reanalysis now shows no TGA weight loss and no desolvation events in DTA. Furthermore, proton NMR now shows significant diminution of the δ 3.64 ppm resonance. Thus, desolvation of Form VI may occur if storage precautions are inadequate and may be accompanied by a polymorphic transition to a more thermodynamically stable form such as Form Ill.

Form VI as a dioxane solvate is expected to be useful as an internal standard for quantifying amounts of Compound 1 by proton-NMR or $^{13}$C-NMR spectroscopy in samples with an unknown content of Compound 1. Usefulness of Form VI as an internal standard in proton NMR spectroscopic analysis will be due to the presence of a singlet of relatively high intensity in the proton NMR spectrum due to eight magnetically equivalent protons contributed by the dioxane solvent that is in a precise 1:1 ratio to Compound 1 with respect to Form VI that is added to the sample to be quantified. Usefulness of Form VI as an internal standard in $^{13}$C NMR spectroscopic analysis will be due to the presence of a singlet of relatively high intensity in a proton decoupled $^{13}$C-NMR spectra due to four magnetically equivalent carbons contributed by the dioxane solvent that is in a precise 1:1 ratio to Compound 1 with respect to Form VI that is added to the sample to be quantified.

Example 10

Preparation and Analysis of Crystalline Form VII 17α-ethynyl-androstane-3α,17β-diol (Form VII Compound 1)

Form VIII Compound 1 was prepared by dissolving Compound 1 in ethanol (1.2 mL) at 47° C. The solution was evaporated to half volume under nitrogen causing a solid mass to form. Isopropyl acetate (1 mL) was then added and the solids re-dissolved with sonication. The solution was evaporated to half volume to form solids. The mixture was heated to 47° C., which caused complete dissolution and cooled to ambient temperature, causing a small amount of solids to form. The mixture so formed was refrigerated for several hours and the resulting solids were isolated by vacuum filtration.

Irregular agglomerated crystals were observed at 10× magnification that did not permit description of crystal morphology. Examination under polarized light did exhibit domains having birefringence and extinction, which indicates an anisotropic crystalline shape that may appear highly disordered in bulk amount due to the presence of significant numbers of crystal defects.

Figure 18:
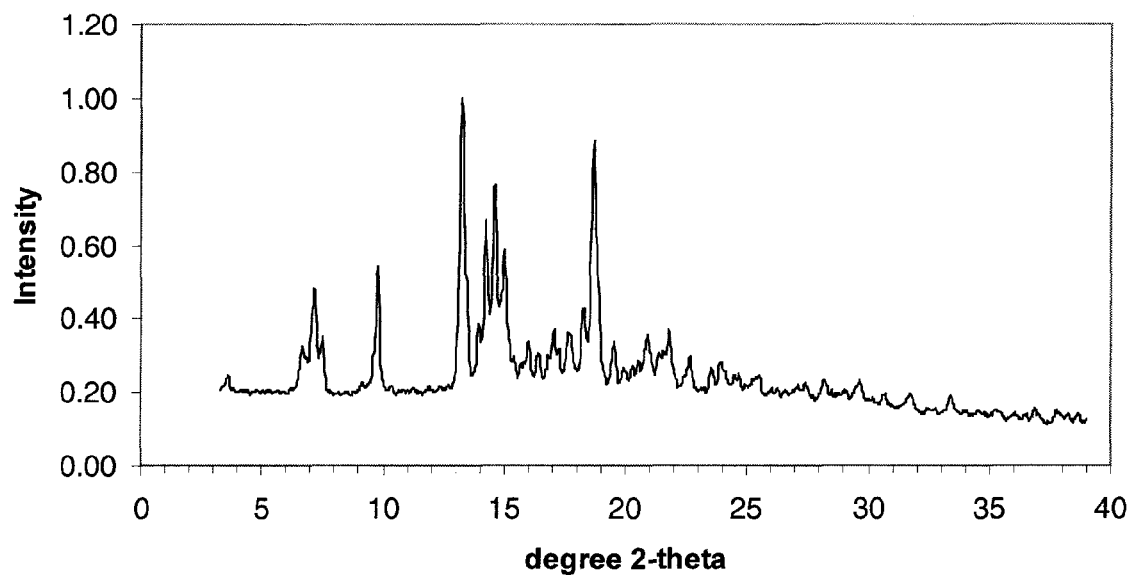
FIG. 18 provides a low resolution X-ray powder diffraction pattern of a sample comprising Form VII 17α-ethynyl-5α-androstane-3α,17β-diol.

The low resolution XRPD for Form VIII prepared from the immediately preceding procedure is given in FIG. 18. Listing of observed peaks for the XRPD pattern of Form VII is provided in Table 11. Prominent peaks are at 5.91, 9.78, 13.47, 14.16, 15.78, 17.85, 19.50 and 21.45±0.10 degrees 2θ.

TABLE 11

Peak Listing for XRPD Pattern of Form VII-Low Resolution

| °2θ | d space (Å) | Intensity (%) |
|---|---|---|
| 5.91 ± 0.10 | 14.955 ± 0.257 | 26 |
| 8.31 ± 0.10 | 10.640 ± 0.129 | 19 |
| 9.78 ± 0.10 | 9.044 ± 0.093 | 100 |
| 10.41 ± 0.10 | 8.498 ± 0.082 | 4 |
| 11.37 ± 0.10 | 7.783 ± 0.069 | 17 |
| 11.88 ± 0.10 | 7.450 ± 0.063 | 19 |
| 12.24 ± 0.10 | 7.231 ± 0.059 | 4 |
| 13.47 ± 0.10 | 6.574 ± 0.049 | 44 |
| 14.16 ± 0.10 | 6.255 ± 0.044 | 49 |
| 14.46 ± 0.10 | 6.126 ± 0.042 | 18 |
| 15.54 ± 0.10 | 5.702 ± 0.037 | 26 |
| 15.78 ± 0.10 | 5.616 ± 0.036 | 51 |

TABLE 11-continued

Peak Listing for XRPD Pattern of Form VII-Low Resolution

| °2θ | d space (Å) | Intensity (%) |
|---|---|---|
| 16.50 ± 0.10 | 5.373 ± 0.033 | 22 |
| 16.71 ± 0.10 | 5.306 ± 0.032 | 16 |
| 16.98 ± 0.10 | 5.222 ± 0.031 | 5 |
| 17.43 ± 0.10 | 5.088 ± 0.029 | 7 |
| 17.85 ± 0.10 | 4.969 ± 0.028 | 31 |
| 18.69 ± 0.10 | 4.748 ± 0.025 | 6 |
| 18.99 ± 0.10 | 4.673 ± 0.025 | 9 |
| 19.50 ± 0.10 | 4.552 ± 0.023 | 67 |
| 19.71 ± 0.10 | 4.504 ± 0.023 | 21 |
| 20.52 ± 0.10 | 4.328 ± 0.021 | 13 |
| 21.45 ± 0.10 | 4.143 ± 0.019 | 31 |
| 22.86 ± 0.10 | 3.890 ± 0.017 | 12 |
| 23.49 ± 0.10 | 3.787 ± 0.016 | 10 |
| 24.03 ± 0.10 | 3.703 ± 0.015 | 12 |
| 24.63 ± 0.10 | 3.615 ± 0.015 | 7 |
| 25.02 ± 0.10 | 3.559 ± 0.014 | 8 |
| 25.26 ± 0.10 | 3.526 ± 0.014 | 7 |
| 25.68 ± 0.10 | 3.469 ± 0.013 | 2 |
| 26.43 ± 0.10 | 3.372 ± 0.013 | 13 |
| 26.64 ± 0.10 | 3.346 ± 0.012 | 11 |
| 26.91 ± 0.10 | 3.313 ± 0.012 | 23 |
| 27.75 ± 0.10 | 3.215 ± 0.011 | 8 |
| 28.08 ± 0.10 | 3.178 ± 0.011 | 3 |
| 28.71 ± 0.10 | 3.110 ± 0.011 | 7 |

TGA thermogram for Form VII 17α-ethynyl-5α-androstane-3α,17β-diol using a temperature ramp of 10° C./min shows between about 2% to negligible weight loss from about 40° C. to about 160° C. while the DTA thermogram shows a prominent endotherm at about 164° C. and is otherwise featureless. Thus, crystalline Form VIII of 17α-ethynyl-androstane-3α,17β-diol is most likely an anhydrate (i.e., has no solvent in its crystal structure). On prolonged standing, a sample of Form VIII was found to have undergone a polymorphic transition to Form III as evidenced by XRPD reanalysis.

Compared to a solvate containing an organic solvent, this material is expected to have the advantage of containing no organic solvent such as dioxane or methanol. In animal studies where relatively high levels of 17α-ethynyl-androstane-3α,17β-diol may be used to characterize anti-tumor or other biological activity or toxicity of the material, such high levels can contribute significant amounts of a solvent such as methanol or dioxane in the solvate. Such organic molecules can affect the 17α-ethynyl-androstane-3α,17β-diol itself in vivo when such solvents, e.g., induce or otherwise modulate liver enzymes that adversely affect 17α-ethynyl-androstane-3α,17β-diol or disposition. However, anhydrates may have decreased thermodynamic stability in relationship to a corresponding hydrate, which is exhibited by hygroscopicity, particularly at high relative humidity. Hygroscopic materials may also be problematic due to decreasing potency in a drug substance due to its increasing weight as water is absorbed or to instability of a drug product or unit dosage form of the drug product (e.g., tablet crumbling).

Example 11

Preparation and Analysis of Crystalline Form VIII 17α-ethynyl-androstane-3α,17β-diol (Form VIII Compound 1)

Form VIII was prepared from slow evaporation of a dichloromethane solution of Compound 1. Visual examination under 10× magnification shows irregular shaped crystal fragments. The low resolution XRPD for Form VIII prepared by the immediately preceding procedure is given in FIG. 19. Listing of observed peaks for the XRPD pattern of Form VIII is provided in Table 12. Prominent peaks are at 11.13, 15.96, 16.62, 17.76 and 18.75±0.10 degrees 2θ.

TABLE 12

Peak Listing for XRPD Pattern of Form VIII-Low Resolution

| °2θ | d space (Å) | Intensity (%) |
|---|---|---|
| 9.39 ± 0.10 | 9.419 ± 0.101 | 10 |
| 10.11 ± 0.10 | 8.750 ± 0.087 | 11 |
| 11.13 ± 0.10 | 7.950 ± 0.072 | 35 |
| 13.50 ± 0.10 | 6.559 ± 0.049 | 6 |
| 14.76 ± 0.10 | 6.002 ± 0.041 | 9 |
| 15.96 ± 0.10 | 5.553 ± 0.035 | 100 |
| 16.62 ± 0.10 | 5.334 ± 0.032 | 26 |
| 17.76 ± 0.10 | 4.994 ± 0.028 | 31 |
| 18.75 ± 0.10 | 4.733 ± 0.025 | 28 |
| 19.08 ± 0.10 | 4.652 ± 0.024 | 14 |
| 20.16 ± 0.10 | 4.405 ± 0.022 | 5 |
| 22.29 ± 0.10 | 3.988 ± 0.018 | 10 |
| 22.86 ± 0.10 | 3.890 ± 0.017 | 11 |
| 23.73 ± 0.10 | 3.750 ± 0.016 | 22 |
| 24.00 ± 0.10 | 3.708 ± 0.015 | 10 |
| 24.30 ± 0.10 | 3.663 ± 0.015 | 22 |
| 25.17 ± 0.10 | 3.538 ± 0.014 | 7 |
| 25.38 ± 0.10 | 3.509 ± 0.014 | 9 |
| 25.74 ± 0.10 | 3.461 ± 0.013 | 8 |
| 26.16 ± 0.10 | 3.407 ± 0.013 | 12 |
| 27.96 ± 0.10 | 3.191 ± 0.011 | 10 |
| 28.41 ± 0.10 | 3.142 ± 0.011 | 22 |
| 29.85 ± 0.10 | 2.993 ± 0.010 | 6 |

TGA thermogram for Form VIII 17α-ethynyl-5α-androstane-3α,17β-diol using a temperature ramp of 10° C./min shows negligible weight loss from about 40° C. to about 160° C. while the DTA thermogram shows a prominent endotherm at about 164° C. and is otherwise featureless. Thus, crystalline Form VIII of 17α-ethynyl-androstane-3α,17β-diol is most likely an anhydrate (i.e., has no solvent in its crystal structure).

Compared to a solvate containing an organic solvent, this material is expected to have the advantage of containing no organic solvent such as dioxane or methanol. In animal studies where relatively high levels of 17α-ethynyl-androstane-3α,17β-diol may be used to characterize anti-tumor or other biological activity or toxicity of the material, such high levels can contribute significant amounts of a solvent such as methanol or dioxane in the solvate. Such organic molecules can affect the 17α-ethynyl-androstane-3α,17β-diol itself in vivo when such solvents, e.g., induce or otherwise modulate liver enzymes that adversely affect 17α-ethynyl-androstane-3α,17β-diol or disposition. However, anhydrates may have decreased thermodynamic stability in relationship to a corresponding hydrate, which is exhibited by hygroscopicity, particularly at high relative humidity. Hygroscopic materials may also be problematic due to decreasing potency in a drug substance due to its increasing weight as water is absorbed or to instability of a drug product or unit dosage form of the drug product (e.g., tablet crumbling). Due to its disordered crystalline state Form VIII may be expected to have a greater intrinsic dissolution rate compared to more ordered crystalline forms.

Example 12

Preparation and Analysis of Amorphous 17-ethynyl-5α-androstane-3α,17β-diol (Amorphous Compound 1)

Compound 1 (52.0 mg) was dissolved in 200 μL of methanol by heating in an 80° C. water bath. The solution was allowed to reach room temperature whereupon 20 μL of water was added with swirling. The solid so formed was filtered, washed with cold methanol and dried under vacuum to give 24.3 mg of the title material.

Figure 20:
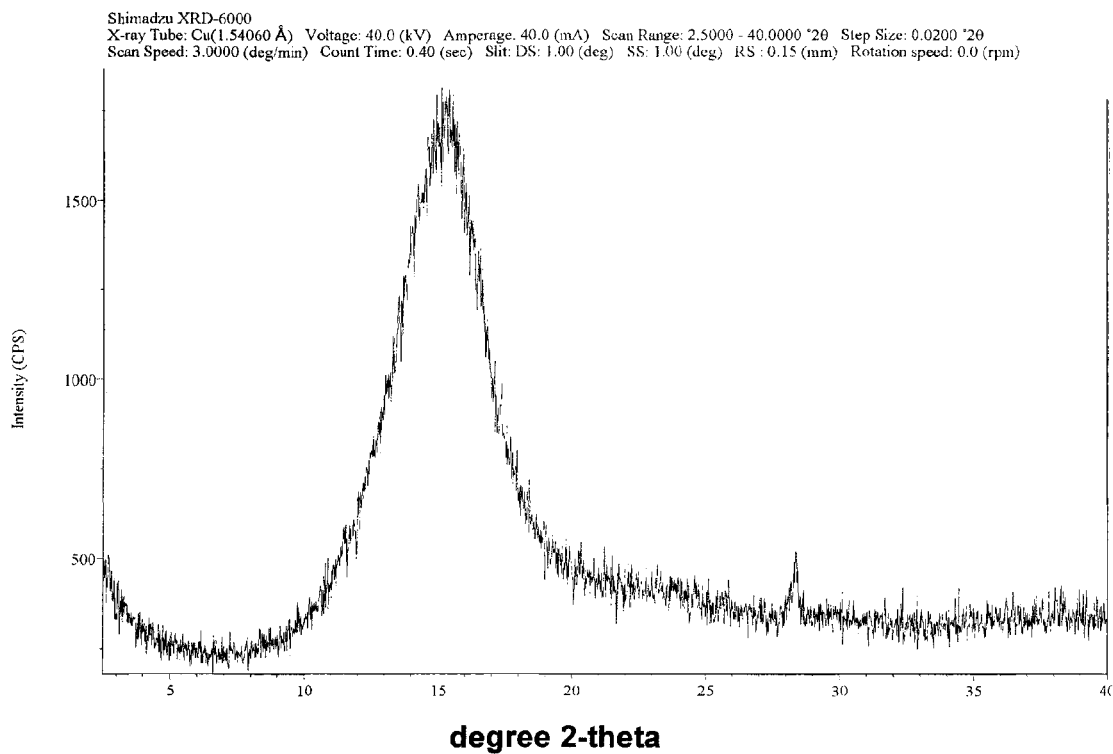
FIG. 20 provides a low resolution X-ray powder diffraction pattern of a sample comprising amorphous 17α-ethynyl-5α-androstane-3α,17β-diol substantially free of crystalline 17α-ethynyl-5α-androstane-3α,17β-diol.
Figure 21:
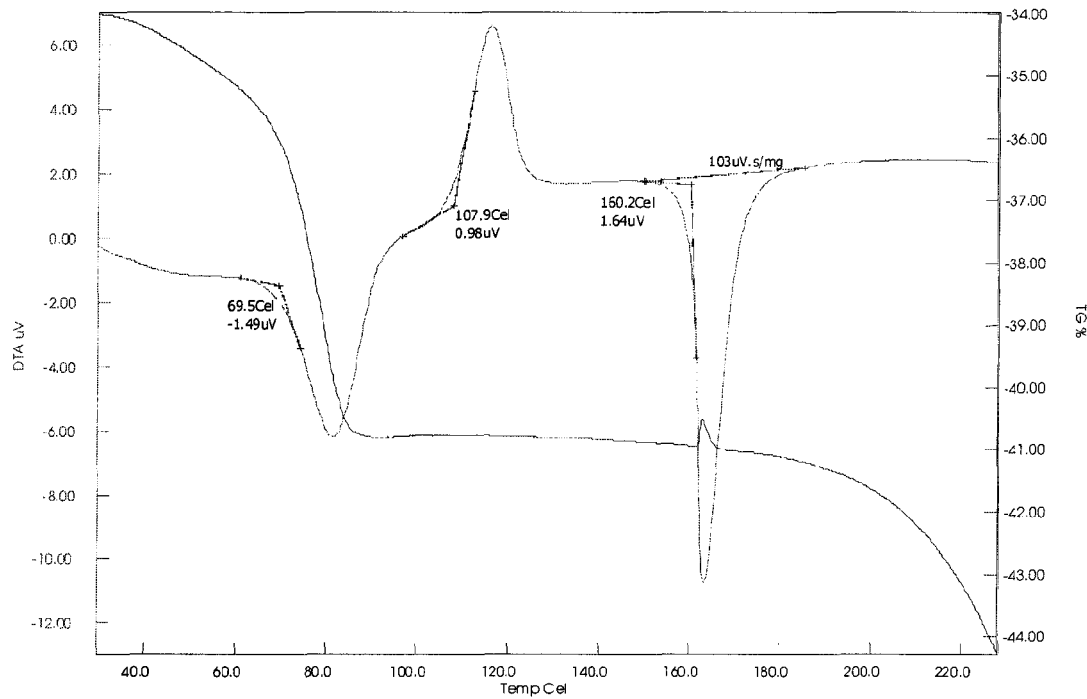
FIG. 21 provides a thermogravimetric analysis thermogram and a thermal differential analysis thermogram of a sample comprising amorphous 17α-ethynyl-5α-androstane-3α,17β-diol substantially free of crystalline 17α-ethynyl-5α-androstane-3α,17β-diol.

The XRPD pattern given FIG. 20 is a halo with no distinctive peaks, which is indicative of amorphous material. The DTA/TGA thermograms provided in FIG. 21, show an endothermic event at about 81° C. in the DTA trace with about 7% decrease of weight in the TGA thermogram from about 35° C. to about 60° C., using a temperature ramp of 10 C/min. These thermal events are indicative of desolvation. An exothermic event in the DTA trace is subsequently observed at about 120° C., which indicates a transition from amorphous to a thermodynamically stable polymorph has occurred. This polymorph, presumed to be Form III, then exhibits a prominent endotherm at about 163° C.

Amorphous compound 1, with varying degrees of crystallinity was also obtained form melt-quenching Form III according to the following procedure. Form III was lightly crushed with a spatula in a vial that was then placed in an oilbath set at 175° C. A nitrogen stream was run through the vial and the vial kept in the oilbath until the sample had melted. The vial was then removed and quickly placed in a bath containing dry ice with acetone. The sample was placed in a freezer under desiccant and analyzed by XRPD for crystallinity.

The propensity of amorphous material to convert to various crystalline forms was studied by vapor stressing melt-quenched Compound 1, prepared from Form III by the immediately preceding procedure. Studies at high humidity indicate that amorphous Compound 1 will convert back to Form III further indicating that Form III is the most thermodynamically stable polymorphic form provided Form III is not exposed to methanol-water.

Example 13

Preparation of Formulations Comprising 17α-ethynyl-5α-androstane-3α,17β-diol in Solid State Form The following Table are lists of ingredients used in preparation of capsule formulations containing Compound 1 in solid state form.

TABLE 13

Formulation Containing 25 mg Solid State Compound 1

|  | % w/w | mg/capsule |
| --- | --- | --- |
| Drug Substance |  |  |
| Compound 1 micronized | 13.9 | 25.0 |
| Excipients |  |  |
| Sodium lauryl sulfate, NF | 10.0 | 18.0 |
| Microcrystalline cellulose, NF (Avicel PH 102) | 65.6 | 118 |
| Crospovidone, NF (Polypasdone XL-10) | 10.0 | 18.0 |
| Magnesium stearate, NF | 0.5 | 1.0 |
| Total | 100 | 180 |
| Hard gelatin capsule # 2 |  |  |

TABLE 14

Formulation Containing 5 mg Compound 1 in Solid State Form

|  | % w/w | mg/capsule |
| --- | --- | --- |
| Drug Substance |  |  |
| Compound 1 micronized | 2.8 | 5.0 |
| Excipients |  |  |
| Sodium lauryl sulfate, NF | 10.0 | 18.0 |
| Microcrystalline cellulose, NF (Avicel PH 102) | 76.7 | 138 |
| Crospovidone, NF (Polypasdone XL-10) | 10.0 | 18.0 |
| Magnesium stearate, NF | 0.5 | 1.0 |
| Total | 100 | 180 |
| Hard gelatin capsule # 2 |  |  |

The following are ingredient lists used in preparation of a suspension formulation of Compound 1 in solid state form.

TABLE 15

Suspension Formulation Containing Compound 1 in Solid State Form

|  | % w/w |
| --- | --- |
| Drug Substance |  |
| Compound 1 micronized | 2-10 |
| Excipients |  |
| Polysorbate 80 | 2.0 |
| Carboxymethycellulose (CMC) | 0.1 |
| Sodium Chloride | 0.9 |
| Phenol | 0.05 |
| Deionized water | Remainder |

In the formulations above and in the following examples solid state forms of Compound 1 (e.g. amorphous or crystalline Form III) are preferably micronized to a mean volume weighted particle size (Dv, 50) of between about 3 to about 100 microns prior to blending with excipients. In one embodiment, Polymorph Form III is micronized to give a particle size with (Dv, 90)=10 μm (particle size that contains 90% (volume weighted) of all the particles). Selection of appropriate particle size is a tradeoff between improved bioavailability for a solid state form of Compound 1 in a given formulation due to improved dissolution rate of solid state Compound 1 and increased manufacturing cost of the formulation as particle size decreases. For example, particle sizes with a mean volume weighted particle size or average diameter of less than about 3 microns typically requires fluid bed micronization (for example, see Julia Z. H, et al. "Fluid bed granulation of a poorly water soluble, low density, micronized drug: comparison with high shear granulation" *Int. J. Pharm.* 237 (1-2): 1-14 (2002), which is more costly than jet milling to a larger particle size and is a process more difficult to scale up.

With dosage strengths of less than 5 mg (e.g., 1 mg) pre-blending of micronized Compound 1 with a surface active agent such as sodium lauryl sulfate is sometimes conducted prior to blending with the remaining excipients in order to obtain a uniform distribution of Compound 1 within the formulation.

Example 14

Prostate Cancer

Treatment of Androstenedione (AED)-stimulated CaP in a Tumor Model using a Formulation Prepared from Crystalline Form III.

Castrated SCID mice (six week-old) were implanted with a 5 mg AED, 60-day time-release pellet (Innovative Labs, Sarasota Fla.). After three days, all mice were injected subcutaneously in the right flank with 100 µL of $7.5 \times 10^6$ LNCaP tumor cells in phenol red-free RPMI mixed 1:1 with Matrigel. Tumor volumes were measured weekly and calculated as a2×b/2 with a being the width and b the length of the tumor in millimeters (reported as $mm^3$).

To test the effect of dose on tumor incidence, a total of 48 castrated male SCID mice were implanted with LNCaP tumor cells as described, and the mice were randomly divided into 4 groups of 12 animals each to provide vehicle control (30% cyclodextrin-sulfobutylether in water) group and treatment groups using 4 mg/mouse/day, 1 mg/mouse/day, and 0.4 mg/mouse/day). Treatment groups used a liquid formulation prepared by dissolving a solid state form of 17α-ethynyl-androst-5-ene-3α,17β-diol (Compound 1) in vehicle, which provided 20 mg Compound 1 per mL in 30% cyclodextrin-sulfobutylether in water. The liquid formulation so prepared was administered 24 hours after tumor inoculation as a 200 µL intraperitoneal (ip) injection. All animals were dosed daily for 28 consecutive days and tumor volumes were measured weekly.

Figure 22:
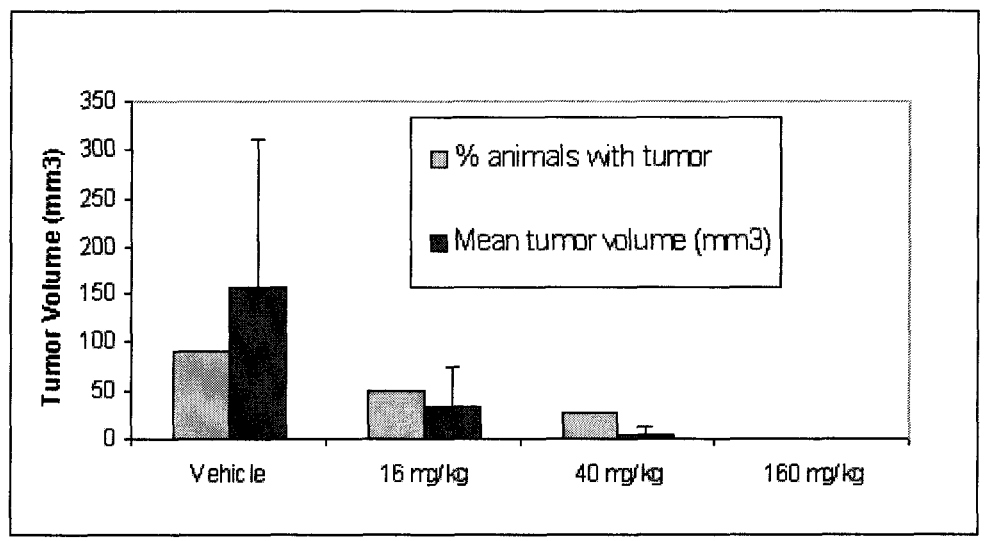
FIG. 22 presents effects of a formulation prepared from crystalline 17α-ethynyl-5α-androstane-3α,17β-diol on tumor incidence in a prostate cancer tumor model showing evolution of tumor volume by treatment and day since the start of treatment.

The results of this study (FIG. 22) showed a significant reduction in tumor incidence (compared to vehicle) in the two highest dose groups, (1 mg, p=0.006, n=11; 4 mg, p<0.001, n=12), with decreases in tumor volume apparent in all three dose groups (FIG. 9). There was a statistically significant delay in the time to a measurable tumor volume in the three treated groups (p<0.01). The mean tumor volumes in the animals that developed tumors were also affected, 157 $mm^3$ vs 0 $mm^3$, 4 $mm^3$, 34 $mm^3$ (vehicle then descending dose).

To test the effect of a Compound 1 on established LNCaP tumors, 36 castrated SCID mice received AED pellets and were inoculated with LNCaP tumors and monitored as described above. Once the tumors reach 15-25 $mm^3$, the mice were paired by tumor volume, and each mouse in a pair was assigned to the vehicle or 4 mg/mouse/day Compound 1 group. Animals were dosed once a day for three weeks.

Figure 23:
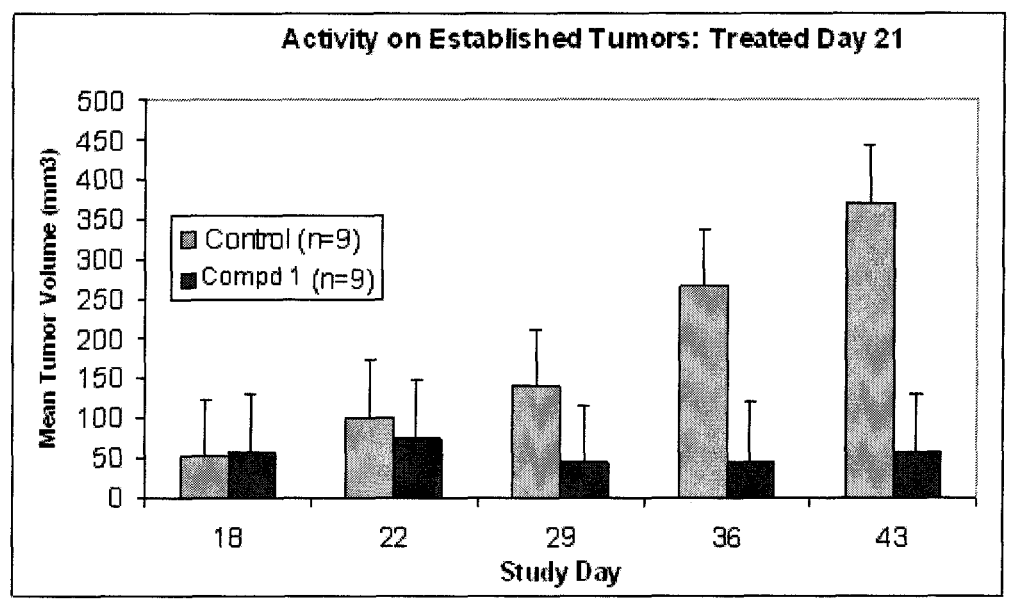
FIG. 23 presents effects of a formulation prepared from crystalline 17α-ethynyl-5α-androstane-3α,17β-diol on established tumors in a prostate cancer model by showing the evolution of tumor volume by treatment and day since the start of treatment.

The results of this experiment are shown in FIG. 23. Vehicle treated animals showed a progressive increase in tumor volume over the course of the study. In contrast, treatment with Compound 1 significantly blocked the growth of tumors (p<0.001). Significant differences in tumor volumes between the control and treated groups were observed by the first week and were maintained through the course of this study (p<0.001). A significantly greater percent of mice in the treatment group reduced their tumor volumes by 20% or more (p<0.0294). No tumor reduction was seen in vehicle group. In addition, two mice in the Compound 1 group had a tumor that became non-measurable by Day 15.

Statistical analysis: Time to first measurable tumor volume was analyzed via Kaplan-Meier product limit estimates, with the exact log-rank test applied to test for the significance of the difference. Reduction of tumor volume is defined as a reduction in volume of at least 20% of the baseline volume, persisting to the end of the study. To detect the difference between active and control group, Fisher's exact test and exact 95% CI for the difference was applied. A tumor of non-measurable volume is a tumor that, with the methodology at hand, measures 0 to the end of the study. The growth rate of a tumor was also analyzed via the mixed model.

Example 15

Induction of Apoptosis in Cells Undergoing Hyperproliferation

The following study determined the effect of a formulation prepared with a polymorph of 17α-ethynyl-androst-5-ene-3α,17β-diol (crystalline Form III of Compound 1) on a prostate tumor cell line.

LNCaP Cells ($5 \times 10^5$) were seeded in phenol-red free RPMI with 5% hormone depleted charcoal stripped serum (CSS) in 6-well plates and allowed to adhere overnight, then cultured in fetal bovine serum (FBS) or CSS with or without 50 nM Compound 1 for four days. At the end of the incubation period, floating and adherent cells were harvested for cell cycle analysis. LNCaP cells were resuspended in a 10 mg/mL solution of 4,6-diamidino-2-phenylindole (DAPI) and 0.1% NP-40 in a Tris-buffered saline solution (pH 7.0) and analyzed using an Influx cytometer (Cytopiea, Seattle, Wash.). Analyses were performed with MultiCycle software (Phoenix Flow Systems, San Diego, Calif.). The Annexin V-FITC Apoptosis Detection Kit (Calbiochem, La Jolla, Calif.) was used according to the instructions of the manufacturer to detect apoptosis.

Figure 24:
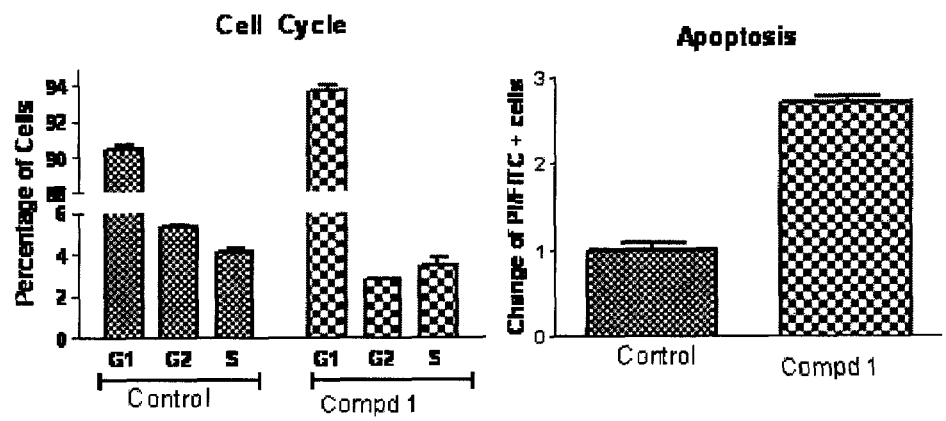
FIG. 24 presents inhibition of cell cycle and induction of apoptosis in prostate cancer cells undergoing proliferation after treatment with a formulation prepared from crystalline 17α-ethynyl-5α-androstane-3α,17β-diol.

FIG. 24 shows a rise in the number of cells in G1 after incubation of LNCaP cells with Compound 1. This accumulation of cells in G1 was accompanied by an increase in the percentage of apoptotic LNCaP cells after exposure to Compound 1 These data suggest is not merely blocking the growth of LNCaP but acting as a cytotoxic agent for LNCaP cells.

Example 16

Breast Cancer: MNU Stimulated Tumor Model

The following study determined the effect of a formulation prepared with a polymorph of 17α-ethynyl-androst-5-ene-3α,17β-diol (Crystalline Form III of Compound 1) on the rate of growth and incidence of breast tumors induced by the administration of the carcinogen N-methyl-nitrosourea (NMU). Additionally, the activity of Compound 1 was compared to TAMOXIFEN™ ((Z)-2-[4-(1,2-diphenylbut-1-enyl)phenoxy]-N,N-dimethyl-ethanamine), ARIMIDEX™ (anastrozole) and TAXOTERE™ (docetaxel), which are drugs currently used to treat breast cancer.

Seven week old female Lewis rats (150 animals, 104 required for the study) were anesthetized with isoflurane for NMU administration. NMU was the administered ip. at a dose of 50 mg/Kg. Mammary tumors that developed were measured using a vernier caliper with two axes of the tumor measured in cm. Treatment commenced using a liquid formulation of Compound 1, prepared by dissolving crystalline Form I in vehicle, when rats have a tumor volume of 0.5 cm×0.5 cm (at about 12-20 week of age). Treatment continued for 28 consecutive days, followed by 28 days of observation. Mammary tumors were removed when a size of 2 cm×2 cm was reached in accordance with local institutional guidelines.

The experimental groups were Negative control group (no treatment), Vehicle control group (30% cyclodextrin-sulfobutylether in water), two treatment groups (8 mg/rat and 4 mg/rat), three standard therapy groups using an estrogen blocker (TAMOXIFEN™), an aromatase inhibitor (ARIMI- DEX), a cytotoxic agent (TAXOTERE™) and a combination treatment group receiving Compound 1 (8 mg/kg) and TAXOTERE™.

Figure 25:
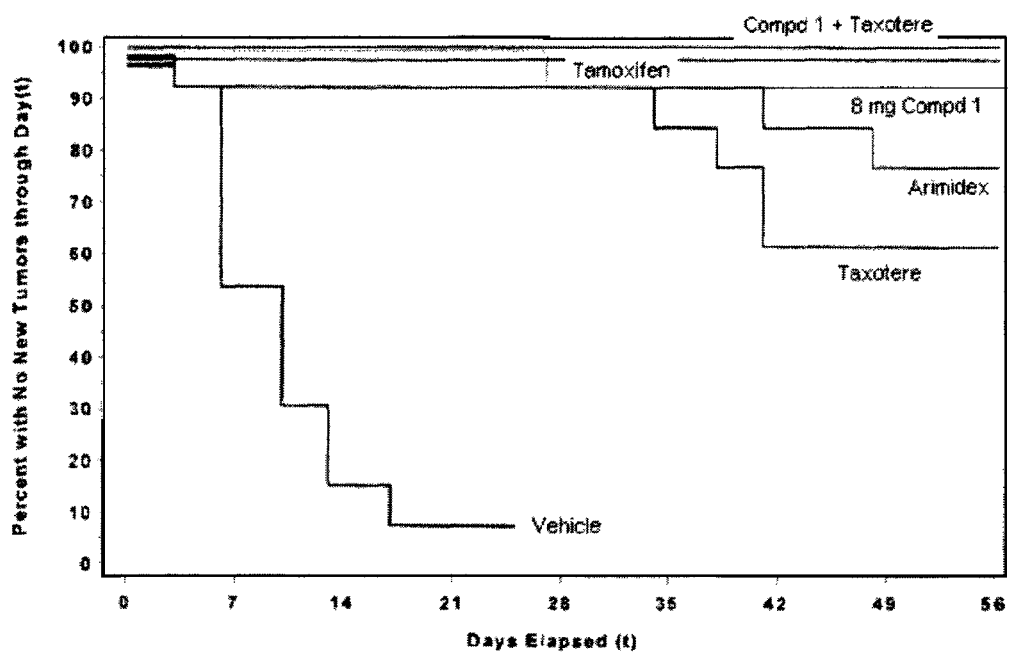
FIG. 25 present effects of a formulation prepared from crystalline 17α-ethynyl-5α-androstane-3α,17β-diol on distribution of time to new tumor following first day of dosing in a breast cancer model

FIG. 25 shows the percent of animals with new tumors plotted against elapsed time from first day of dosing. This plot shows a longer time to a new tumor as compared to vehicle (p<0.001). Median times to new tumor are 10 days with vehicle compared to at least 56 days with Compound 1, which represents at least a five fold delay to the occurrence of a second tumor that is attributable to Compound 1. The plot also indicates that Compound 1 at 4 mg outperformed TAXOTERE™ (p=0.042) and Compound 1 at 8 mg plus TAXOTERE™ is better than TAXOTERE™ alone (p=0.0385).

Figure 26:
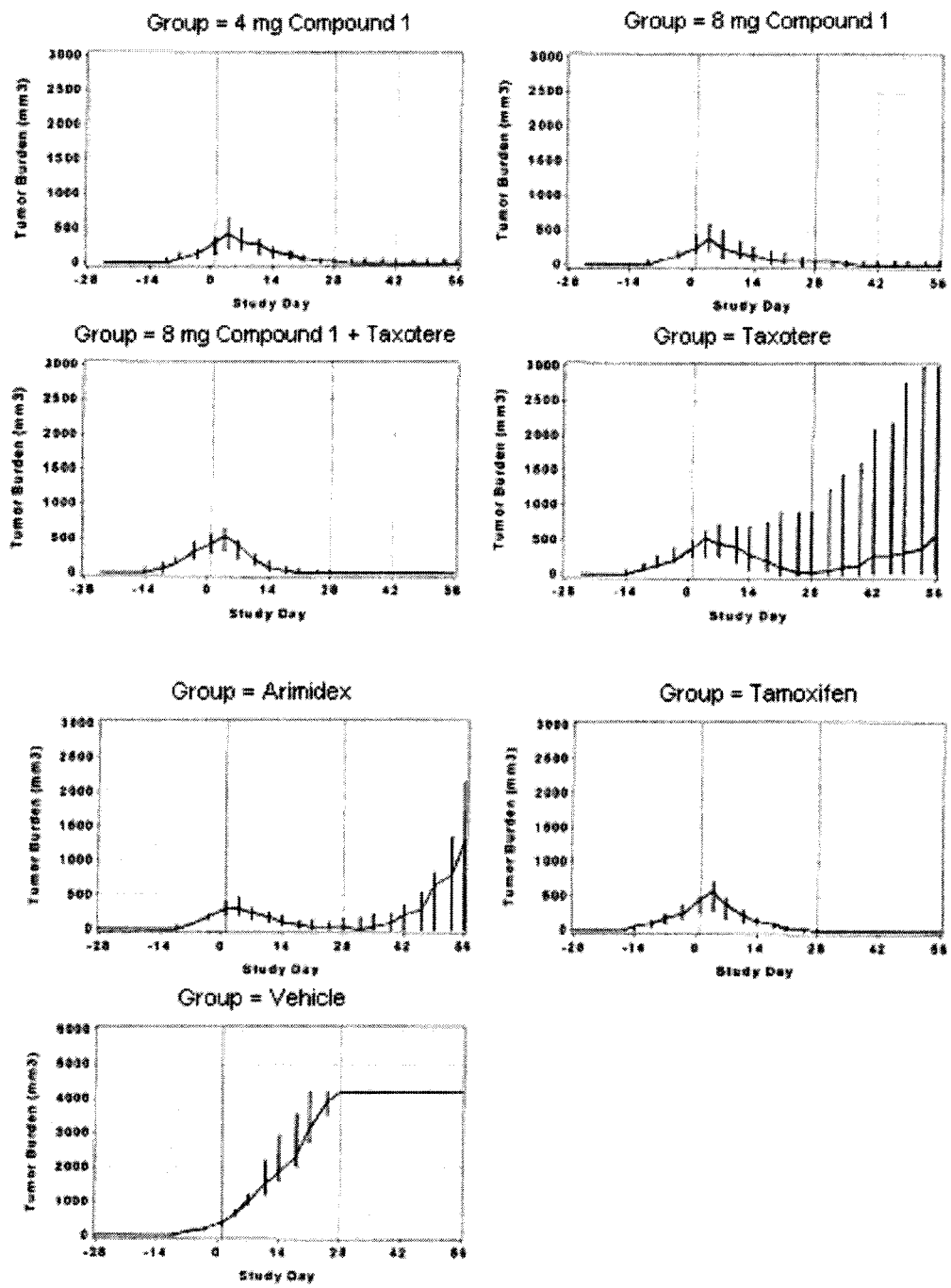
FIG. 26 presents effect of a formulation prepared from crystalline 17α-ethynyl-5α-androstane-3α,17β-diol on tumor burden by volume in a breast cancer model.

FIG. 26 shows tumor burden by volume for the experimental groups during the course of the study. Tumors grow unchecked in the vehicle treated group. Compound 1 treatment consistently shows less tumor burden than for the vehicle treated group (Day 7 on: p<0.001). Combination treatment with Compound 1 and TAXOTERE™ shows smaller burden profiles than TAXOTERE™ alone (Day 7 on: p<0.05).

What is claimed is:

1. Crystalline anhydrate 17α-ethynyl-5α-androstane-3α,17β-diol.

2. The crystalline anhydrate 17α-ethynyl-5α-androstane-3α,17β-diol of claim 1 wherein the crystalline anhydrate contains 10% 10% w/w or less of amorphous 17α-ethynyl-5α-androstane-3α,17β-diol and other crystalline forms of 17α-ethynyl-5α-androstane-3α,17β-diol.

Figure 5A:
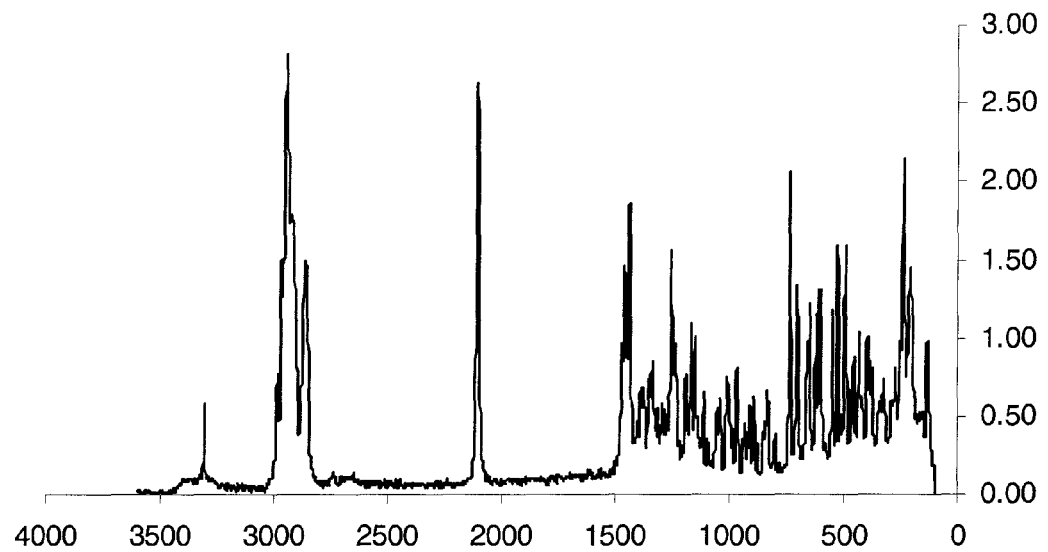
FIG. 5 provides a Raman spectroscopy spectrum with expanded region for a sample comprising Form III 17α-ethynyl-5α-androstane-3α,17β-diol.
Figure 5B:
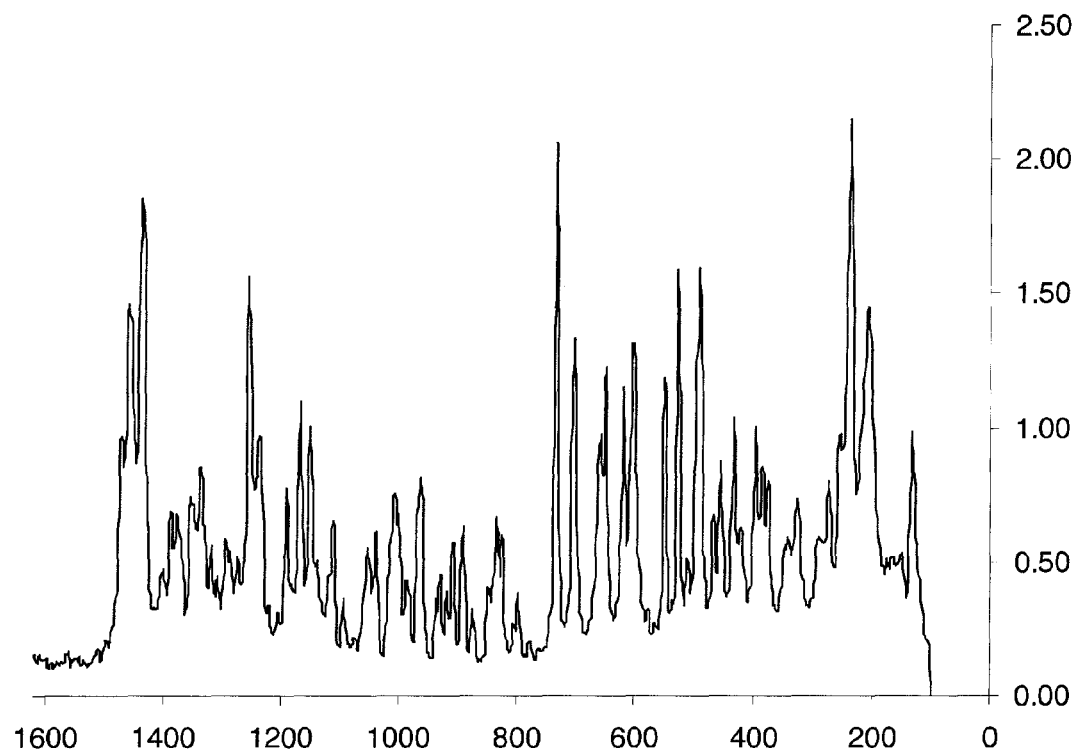

3. The crystalline anhydrate 17α-ethynyl-5α-androstane-3α,17β-diol of claim 2 wherein crystalline anhydrate form of 17α-ethynyl-5α-androstane-3α,17β-diol is Form III wherein Form III comprises at least 90% by weight of all crystalline 17α-ethynyl-5α-androstane-3α,17β-diol that is present, wherein Form III is characterized by or has:
   an X-ray powder diffraction pattern with peak positions of 9.85, 11.33, 15.96, 16.48 and 18.95±0.10 degrees 2-theta or peak positions of 15.96, 16.48 and 18.95±0.10 degrees 2-theta and one two or three peak positions at 9.30, 11.33, 13.45, 16.16 or 17.42±0.10 degrees 2-theta, or
   an IR-Raman spectroscopy spectrum with peak positions at 1236, 1190 and 490 cm$^{-1}$, optionally with one, two or three peak positions at 1458, 1435, 619, 604, 526, 237 or 206 cm$^{-1}$ or is represented by FIG. 5A or FIG. 5B.

4. The crystalline anhydrate 17α-ethynyl-5α-androstane-3α,17β-diol of claim 3 wherein the crystalline anhydrate form of 17α-ethynyl-5α-androstane-3α,17β-diol is Form III, wherein Form III is further characterized by or has:
   a differential scanning calorimetry thermogram with a prominent endotherm at 164° C. obtained using a temperature ramp of 10° C./min and has a thermogravimetric analysis weight loss of 0.5% or less when heated between 4° C. to 105° C. using a temperature ramp of 10° C./min.

5. The crystalline anhydrate 17α-ethynyl-5α-androstane-3α,17β-diol of claim 2 wherein the crystalline anhydrate form of 17α-ethynyl-5α-androstane-3α,17β-diol is Form V, wherein Form V is characterized by or has:
   (i) X-ray powder diffraction pattern with peak positions of 5.82, 9.48, 11.49, 13.50, 15.21, 17.28 and 18.93±0.10 degrees 2θ, or
   (i) and (ii) a TGA thermogram with negligible weight loss, 2% or less weight loss, or 0.3% or less weight loss on heating to the melting point and a DTA or DSC thermogram having an endotherm at about 164° C.

6. The crystalline anhydrate 17α-ethynyl-5α-androstane-3α,17β-diol of claim 2 wherein the crystalline anhydrate form of 17α-ethynyl-5α-androstane-3α,17β-diol is Form VII, wherein Form VII is characterized by or has:
   (i) an XRPD pattern with prominent peaks at about 5.91, 9.78, 13.47, 14.16, 15.78, 17.85, 19.50 and 21.45±0.10 degrees 2θ, or
   (i) and (ii) a TGA thermogram with negligible weight loss, 2% or less weight loss, or 0.3% or less weight loss on heating to the melting point and a DTA or DSC thermogram having an endotherm at about 164° C.

7. The crystalline anhydrate 17α-ethynyl-5α-androstane-3α,17β-diol of claim 2 wherein the crystalline anhydrate form of 17α-ethynyl-5α-androstane-3α,17β-diol is Form VIII, wherein Form VIII is characterized by or has:
   (i) an XRPD pattern with prominent peaks at about 11.13, 15.96, 16.62, 17.76 and 18.75±0.10 degrees 2θ, or
   (i) and (ii) a TGA thermogram with negligible weight loss, 2% or less weight loss, or 0.3% or less weight loss on heating to the melting point and a DTA or DSC thermogram having an endotherm at about 164° C.

8. A pharmaceutical formulation comprising one or more pharmaceutically acceptable excipients and crystalline anhydrate 17α-ethynyl-5α-androstane-3α,17β-diol.

9. The pharmaceutically acceptable formulation of claim 8 wherein the pharmaceutically acceptable formulation is a solid.

10. The pharmaceutically acceptable formulation of claim 9 wherein the solid formulation is present in tablets, capsules or another unit dosage form suitable for oral administration to humans.

11. A method of preparing a pharmaceutically acceptable formulation comprising the step of contacting, mixing and/or blending crystalline anhydrate 17α-ethynyl-5α-androstane-3α,17β-triol with one, two, three, four or more pharmaceutically acceptable excipients to obtain a mixture and processing the mixture to obtain a pharmaceutically acceptable formulation.

12. The method of claim 11 wherein the pharmaceutically acceptable formulation is present in tablets, capsules or another unit dosage form suitable for oral administration to humans.

13. The method of claim 11 wherein the crystalline anhydrate form of 17α-ethynyl-5α-androstane-3α,17β-diol is Form III.

14. The method of claim 11 wherein at least one of the excipients is a surface active agent.

15. The method of claim 14 wherein the surface active agent is sodium lauryl sulfate or Polysorbate-80.

* * * * *